(12) United States Patent
Graul et al.

(10) Patent No.: US 10,238,379 B2
(45) Date of Patent: *Mar. 26, 2019

(54) METHOD AND APPARATUS FOR ATTACHING TISSUE TO BONE, INCLUDING THE PROVISION AND USE OF A NOVEL KNOTLESS SUTURE ANCHOR SYSTEM

(71) Applicant: Pivot Medical, Inc., Sunnyvale, CA (US)

(72) Inventors: Jeremy Graul, Elk Grove, CA (US); J. Brook Burley, Mountain View, CA (US)

(73) Assignee: Pivot Medical, Inc., Sunnyvale, CA (US)

( * ) Notice: Subject to any disclaimer, the term of this patent is extended or adjusted under 35 U.S.C. 154(b) by 151 days.

This patent is subject to a terminal disclaimer.

(21) Appl. No.: 15/231,227

(22) Filed: Aug. 8, 2016

(65) Prior Publication Data

US 2016/0338693 A1    Nov. 24, 2016

Related U.S. Application Data

(63) Continuation-in-part of application No. 14/568,805, filed on Dec. 12, 2014, now Pat. No. 9,826,973.

(Continued)

(51) Int. Cl.
*A61B 17/04* (2006.01)
*A61B 90/00* (2016.01)
(Continued)

(52) U.S. Cl.
CPC ...... *A61B 17/0401* (2013.01); *A61B 17/0485* (2013.01); *A61B 90/08* (2016.02);
(Continued)

(58) Field of Classification Search
CPC ........ A61B 17/0401; A61B 2017/0409; A61B 2017/0414; A61B 2017/042;
(Continued)

(56) References Cited

U.S. PATENT DOCUMENTS

| | | |
|---|---|---|
| 919,138 A | 4/1909 | Dranke et al. |
| 2,416,260 A | 2/1947 | Karle |

(Continued)

FOREIGN PATENT DOCUMENTS

| | | |
|---|---|---|
| EP | 0 232 049 | 8/1987 |
| EP | 0 241 240 | 10/1987 |

(Continued)

*Primary Examiner* — Robert Lynch
(74) *Attorney, Agent, or Firm* — Pandiscio & Pandiscio

(57) ABSTRACT

Apparatus for securing an object to bone, the apparatus comprising: an anchor, the anchor comprising: a body comprising an opening for receiving a filament therein; and a locking element movably mounted to the body for selectively locking the filament to the body; and an inserter for deploying the anchor in bone, the inserter comprising: a handle; an overtube extending distally from the handle; a carriage movably mounted to the handle; a shaft movably mounted within the overtube and connected to the carriage and releasably connected to the body of the anchor, the shaft being hollow; and a rod movably mounted within the shaft and connected to the locking element.

25 Claims, 43 Drawing Sheets

Related U.S. Application Data which is a continuation-in-part of application No. 13/830,501, filed on Mar. 14, 2013, now Pat. No. 9,149,268, which is a continuation-in-part of application No. 13/642,168, filed as application No. PCT/US2011/021173 on Jan. 13, 2011, now Pat. No. 9,451,943, which is a continuation-in-part of application No. 12/839,246, filed on Jul. 19, 2010, now Pat. No. 9,179,905, said application No. 13/830,501 is a continuation-in-part of application No. 13/538,378, filed on Jun. 29, 2012, now Pat. No. 9,101,355.

(60) Provisional application No. 62/201,627, filed on Aug. 6, 2015, provisional application No. 61/915,004, filed on Dec. 12, 2013, provisional application No. 61/718,997, filed on Oct. 26, 2012, provisional application No. 61/644,129, filed on May 8, 2012, provisional application No. 61/502,621, filed on Jun. 29, 2011, provisional application No. 61/326,709, filed on Apr. 22, 2010, provisional application No. 61/271,205, filed on Jul. 17, 2009.

(51) Int. Cl.
*A61B 90/57* (2016.01)
*A61B 17/00* (2006.01)

(52) U.S. Cl.
CPC .... *A61B 90/57* (2016.02); *A61B 2017/00296* (2013.01); *A61B 2017/00309* (2013.01); *A61B 2017/045* (2013.01); *A61B 2017/0409* (2013.01); *A61B 2017/0412* (2013.01); *A61B 2017/0414* (2013.01); *A61B 2017/0424* (2013.01); *A61B 2017/0425* (2013.01); *A61B 2017/0445* (2013.01); *A61B 2017/0448* (2013.01); *A61B 2017/0453* (2013.01); *A61B 2017/0458* (2013.01); *A61B 2090/0811* (2016.02)

(58) Field of Classification Search
CPC .... A61B 2017/0422; A61B 2017/0424; A61B 2017/0427; A61B 2017/0429; A61B 2017/043; A61B 2017/0432
See application file for complete search history.

(56) References Cited

U.S. PATENT DOCUMENTS

| | | |
|---|---|---|
| 2,579,192 A | 12/1951 | Kohl |
| 2,808,055 A | 10/1957 | Thayer |
| 3,566,739 A | 3/1971 | Lebar |
| 3,708,883 A | 1/1973 | Flander |
| 4,408,938 A | 10/1983 | Maguire |
| 4,484,570 A | 11/1984 | Sutter et al. |
| 4,492,226 A | 1/1985 | Belykh et al. |
| 4,590,928 A | 5/1986 | Hunt et al. |
| 4,605,414 A | 8/1986 | Czajka |
| 4,632,100 A | 12/1986 | Somers et al. |
| 4,708,132 A | 11/1987 | Silvestrini |
| 4,741,330 A | 5/1988 | Hayhurst |
| 4,778,468 A | 10/1988 | Hunt et al. |
| 4,779,616 A | 10/1988 | Johnson |
| 4,870,957 A | 10/1989 | Goble et al. |
| 4,871,289 A | 10/1989 | Choiniere |
| 4,927,421 A | 5/1990 | Goble et al. |
| 5,037,422 A | 8/1991 | Hayhurst et al. |
| 5,046,513 A | 9/1991 | Gatturna et al. |
| 5,176,682 A | 1/1993 | Chow |
| 5,207,679 A | 5/1993 | Li |
| 5,209,753 A | 5/1993 | Biedermann et al. |
| 5,224,946 A | 7/1993 | Hayhurst et al. |
| 5,226,426 A | 7/1993 | Yoon |
| 5,236,445 A | 8/1993 | Hayhurst et al. |
| 5,268,001 A | 12/1993 | Nicholson et al. |
| 5,324,308 A | 6/1994 | Pierce |
| 5,330,442 A | 7/1994 | Green et al. |
| 5,336,240 A | 8/1994 | Metzler et al. |
| 5,354,298 A | 10/1994 | Lee et al. |
| 5,364,407 A | 11/1994 | Poll |
| 5,383,905 A | 1/1995 | Golds et al. |
| 5,405,352 A | 4/1995 | Weston |
| 5,411,523 A | 5/1995 | Goble |
| 5,417,712 A | 5/1995 | Whittaker et al. |
| 5,423,860 A | 6/1995 | Lizardi et al. |
| 5,464,427 A | 11/1995 | Curtis et al. |
| 5,472,452 A | 12/1995 | Trott |
| 5,480,403 A | 1/1996 | Lee et al. |
| 5,486,197 A | 1/1996 | Le et al. |
| 5,489,210 A | 2/1996 | Hanosh |
| 5,499,991 A | 3/1996 | Garman et al. |
| 5,501,683 A | 3/1996 | Trott |
| 5,501,692 A | 3/1996 | Riza |
| 5,501,695 A | 3/1996 | Anspach, Jr. et al. |
| 5,514,159 A | 5/1996 | Matula et al. |
| 5,522,844 A | 6/1996 | Johnson |
| 5,522,845 A | 6/1996 | Wenstrom, Jr. |
| 5,534,012 A | 7/1996 | Bonutti |
| 5,545,180 A | 8/1996 | Le et al. |
| 5,562,683 A | 10/1996 | Chan |
| 5,562,687 A | 10/1996 | Chan |
| 5,569,306 A | 10/1996 | Thal |
| 5,571,139 A | 11/1996 | Jenkins, Jr. |
| 5,584,835 A | 12/1996 | Greenfield |
| 5,601,557 A | 2/1997 | Hayhurst |
| 5,601,558 A | 2/1997 | Torrie et al. |
| 5,611,515 A | 3/1997 | Benderev et al. |
| 5,630,824 A | 5/1997 | Hart |
| 5,632,748 A | 5/1997 | Beck, Jr. et al. |
| 5,643,292 A | 7/1997 | Hart |
| 5,643,321 A | 7/1997 | McDevitt |
| 5,645,589 A | 7/1997 | Li |
| 5,647,874 A | 7/1997 | Hayhurst |
| 5,649,963 A | 7/1997 | McDevitt |
| 5,658,313 A | 8/1997 | Thal |
| 5,662,658 A | 9/1997 | Wenstrom, Jr. |
| 5,665,112 A | 9/1997 | Thal |
| 5,681,320 A | 10/1997 | McGuire |
| 5,681,333 A | 10/1997 | Burkhart et al. |
| 5,683,419 A | 11/1997 | Thal |
| 5,690,649 A | 11/1997 | Li |
| 5,702,215 A | 12/1997 | Li |
| 5,702,397 A | 12/1997 | Goble et al. |
| 5,702,422 A | 12/1997 | Stone |
| 5,707,395 A | 1/1998 | Li |
| 5,709,708 A | 1/1998 | Thal |
| 5,713,903 A | 2/1998 | Sander et al. |
| 5,716,368 A | 2/1998 | de la Torre et al. |
| 5,720,765 A | 2/1998 | Thal |
| 5,725,529 A | 3/1998 | Nicholson et al. |
| 5,725,541 A | 3/1998 | Anspach, III et al. |
| 5,728,136 A | 3/1998 | Thal |
| 5,741,300 A | 4/1998 | Li |
| 5,746,752 A | 5/1998 | Burkhart |
| 5,746,753 A | 5/1998 | Sullivan et al. |
| 5,755,728 A | 5/1998 | Maki |
| 5,782,862 A | 7/1998 | Bonutti |
| 5,782,863 A | 7/1998 | Bartlett |
| 5,782,864 A | 7/1998 | Lizardi |
| 5,791,899 A | 8/1998 | Sachdeva et al. |
| 5,797,963 A | 8/1998 | McDevitt |
| 5,814,071 A | 9/1998 | McDevitt et al. |
| 5,814,072 A | 9/1998 | Bonutti |
| 5,814,073 A | 9/1998 | Bonutti |
| 5,843,127 A | 12/1998 | Li |
| 5,845,645 A | 12/1998 | Bonutti |
| 5,849,004 A | 12/1998 | Bramlet |
| 5,891,168 A | 4/1999 | Thal |
| 5,906,624 A | 5/1999 | Wenstrom, Jr. |
| 5,910,148 A | 6/1999 | Reimels et al. |
| 5,911,721 A | 6/1999 | Nicholson et al. |
| 5,928,244 A | 7/1999 | Tovey et al. |

(56) References Cited

U.S. PATENT DOCUMENTS

| | | |
|---|---|---|
| 5,935,129 A | 8/1999 | McDevitt et al. |
| 5,935,134 A | 8/1999 | Pedlick et al. |
| 5,935,149 A | 8/1999 | Ek |
| 5,948,000 A | 9/1999 | Larsen et al. |
| 5,948,001 A | 9/1999 | Larsen |
| 5,957,953 A | 9/1999 | DiPoto et al. |
| 5,968,044 A | 10/1999 | Nicholson et al. |
| 5,980,558 A | 11/1999 | Wiley |
| 5,980,559 A | 11/1999 | Bonutti |
| 5,993,459 A | 11/1999 | Larsen et al. |
| 6,010,514 A | 1/2000 | Burney et al. |
| 6,022,360 A | 2/2000 | Reimels et al. |
| 6,041,485 A | 3/2000 | Pedlick et al. |
| 6,045,573 A | 4/2000 | Wenstrom, Jr. et al. |
| 6,045,574 A | 4/2000 | Thal |
| 6,056,772 A | 5/2000 | Bonutti |
| 6,077,277 A | 6/2000 | Mollenauer et al. |
| 6,086,608 A | 7/2000 | Ek et al. |
| 6,099,538 A | 8/2000 | Moses et al. |
| 6,099,547 A | 8/2000 | Gellman et al. |
| 6,117,144 A | 9/2000 | Nobles et al. |
| 6,143,017 A | 11/2000 | Thal |
| 6,149,669 A | 11/2000 | Li |
| 6,159,234 A | 12/2000 | Bonutti et al. |
| 6,200,329 B1 | 3/2001 | Fung et al. |
| 6,221,107 B1 | 4/2001 | Steiner et al. |
| 6,231,592 B1 | 5/2001 | Bonutti et al. |
| 6,241,732 B1 | 6/2001 | Overaker et al. |
| 6,245,081 B1 | 6/2001 | Bowman et al. |
| 6,245,082 B1 | 6/2001 | Gellman et al. |
| 6,312,448 B1 | 11/2001 | Bonutti |
| 6,319,252 B1 | 11/2001 | McDevitt et al. |
| 6,319,269 B1 | 11/2001 | Li |
| 6,475,230 B1 | 11/2002 | Bonutti et al. |
| RE37,963 E | 1/2003 | Thal |
| 6,506,190 B1 | 1/2003 | Walshe |
| 6,517,579 B1 | 2/2003 | Paulos et al. |
| 6,520,980 B1 | 2/2003 | Foerster |
| 6,524,316 B1 | 2/2003 | Nicholson et al. |
| 6,527,794 B1 | 3/2003 | McDevitt et al. |
| 6,527,795 B1 | 3/2003 | Lizardi |
| 6,544,281 B2 | 4/2003 | ElAttrache et al. |
| 6,547,800 B2 | 4/2003 | Foerster et al. |
| 6,547,807 B2 | 4/2003 | Chan et al. |
| 6,562,071 B2 | 5/2003 | Järvinen |
| 6,575,976 B2 | 6/2003 | Grafton |
| 6,575,987 B2 | 6/2003 | Gellman et al. |
| 6,582,453 B1 | 6/2003 | Tran et al. |
| 6,585,730 B1 | 7/2003 | Foerster |
| 6,620,166 B1 | 9/2003 | Wenstrom, Jr. et al. |
| 6,629,984 B1 | 10/2003 | Chan |
| 6,641,596 B1 | 11/2003 | Lizardi |
| 6,641,597 B2 | 11/2003 | Burkhart et al. |
| 6,660,008 B1 | 12/2003 | Foerster et al. |
| 6,660,023 B2 | 12/2003 | McDevitt et al. |
| 6,673,094 B1 | 1/2004 | McDevitt et al. |
| 6,692,516 B2 | 2/2004 | West, Jr. et al. |
| 6,733,506 B1 | 5/2004 | McDevitt et al. |
| 6,746,457 B2 | 6/2004 | Dana et al. |
| 6,752,814 B2 | 6/2004 | Gellman et al. |
| 6,770,073 B2 | 8/2004 | McDevitt et al. |
| 6,770,076 B2 | 8/2004 | Foerster |
| 6,780,198 B1 | 8/2004 | Gregoire et al. |
| 6,814,741 B2 | 11/2004 | Bowman et al. |
| 6,855,157 B2 | 2/2005 | Foerster et al. |
| 6,887,259 B2 | 5/2005 | Lizardi |
| 6,932,834 B2 | 8/2005 | Lizardi et al. |
| 6,942,666 B2 | 9/2005 | Overaker et al. |
| 6,986,781 B2 | 1/2006 | Smith |
| 6,991,636 B2 | 1/2006 | Rose |
| 7,033,380 B2 | 4/2006 | Schwartz et al. |
| 7,037,324 B2 | 5/2006 | Martinek |
| 7,041,120 B2 | 5/2006 | Li et al. |
| 7,048,755 B2 | 5/2006 | Bonutti et al. |
| 7,074,203 B1 | 7/2006 | Johanson et al. |
| 7,081,126 B2 | 7/2006 | McDevitt et al. |
| 7,083,638 B2 | 8/2006 | Foerster |
| 7,090,690 B2 | 8/2006 | Foerster et al. |
| 7,144,415 B2 | 12/2006 | Del Rio et al. |
| 7,160,314 B2 | 1/2007 | Sgro et al. |
| 7,226,469 B2 | 6/2007 | Benavitz et al. |
| 7,235,100 B2 | 6/2007 | Martinek |
| 7,309,346 B2 | 12/2007 | Martinek |
| 7,329,272 B2 | 2/2008 | Burkhart et al. |
| 7,381,213 B2 | 6/2008 | Lizardi |
| 7,507,200 B2 | 3/2009 | Okada |
| 7,517,357 B2 | 4/2009 | Abrams et al. |
| 7,556,640 B2 | 7/2009 | Foerster |
| 7,637,926 B2 | 12/2009 | Foerster et al. |
| 7,662,171 B2 | 2/2010 | West, Jr. et al. |
| 7,674,274 B2 | 3/2010 | Foerster et al. |
| 7,674,276 B2 | 3/2010 | Stone et al. |
| 7,682,374 B2 | 3/2010 | Foerster et al. |
| 7,695,494 B2 | 4/2010 | Foerster |
| 7,704,262 B2 | 4/2010 | Bellafiore et al. |
| 7,713,286 B2 | 5/2010 | Singhatat |
| 7,780,701 B1 | 8/2010 | Meridew et al. |
| 7,794,484 B2 | 9/2010 | Stone et al. |
| 7,828,820 B2 | 11/2010 | Stone et al. |
| 7,837,710 B2 | 11/2010 | Lombardo et al. |
| 7,842,050 B2 | 11/2010 | Diduch et al. |
| 7,846,167 B2 | 12/2010 | Garcia et al. |
| 7,867,264 B2 | 1/2011 | McDevitt et al. |
| 7,896,907 B2 | 3/2011 | McDevitt et al. |
| 7,938,847 B2 | 5/2011 | Fanton et al. |
| 7,963,972 B2 | 6/2011 | Foerster et al. |
| 7,976,565 B1 | 7/2011 | Meridew et al. |
| 7,993,369 B2 | 8/2011 | Dreyfuss |
| 8,029,537 B2 | 10/2011 | West, Jr. et al. |
| 8,057,524 B2 | 11/2011 | Meridew |
| 8,066,718 B2 | 11/2011 | Weisel et al. |
| 8,075,572 B2 | 12/2011 | Stefanchik et al. |
| RE43,143 E | 1/2012 | Hayhurst |
| 8,100,942 B1 | 1/2012 | Green et al. |
| 8,109,969 B1 | 2/2012 | Green et al. |
| 8,118,835 B2 | 2/2012 | Weisel et al. |
| 8,128,641 B2 | 3/2012 | Wardle |
| 8,133,258 B2 | 3/2012 | Foerster et al. |
| 8,137,381 B2 | 3/2012 | Foerster et al. |
| 8,137,383 B2 | 3/2012 | West, Jr. et al. |
| 8,162,978 B2 | 4/2012 | Lombardo et al. |
| 8,298,291 B2 | 10/2012 | Ewers et al. |
| 8,409,252 B2 | 4/2013 | Lombardo et al. |
| 8,435,264 B2 | 5/2013 | Sojka et al. |
| 8,444,672 B2 | 5/2013 | Foerster |
| 8,444,674 B2 | 5/2013 | Kaplan |
| 8,454,704 B2 | 6/2013 | Frushell et al. |
| 8,460,340 B2 | 6/2013 | Sojka et al. |
| 8,469,998 B2 | 6/2013 | Sojka et al. |
| 8,491,600 B2 | 7/2013 | McDevitt et al. |
| 8,523,902 B2 | 9/2013 | Heaven et al. |
| 8,545,535 B2 | 10/2013 | Hirotsuka et al. |
| 8,545,536 B2 | 10/2013 | Mayer et al. |
| 8,613,756 B2 | 12/2013 | Lizardi et al. |
| 8,632,568 B2 | 1/2014 | Miller et al. |
| 8,834,543 B2 | 9/2014 | McDevitt et al. |
| 8,986,345 B2 | 3/2015 | Denham et al. |
| 2001/0002436 A1 | 5/2001 | Bowman et al. |
| 2001/0049529 A1 | 12/2001 | Cachia et al. |
| 2002/0040241 A1 | 4/2002 | Jarvinen |
| 2002/0115999 A1 | 8/2002 | McDevitt et al. |
| 2002/0147456 A1 | 10/2002 | Diduch et al. |
| 2003/0004545 A1 | 1/2003 | Burkhart et al. |
| 2003/0065361 A1 | 4/2003 | Dreyfuss |
| 2003/0139752 A1 | 7/2003 | Pasricha et al. |
| 2003/0195563 A1 | 10/2003 | Foerster |
| 2003/0195564 A1 | 10/2003 | Tran et al. |
| 2004/0093031 A1 | 5/2004 | Burkhart et al. |
| 2004/0138706 A1 | 7/2004 | Abrams et al. |
| 2004/0220573 A1 | 11/2004 | McDevitt et al. |
| 2004/0249393 A1 | 12/2004 | Weisel et al. |
| 2005/0004644 A1 | 1/2005 | Kelsch et al. |
| 2005/0049592 A1 | 3/2005 | Keith et al. |
| 2005/0075668 A1 | 4/2005 | Lizardi |

(56) References Cited

U.S. PATENT DOCUMENTS

| | | |
|---|---|---|
| 2005/0149122 A1 | 7/2005 | McDevitt et al. |
| 2005/0245932 A1 | 11/2005 | Fanton et al. |
| 2005/0277986 A1 | 12/2005 | Foerster et al. |
| 2005/0283171 A1 | 12/2005 | Bellafiore et al. |
| 2006/0052788 A1 | 3/2006 | Thelen et al. |
| 2006/0079904 A1 | 4/2006 | Thal |
| 2006/0081553 A1 | 4/2006 | Patterson et al. |
| 2006/0106423 A1 | 5/2006 | Weisel et al. |
| 2006/0217762 A1 | 9/2006 | Maahs et al. |
| 2006/0235413 A1 | 10/2006 | Denham et al. |
| 2006/0265010 A1 | 11/2006 | Paraschac et al. |
| 2006/0282081 A1 | 12/2006 | Fanton et al. |
| 2006/0282082 A1 | 12/2006 | Fanton et al. |
| 2006/0282083 A1 | 12/2006 | Fanton et al. |
| 2007/0005068 A1 | 1/2007 | Sklar |
| 2007/0060922 A1 | 3/2007 | Dreyfuss |
| 2007/0093858 A1 | 4/2007 | Gambale et al. |
| 2007/0142835 A1 | 6/2007 | Green et al. |
| 2007/0156149 A1 | 7/2007 | Fanton et al. |
| 2007/0156150 A1 | 7/2007 | Fanton et al. |
| 2007/0156176 A1 | 7/2007 | Fanton et al. |
| 2007/0203498 A1 | 8/2007 | Gerber et al. |
| 2007/0219557 A1 | 9/2007 | Bourque et al. |
| 2007/0255317 A1 | 11/2007 | Fanton et al. |
| 2007/0260259 A1 | 11/2007 | Fanton et al. |
| 2007/0270889 A1 | 11/2007 | Conlon et al. |
| 2007/0270907 A1 | 11/2007 | Stokes et al. |
| 2007/0288027 A1 | 12/2007 | Grafton et al. |
| 2008/0033460 A1 | 2/2008 | Ziniti et al. |
| 2008/0086138 A1 | 4/2008 | Stone et al. |
| 2008/0275469 A1 | 11/2008 | Fanton et al. |
| 2008/0294177 A1 | 11/2008 | To et al. |
| 2008/0306510 A1 | 12/2008 | Stchur |
| 2009/0018554 A1 | 1/2009 | Thorne et al. |
| 2009/0082807 A1 | 3/2009 | Miller et al. |
| 2009/0099598 A1 | 4/2009 | McDevitt et al. |
| 2009/0112214 A1 | 4/2009 | Philippon et al. |
| 2009/0192545 A1 | 7/2009 | Workman |
| 2009/0222041 A1 | 9/2009 | Foerster |
| 2009/0248068 A1 | 10/2009 | Lombardo et al. |
| 2009/0292321 A1 | 11/2009 | Collette |
| 2009/0299386 A1 | 12/2009 | Meridew |
| 2009/0306711 A1 | 12/2009 | Stone et al. |
| 2009/0312794 A1 | 12/2009 | Nason et al. |
| 2010/0004683 A1 | 1/2010 | Hoof et al. |
| 2010/0049213 A1 | 2/2010 | Serina et al. |
| 2010/0063542 A1 | 3/2010 | van der Burg et al. |
| 2010/0069925 A1 | 3/2010 | Friedman et al. |
| 2010/0094314 A1 | 4/2010 | Hernlund et al. |
| 2010/0094355 A1 | 4/2010 | Trenhaile |
| 2010/0094425 A1 | 4/2010 | Bentley et al. |
| 2010/0100127 A1 | 4/2010 | Trenhaile |
| 2010/0114162 A1 | 5/2010 | Bojarski et al. |
| 2010/0121348 A1 | 5/2010 | van der Burg et al. |
| 2010/0121349 A1 | 5/2010 | Meier et al. |
| 2010/0191283 A1 | 7/2010 | Foerster et al. |
| 2010/0198258 A1 | 8/2010 | Heaven et al. |
| 2010/0222812 A1 | 9/2010 | Stone et al. |
| 2010/0251861 A1 | 10/2010 | Sixto, Jr. et al. |
| 2010/0292731 A1 | 11/2010 | Gittings et al. |
| 2010/0305576 A1 | 12/2010 | Ferguson et al. |
| 2011/0015674 A1 | 1/2011 | Howard et al. |
| 2011/0046682 A1 | 2/2011 | Stephan et al. |
| 2011/0071545 A1 | 3/2011 | Pamichev et al. |
| 2011/0071549 A1 | 3/2011 | Caborn et al. |
| 2011/0098728 A1 | 4/2011 | McDevitt et al. |
| 2011/0152929 A1 | 6/2011 | McDevitt et al. |
| 2011/0224726 A1 | 9/2011 | Lombardo et al. |
| 2011/0238113 A1 | 9/2011 | Fanton et al. |
| 2011/0264140 A1 | 10/2011 | Lizardi et al. |
| 2011/0295279 A1 | 12/2011 | Stone et al. |
| 2011/0301621 A1 | 12/2011 | Oren et al. |
| 2011/0301622 A1 | 12/2011 | Oren et al. |
| 2012/0041485 A1 | 2/2012 | Kaiser et al. |
| 2012/0053629 A1 | 3/2012 | Reiser et al. |
| 2012/0059417 A1 | 3/2012 | Norton et al. |
| 2012/0143221 A1 | 6/2012 | Weisel et al. |
| 2012/0150223 A1 | 6/2012 | Manos et al. |
| 2013/0006276 A1 | 1/2013 | Lantz et al. |
| 2013/0023930 A1 | 1/2013 | Stone et al. |
| 2013/0096611 A1 | 4/2013 | Sullivan |
| 2013/0103083 A1 | 4/2013 | Baird |
| 2013/0138152 A1 | 5/2013 | Stone et al. |
| 2013/0144334 A1 | 6/2013 | Bouduban et al. |
| 2013/0144338 A1 | 6/2013 | Stone et al. |
| 2013/0184748 A1 | 7/2013 | Sojka et al. |
| 2013/0204298 A1 | 8/2013 | Graul et al. |
| 2013/0267998 A1 | 10/2013 | Vijay et al. |
| 2013/0296931 A1 | 11/2013 | Sengun |
| 2014/0249579 A1 | 9/2014 | Heaven et al. |
| 2014/0257382 A1 | 9/2014 | McCartney |
| 2014/0316460 A1 | 10/2014 | Graul et al. |
| 2015/0100087 A1 | 4/2015 | Graul et al. |

FOREIGN PATENT DOCUMENTS

| | | |
|---|---|---|
| EP | 0 251 583 | 1/1988 |
| EP | 0 270 704 | 6/1988 |
| EP | 0 318 426 | 5/1989 |
| EP | 0 574 707 | 12/1993 |
| EP | 0 673 624 | 9/1995 |
| EP | 0 834 281 | 4/1998 |
| EP | 1 016 377 | 7/2000 |
| EP | 1 568 327 | 8/2005 |
| EP | 1 762 187 | 3/2007 |
| EP | 1 825 817 | 8/2007 |
| EP | 2 335 603 | 6/2011 |
| WO | WO 92/04874 | 4/1992 |
| WO | WO 95/15726 | 6/1995 |
| WO | WO 97/03615 | 2/1997 |
| WO | WO 97/30649 | 8/1997 |
| WO | WO 98/38938 | 9/1998 |
| WO | WO 2008/063915 | 5/2008 |
| WO | WO 2011/060022 | 5/2011 |
| WO | WO 2012/034131 | 3/2012 |

CAM-TYPE FEMOROACETABULAR IMPINGEMENT (FAI)
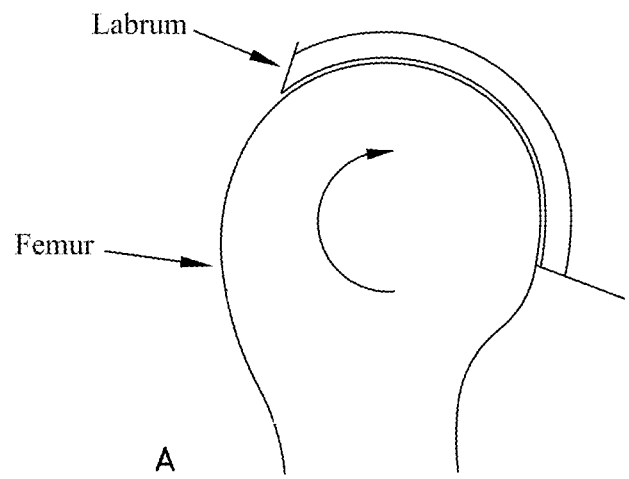
CAM INJURY TO THE LABRUM
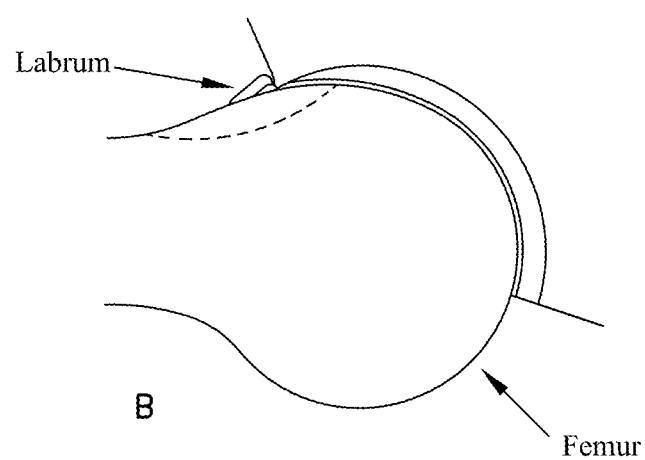
FIG. 13

PINCER-TYPE FEMOROACETABULAR IMPINGEMENT (FAI)
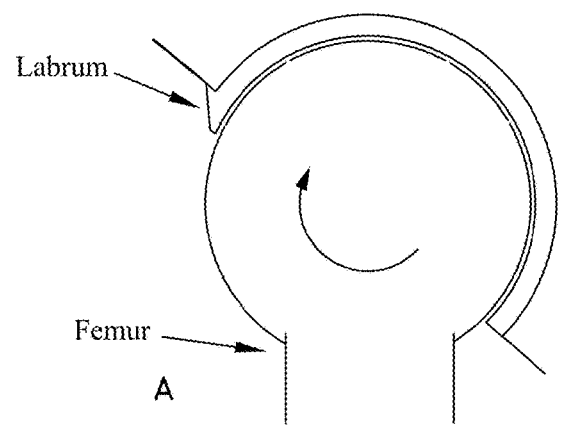
PINCER INJURY TO THE LABRUM
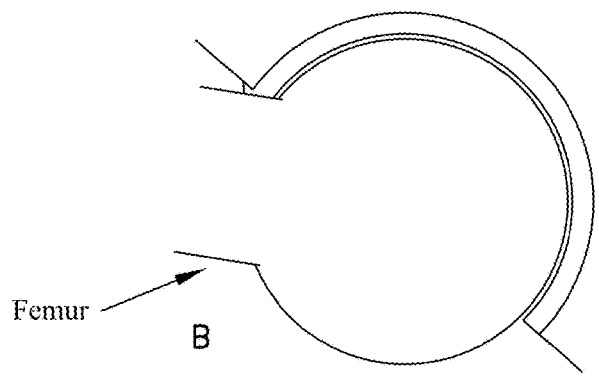
FIG. 14

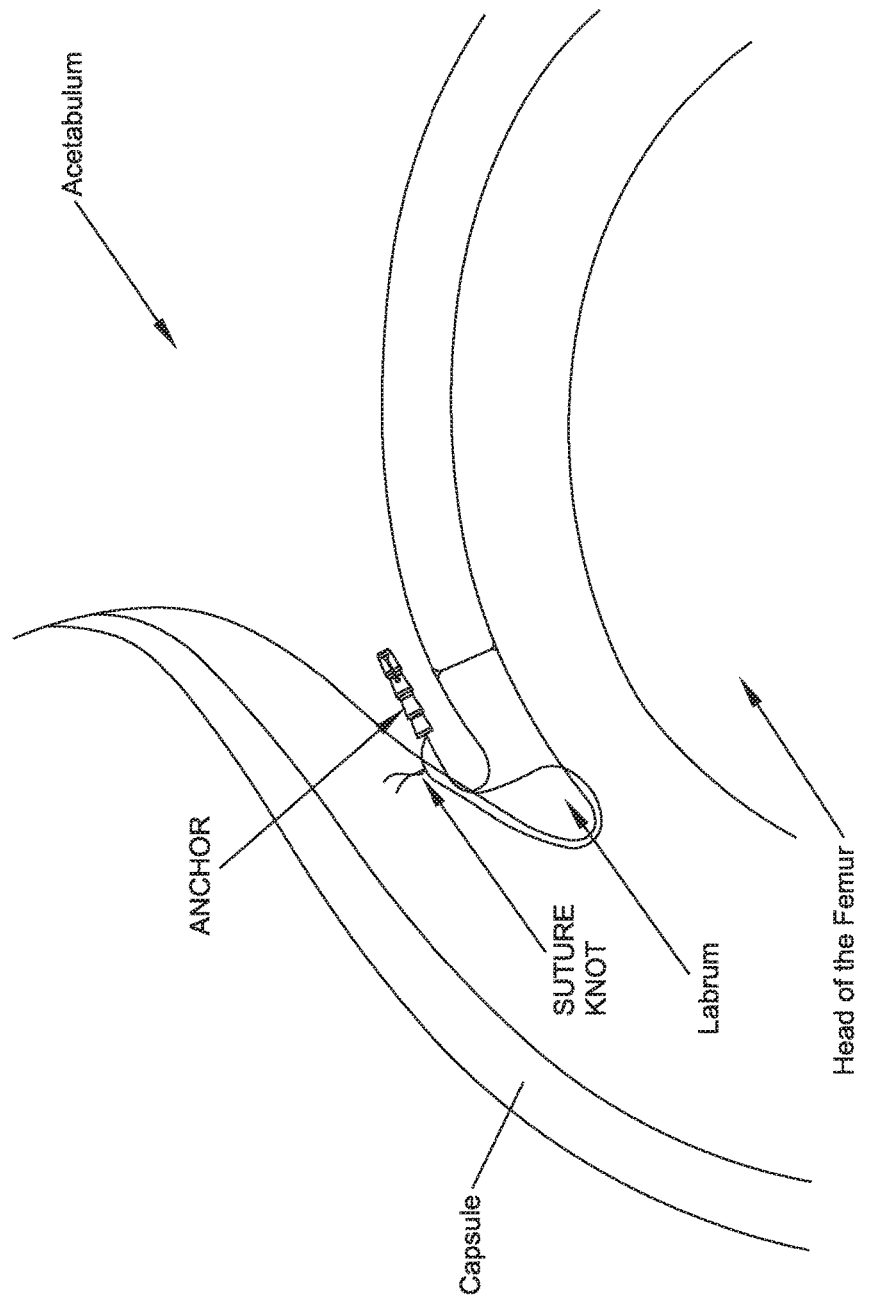

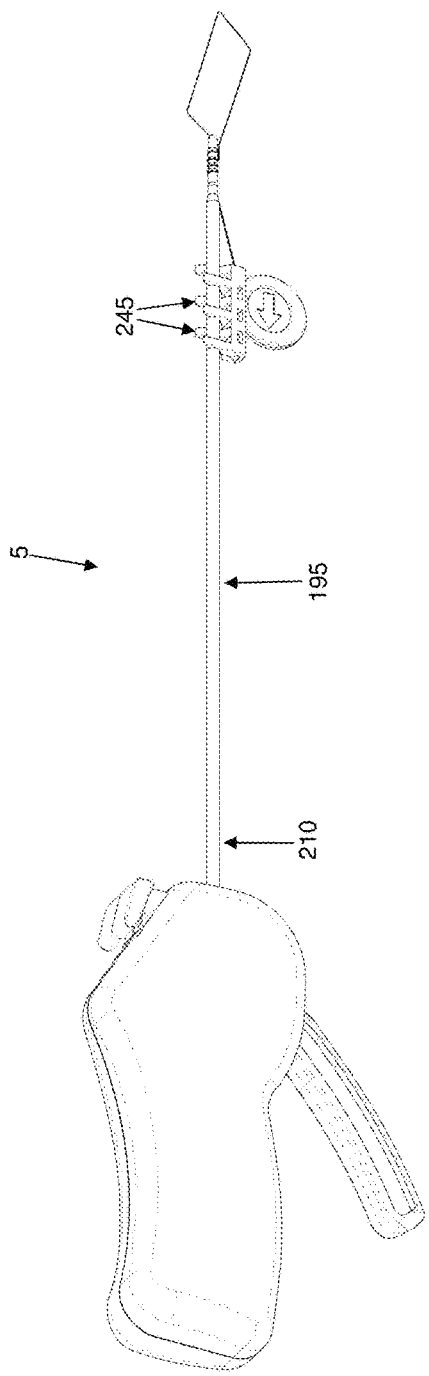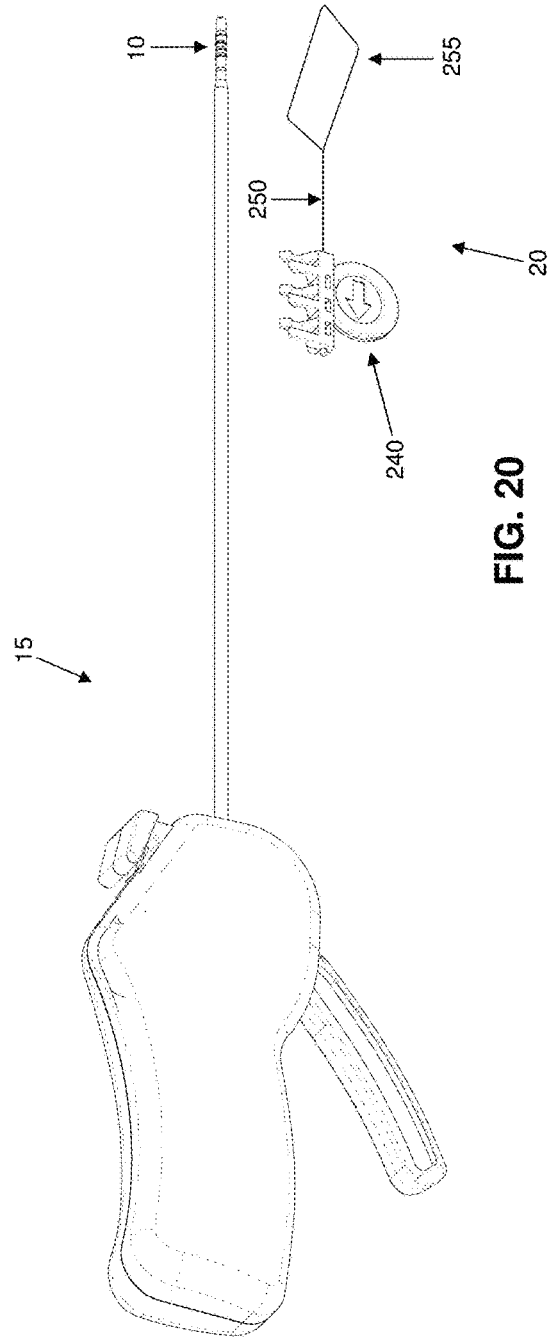

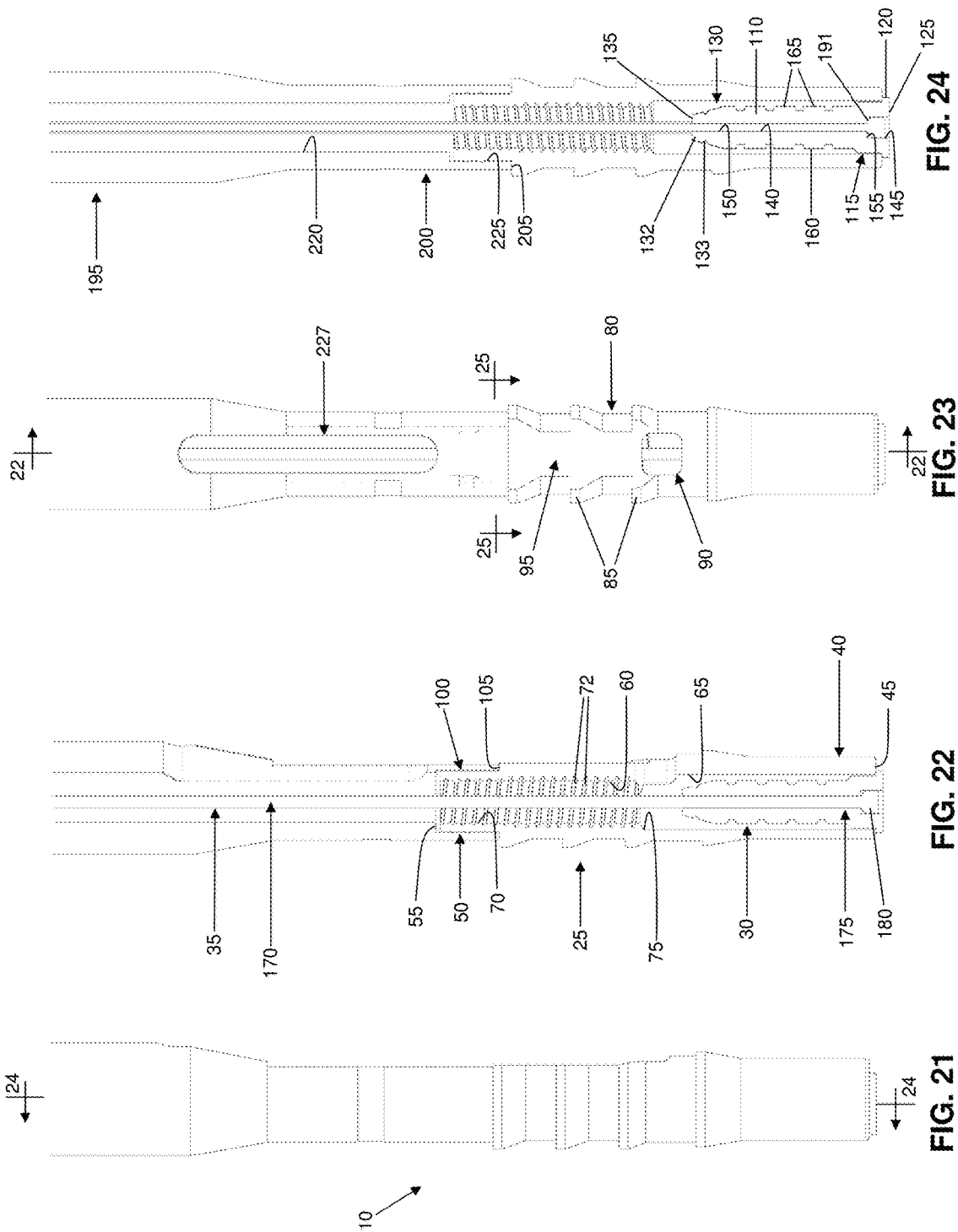

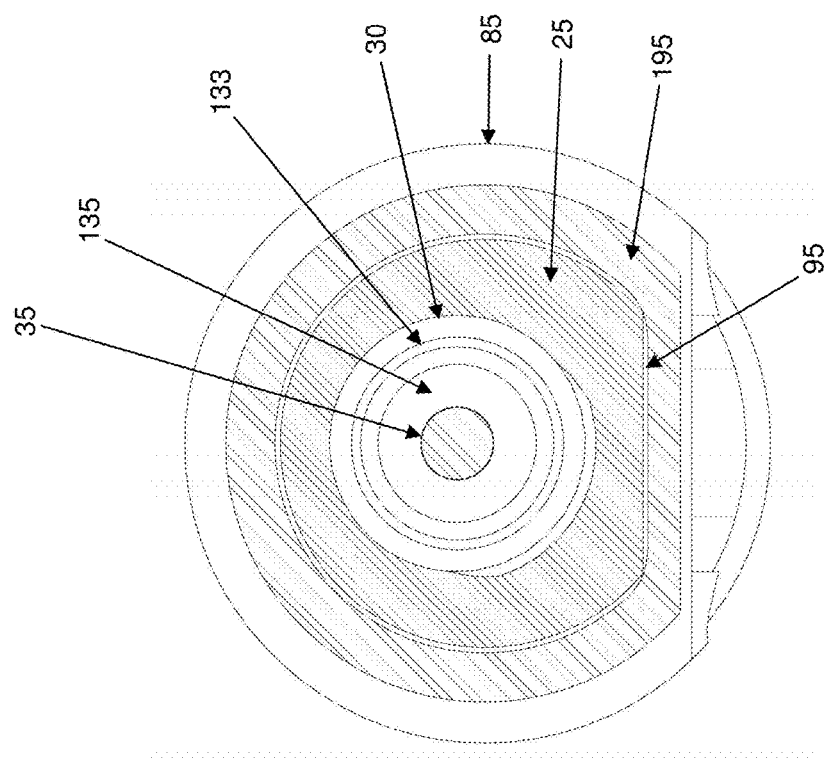

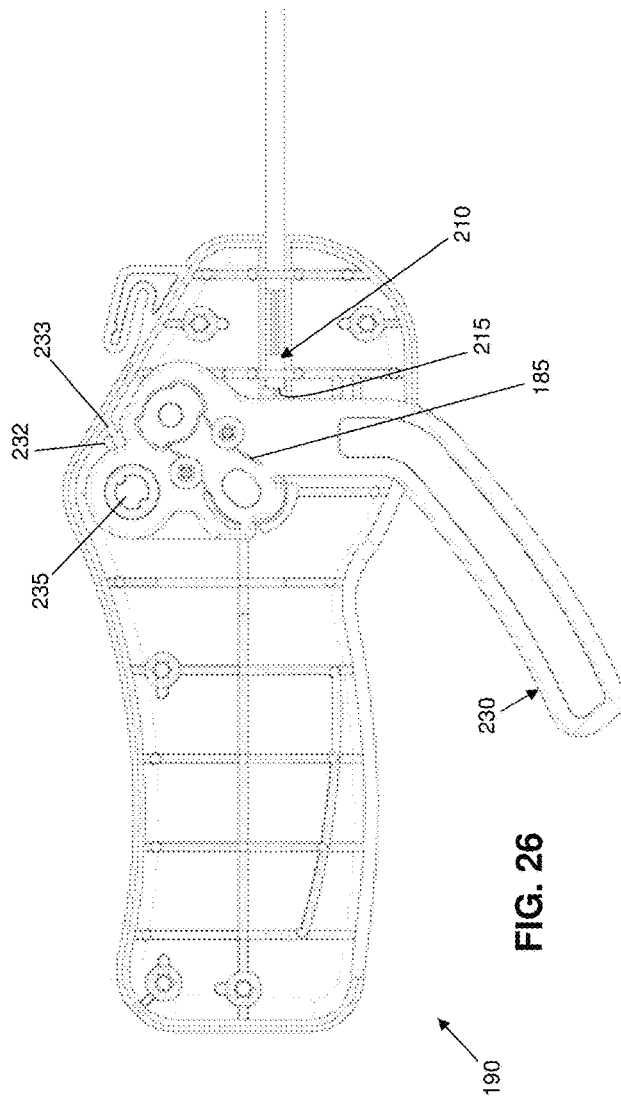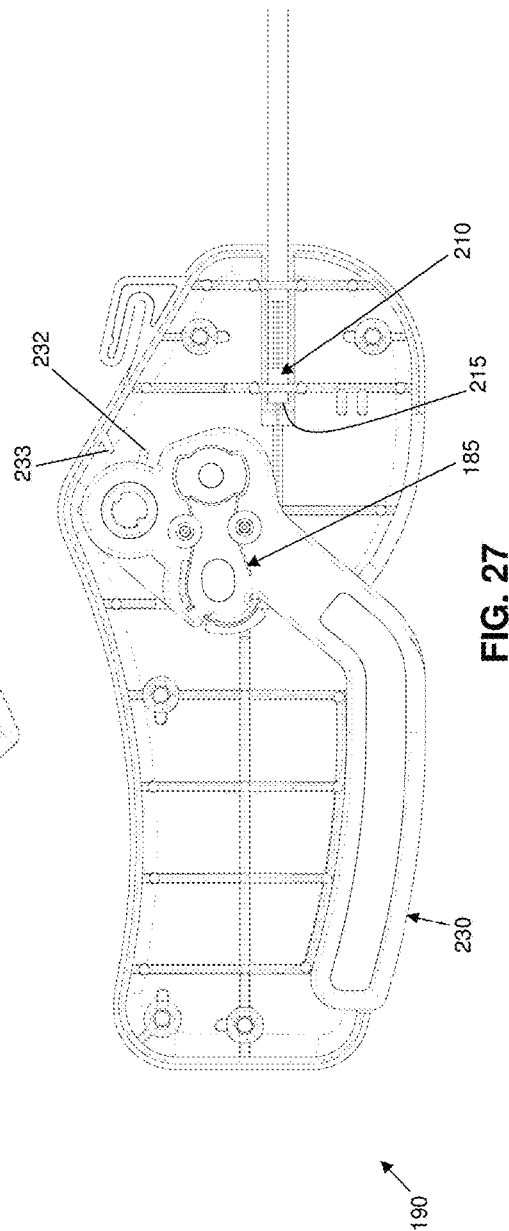

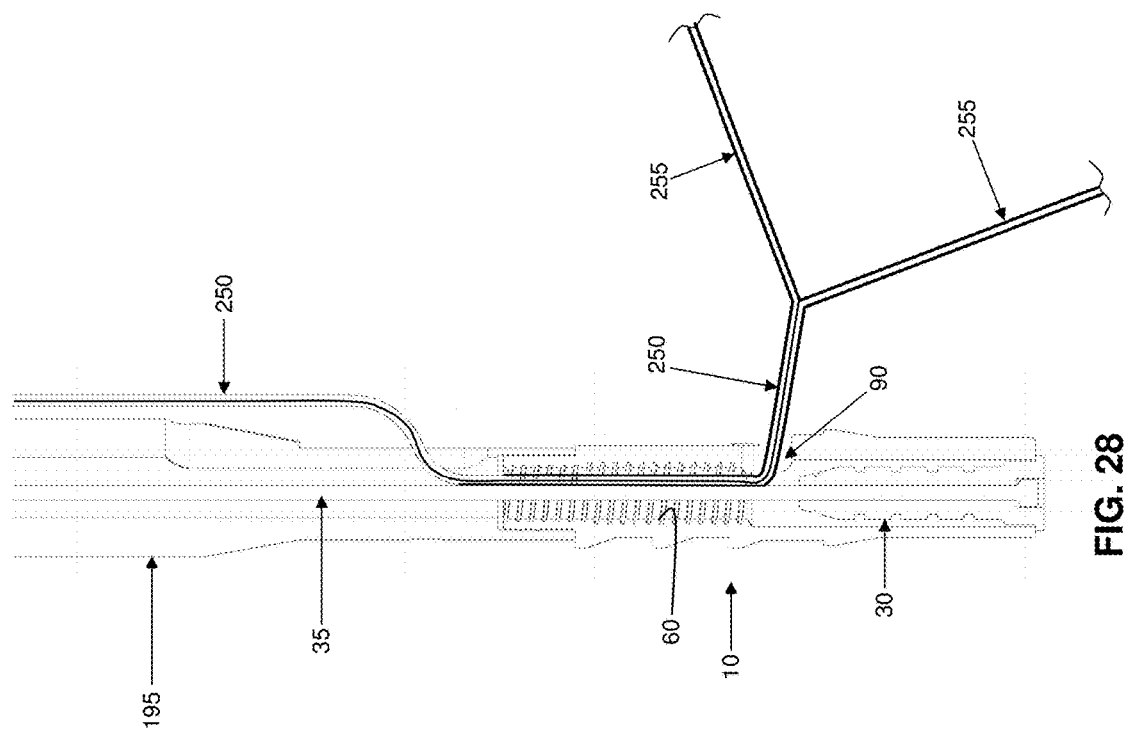

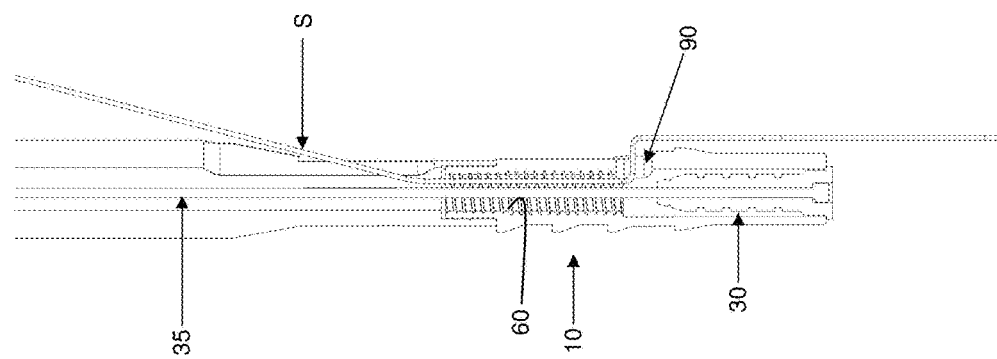

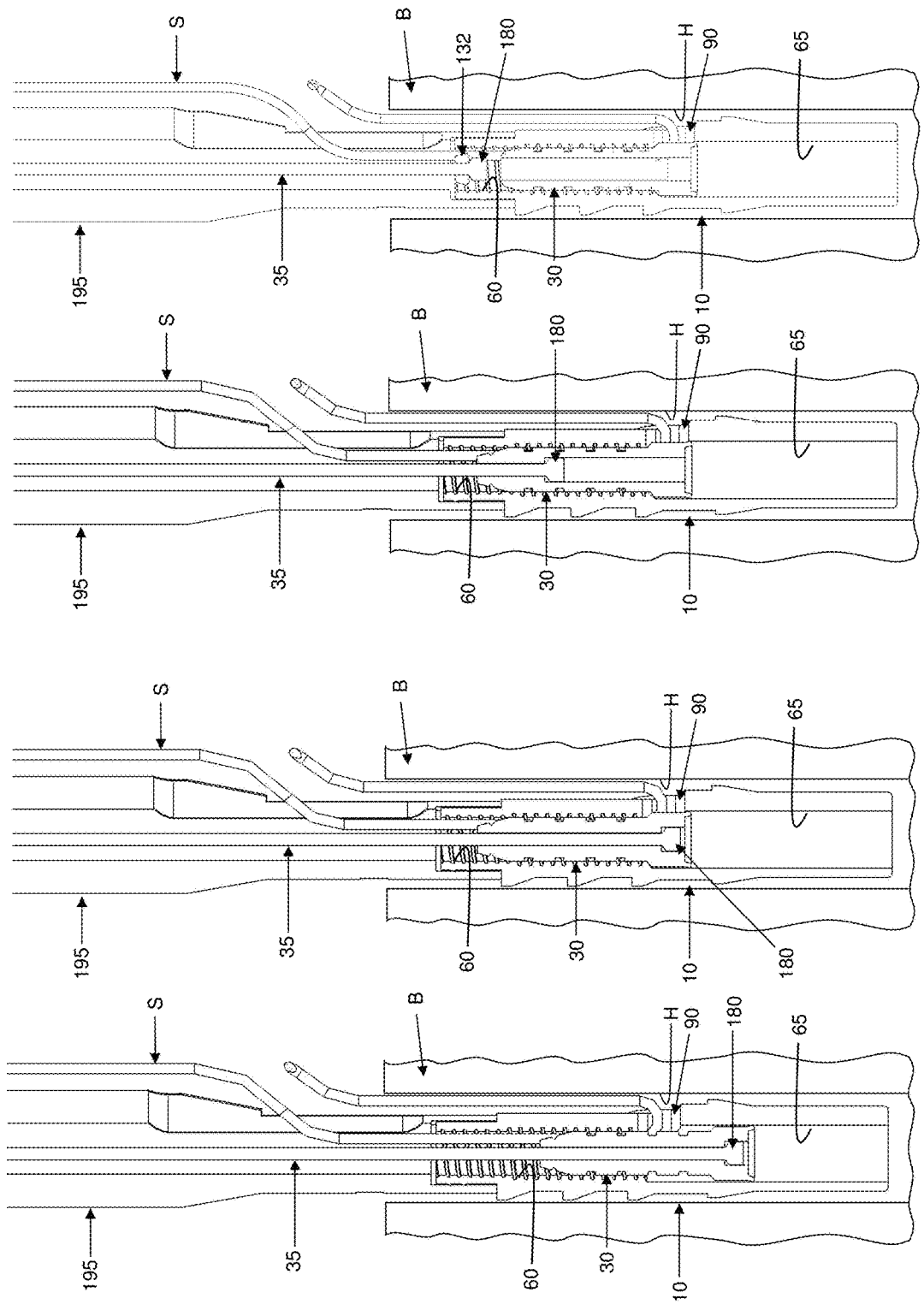

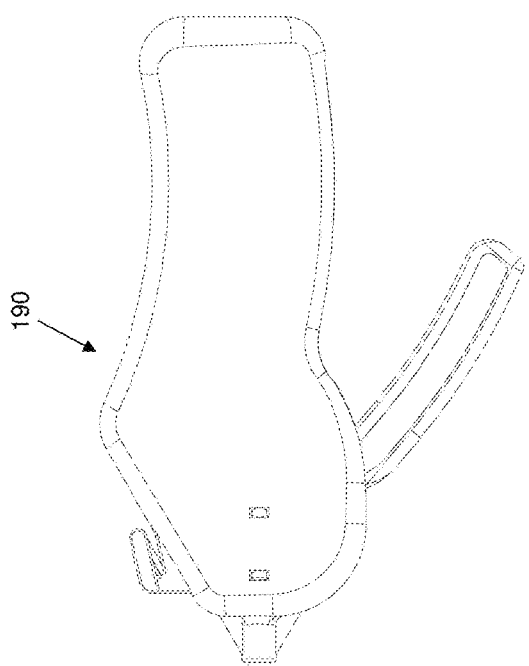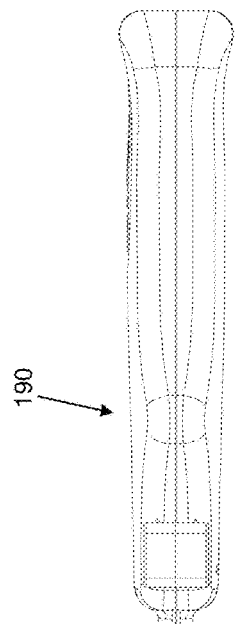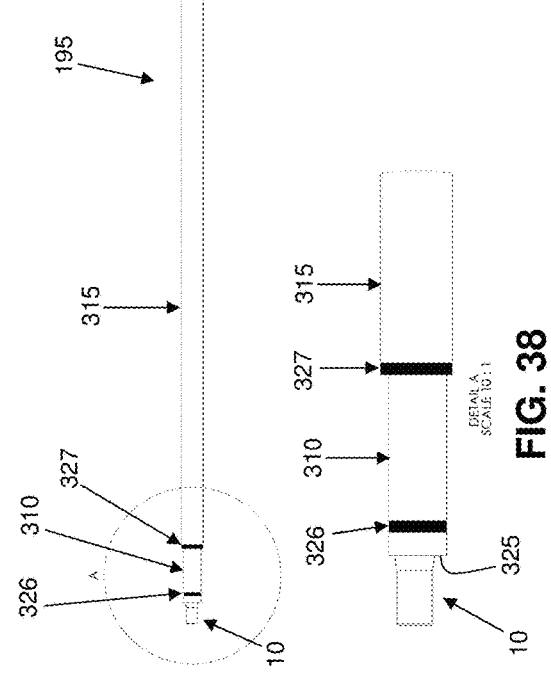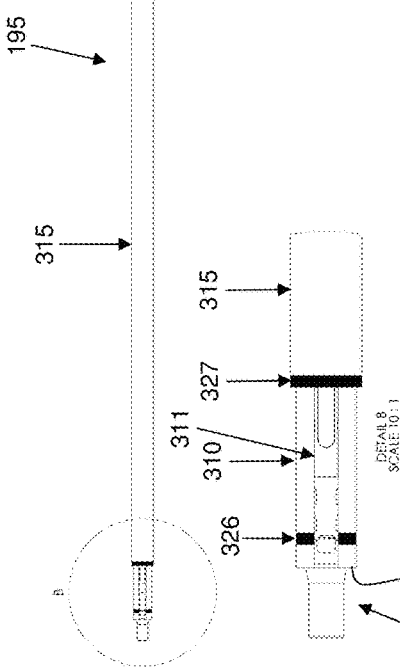
FIG. 37
FIG. 38
FIG. 39
FIG. 40

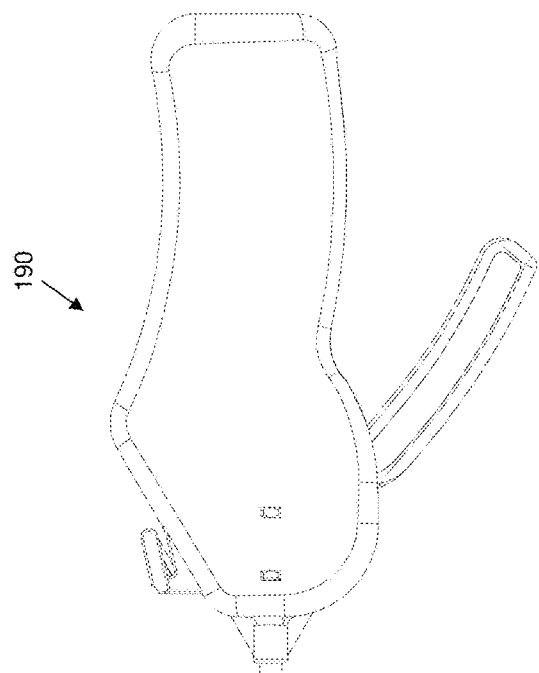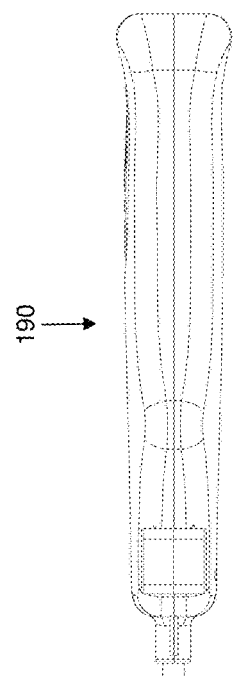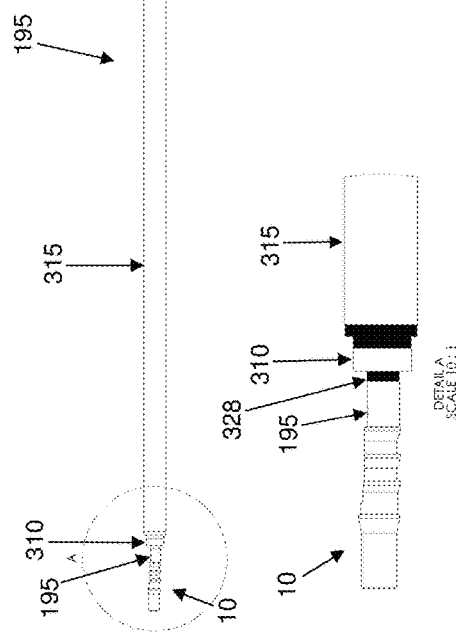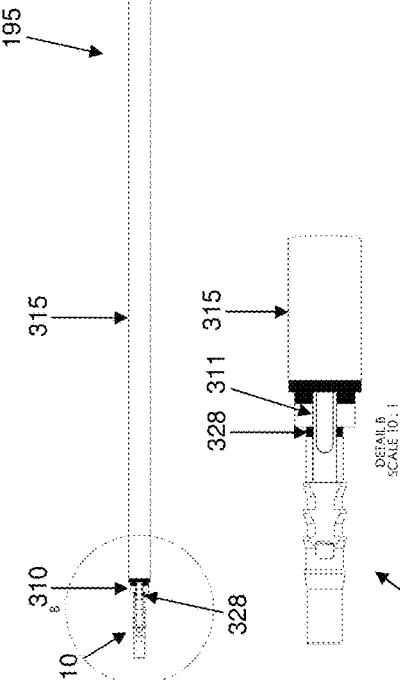
FIG. 43
FIG. 44
FIG. 45
FIG. 46

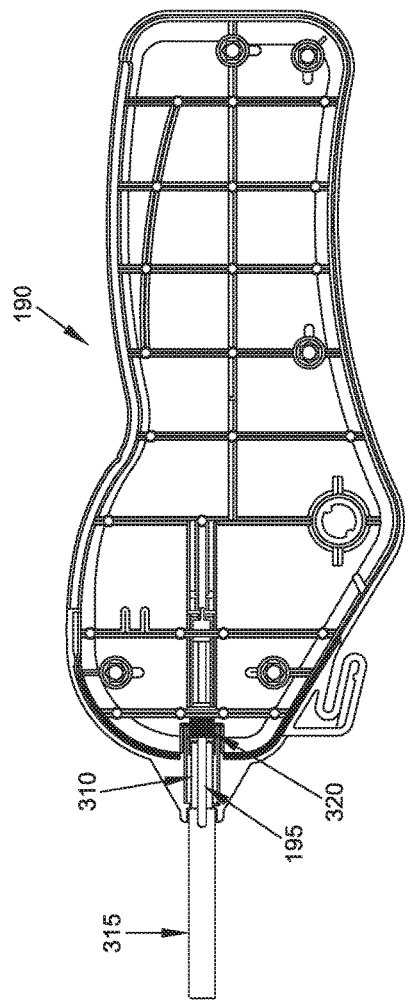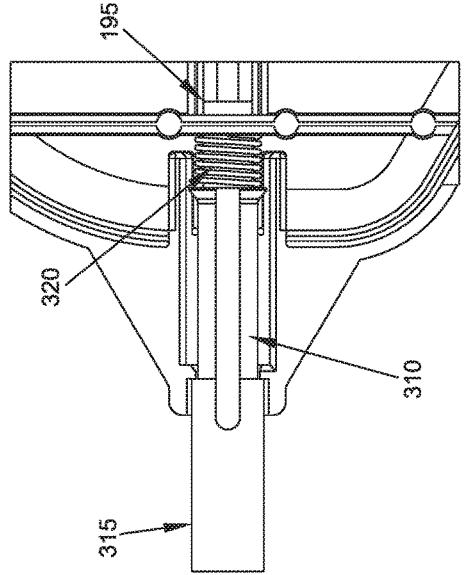
FIG. 47
FIG. 48

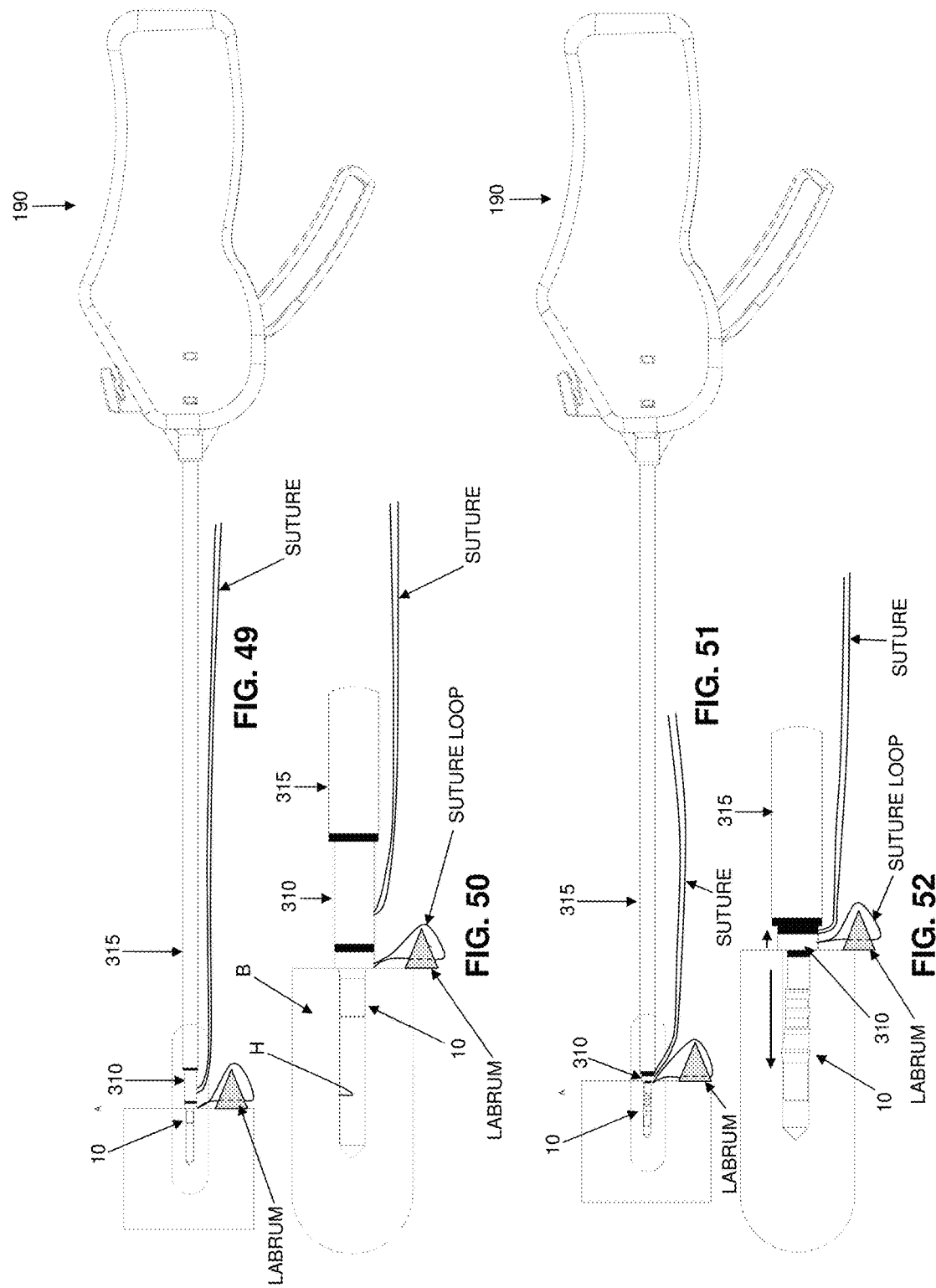

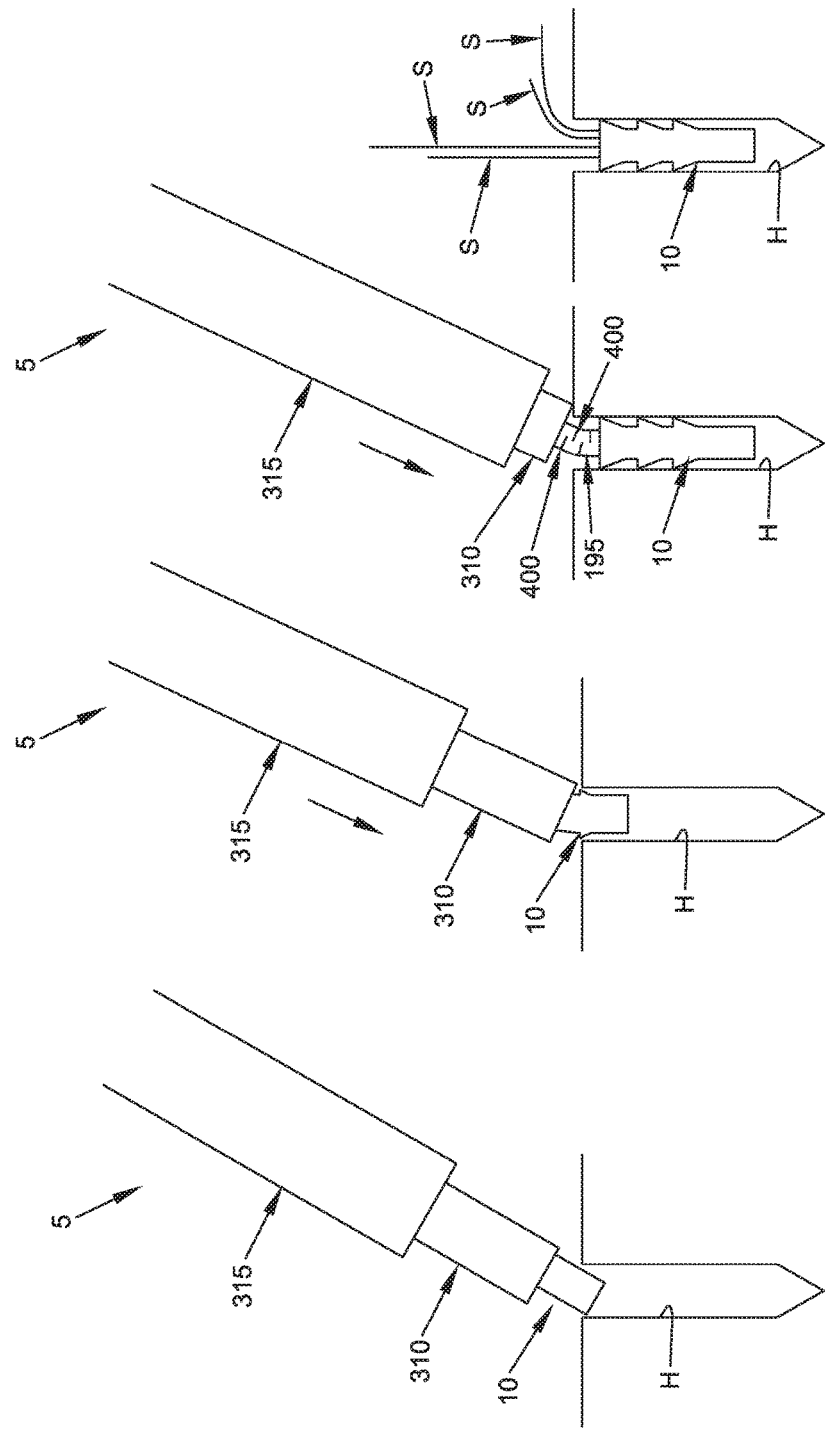

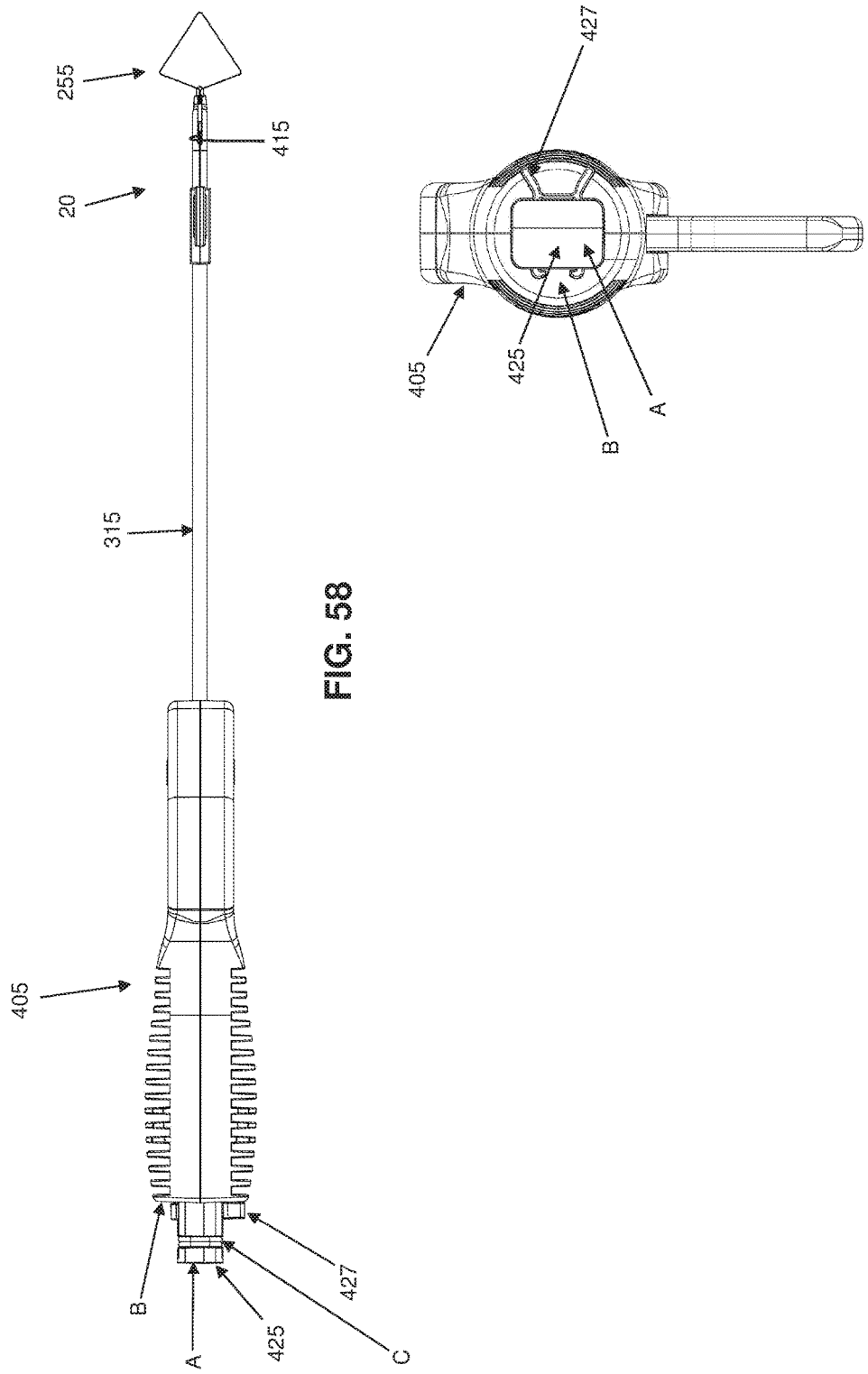

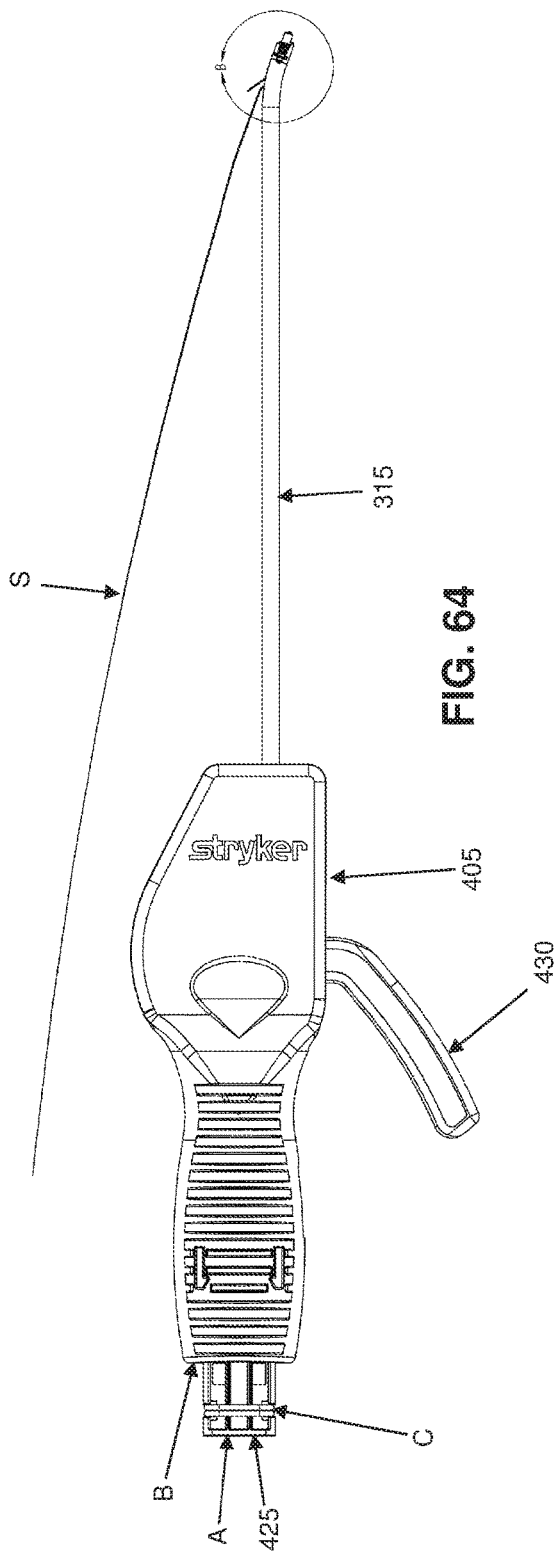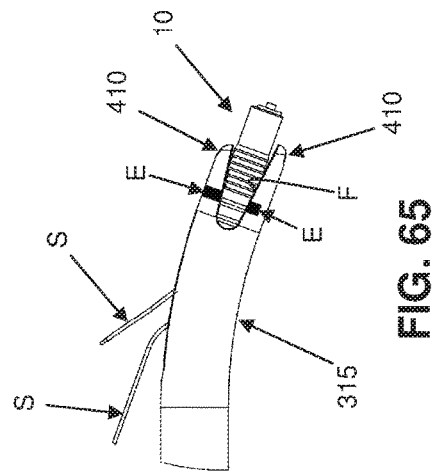

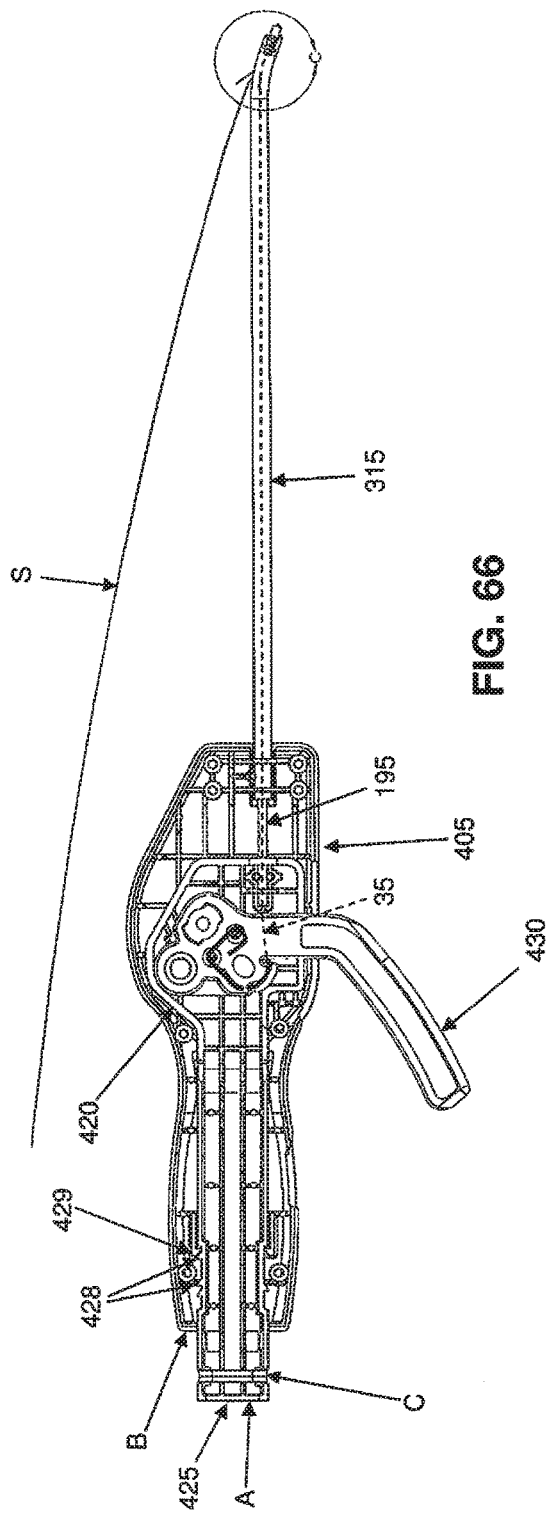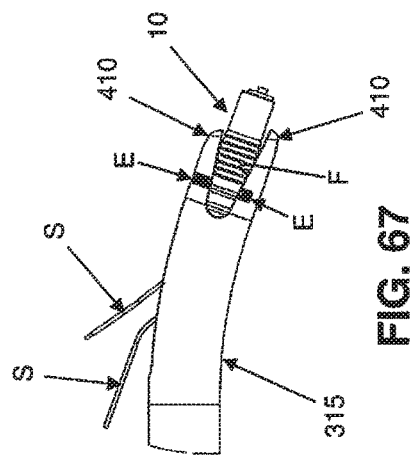

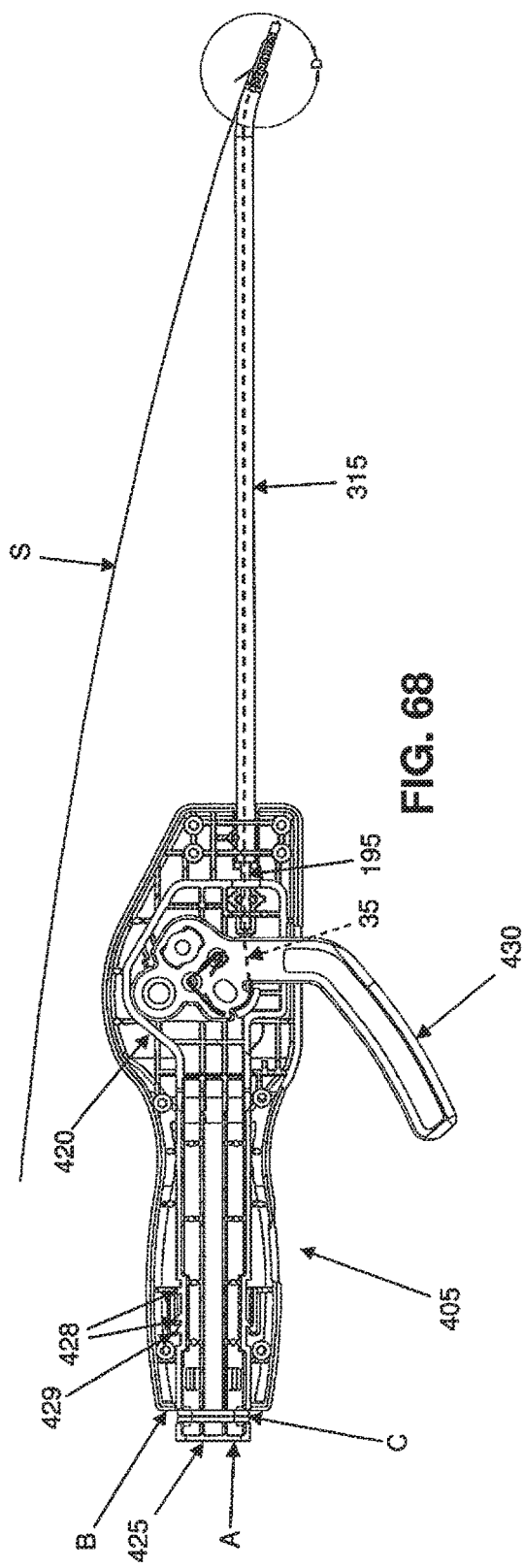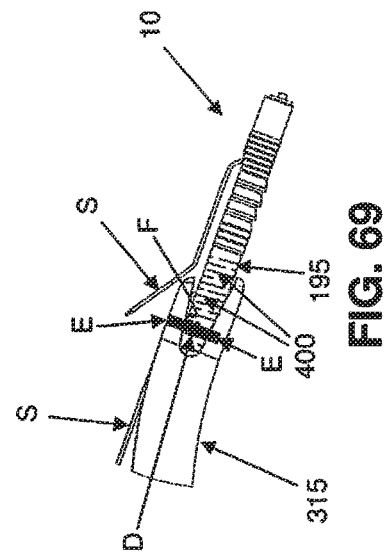

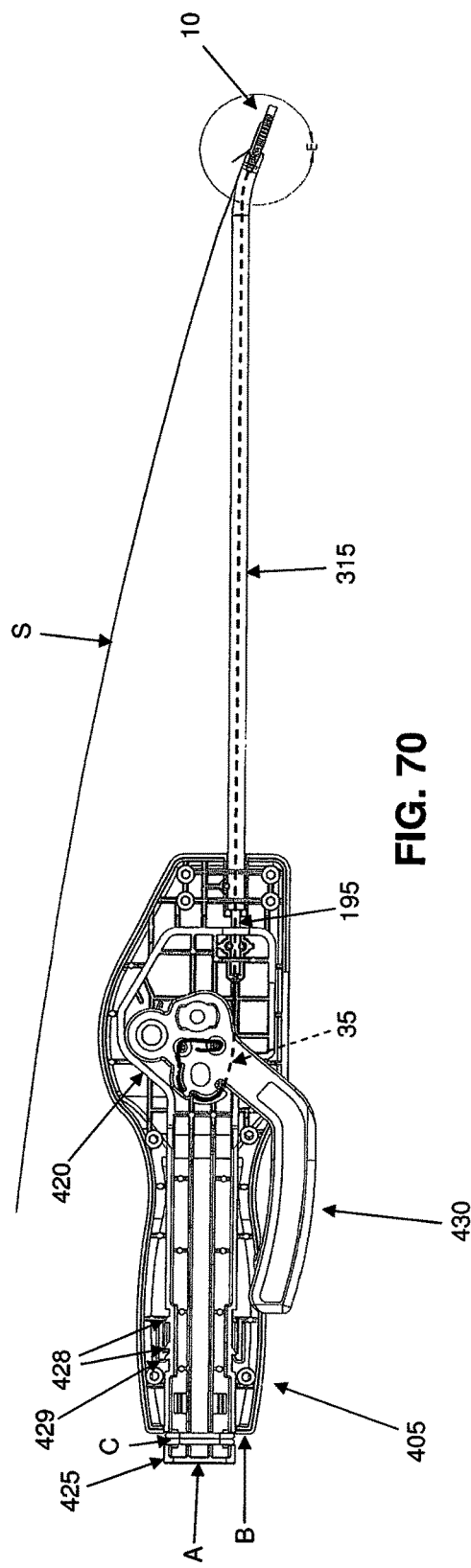
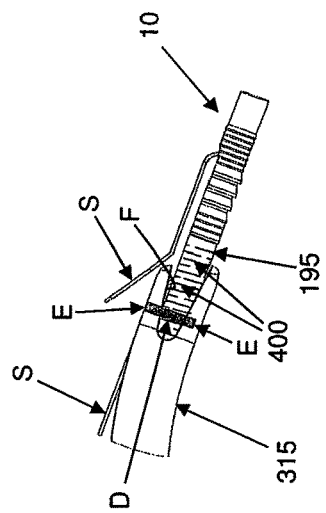
FIG. 70
FIG. 71

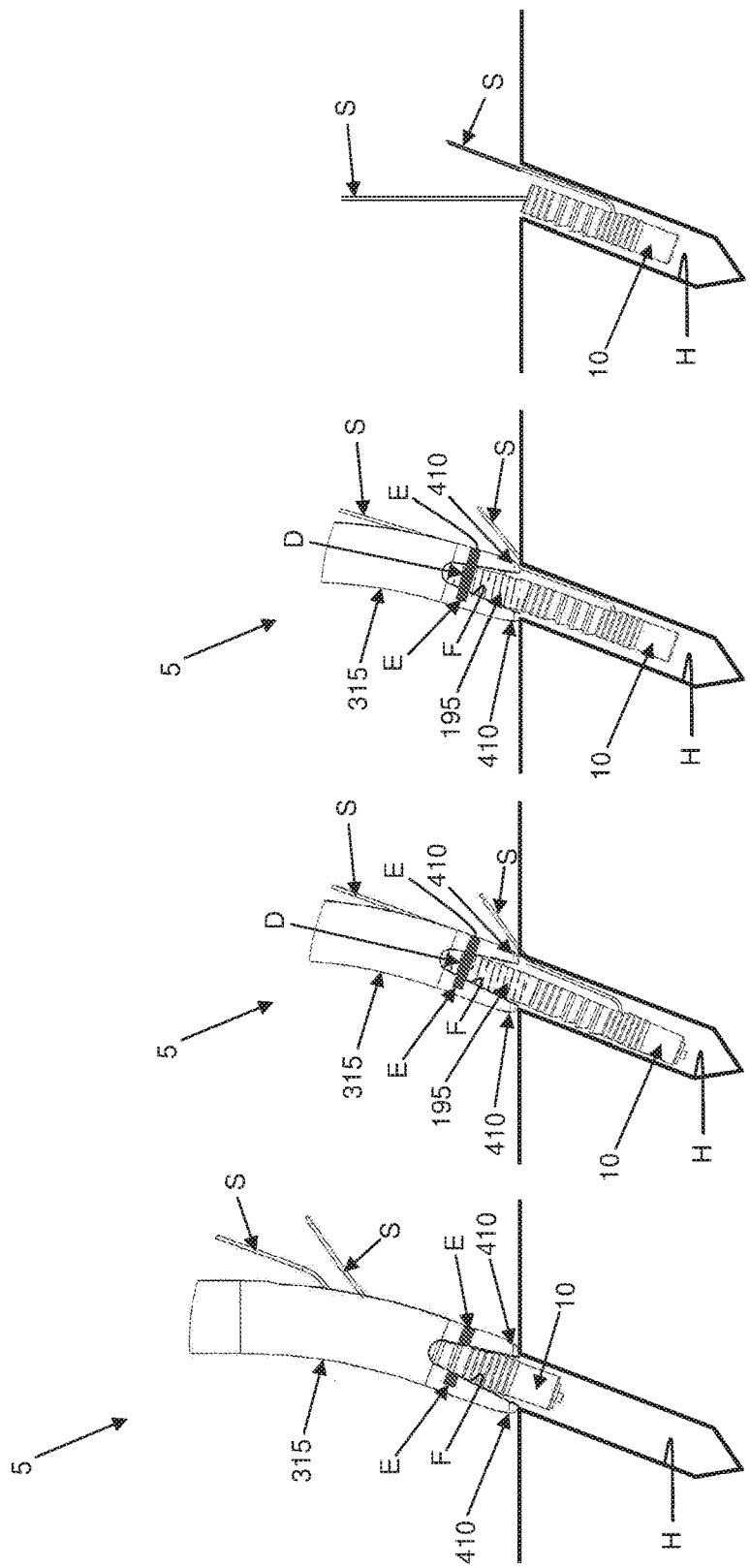

METHOD AND APPARATUS FOR ATTACHING TISSUE TO BONE, INCLUDING THE PROVISION AND USE OF A NOVEL KNOTLESS SUTURE ANCHOR SYSTEM

REFERENCE TO PENDING PRIOR PATENT APPLICATIONS

This patent application:

(1) is a continuation-in-part of pending prior U.S. patent application Ser. No. 14/568,805, filed Dec. 12, 2014 by Pivot Medical, Inc. and Jeremy Graul et al. for METHOD AND APPARATUS FOR ATTACHING TISSUE TO BONE, INCLUDING THE PROVISION AND USE OF A NOVEL KNOTLESS SUTURE ANCHOR SYSTEM, which patent application in turn:

(A) is a continuation-in-part of prior U.S. patent application Ser. No. 13/830,501, filed Mar. 14, 2013 by Pivot Medical, Inc. and Jeremy Graul et al. for METHOD AND APPARATUS FOR ATTACHING TISSUE TO BONE, INCLUDING THE PROVISION AND USE OF A NOVEL KNOTLESS SUTURE ANCHOR SYSTEM, which patent application in turn:

(i) is a continuation-in-part of pending prior U.S. patent application Ser. No. 13/642,168, filed Dec. 26, 2012 by Chris Pamichev et al. for METHOD AND APPARATUS FOR RE-ATTACHING THE LABRUM TO THE ACETABULUM, INCLUDING THE PROVISION AND USE OF A NOVEL SUTURE ANCHOR SYSTEM, which patent application in turn claims benefit of:

(a) prior International (PCT) Patent Application No. PCT/US2011/021173, filed Jan. 13, 2011 by Pivot Medical, Inc. and Chris Pamichev et al. for METHOD AND APPARATUS FOR RE-ATTACHING THE LABRUM TO THE ACETABULUM, INCLUDING THE PROVISION AND USE OF A NOVEL SUTURE ANCHOR SYSTEM, which in turn claims benefit of:

(1) prior U.S. Provisional Patent Application Ser. No. 61/326,709, filed Apr. 22, 2010 by Chris Pamichev et al. for METHOD AND APPARATUS FOR RE-SECURING THE LABRUM TO THE ACETABULUM, INCLUDING THE PROVISION AND USE OF A NOVEL SUTURE ANCHOR SYSTEM; and (2) prior U.S. patent application Ser. No. 12/839,246, filed Jul. 19, 2010 by Chris Pamichev et al. for METHOD AND APPARATUS FOR RE-ATTACHING THE LABRUM TO THE ACETABULUM, INCLUDING THE PROVISION AND USE OF A NOVEL SUTURE ANCHOR SYSTEM, which in turn claims benefit of:

(A) prior U.S. Provisional Patent Application Ser. No. 61/271,205, filed Jul. 17, 2009 by Chris Pamichev et al. for METHOD AND APPARATUS FOR RE-SECURING THE LABRUM TO THE ACETABULUM, INCLUDING THE PROVISION AND USE OF A NOVEL NANO TACK SYSTEM; and (B) prior U.S. Provisional Patent Application Ser. No. 61/326,709, filed Apr. 22, 2010 by Chris Pamichev et al. for METHOD AND APPARATUS FOR RE-SECURING THE LABRUM TO THE ACETABULUM, INCLUDING THE PROVISION AND USE OF A NOVEL SUTURE ANCHOR SYSTEM;

(ii) is a continuation-in-part of prior U.S. patent application Ser. No. 13/538,378, filed Jun. 29, 2012 by Andrew Lantz et al. for METHOD AND APPARATUS FOR RE-ATTACHING THE LABRUM TO THE ACETABULUM, INCLUDING THE PROVISION AND USE OF A NOVEL SUTURE ANCHOR SYSTEM, which patent application in turn claims benefit of prior U.S. Provisional Patent Application Ser. No. 61/502,621, filed Jun. 29, 2011 by Andrew Lantz et al. for FORCE-LIMITING (FORCE-CONTROLLING) DELIVERY MECHANISMS FOR THE CONTROLLED DELIVERY OF THE SUTURE ANCHOR;

(iii) claims benefit of prior U.S. Provisional Patent Application Ser. No. 61/644,129, filed May 8, 2012 by Jeremy Graul et al. for METHOD AND APPARATUS FOR RE-ATTACHING THE LABRUM TO THE ACETABULUM, INCLUDING THE PROVISION AND USE OF A NOVEL SUTURE ANCHOR SYSTEM; and (iv) claims benefit of prior U.S. Provisional Patent Application Ser. No. 61/718,997, filed Oct. 26, 2012 by Pivot Medical, Inc. and Jeremy Graul et al. for METHOD AND APPARATUS FOR RE-ATTACHING THE LABRUM TO THE ACETABULUM, INCLUDING THE PROVISION AND USE OF A NOVEL SUTURE ANCHOR SYSTEM; and (B) claims benefit of prior U.S. Provisional Patent Application Ser. No. 61/915,004, filed Dec. 12, 2013 by Pivot Medical, Inc. and Jeremy Graul for METHOD AND APPARATUS FOR ATTACHING TISSUE TO BONE, INCLUDING THE PROVISION AND USE OF A NOVEL KNOTLESS SUTURE ANCHOR SYSTEM; and (2) claims benefit of prior U.S. Provisional Patent Application Ser. No. 62/201,627, filed Aug. 6, 2015 by Pivot Medical, Inc. and Jeremy Graul et al. for METHOD AND APPARATUS FOR ATTACHING TISSUE TO BONE, INCLUDING THE PROVISION AND USE OF A NOVEL KNOTLESS SUTURE ANCHOR SYSTEM.

The thirteen (13) above-identified patent applications are hereby incorporated herein by reference.

FIELD OF THE INVENTION

This invention relates to surgical methods and apparatus in general, and more particularly to surgical methods and apparatus for treating a hip joint and other anatomy.

BACKGROUND OF THE INVENTION

The Hip Joint in General

The hip joint is a ball-and-socket joint which movably connects the leg to the torso. The hip joint is capable of a wide range of different motions, e.g., flexion and extension, abduction and adduction, medial and lateral rotation, etc. See FIGS. 1A, 1B, 1C and 1D.

With the possible exception of the shoulder joint, the hip joint is perhaps the most mobile joint in the body. Significantly, and unlike the shoulder joint, the hip joint carries substantial weight loads during most of the day, in both static (e.g., standing and sitting) and dynamic (e.g., walking and running) conditions.

The hip joint is susceptible to a number of different pathologies. These pathologies can have both congenital and injury-related origins. In some cases, the pathology can be substantial at the outset. In other cases, the pathology may be minor at the outset but, if left untreated, may worsen over time. More particularly, in many cases, an existing pathology may be exacerbated by the dynamic nature of the hip joint and the substantial weight loads imposed on the hip joint.

The pathology may, either initially or thereafter, significantly interfere with patient comfort and lifestyle. In some cases, the pathology can be so severe as to require partial or total hip replacement. A number of procedures have been developed for treating hip pathologies short of partial or total hip replacement, but these procedures are generally limited in scope due to the significant difficulties associated with treating the hip joint.

A better understanding of various hip joint pathologies, and also the current limitations associated with their treatment, can be gained from a more thorough understanding of the anatomy of the hip joint.

Anatomy of the Hip Joint

The hip joint is formed at the junction of the leg and the torso. More particularly, and looking now at FIG. 2, the head of the femur is received in the acetabular cup of the hip, with a plurality of ligaments and other soft tissue serving to hold the bones in articulating relation.

More particularly, and looking now at FIG. 3, the femur is generally characterized by an elongated body terminating, at its top end, in an angled neck which supports a hemispherical head (also sometimes referred to as "the ball"). As seen in FIGS. 3 and 4, a large projection known as the greater trochanter protrudes laterally and posteriorly from the elongated body adjacent to the neck of the femur. A second, somewhat smaller projection known as the lesser trochanter protrudes medially and posteriorly from the elongated body adjacent to the neck. An intertrochanteric crest (FIGS. 3 and 4) extends along the periphery of the femur, between the greater trochanter and the lesser trochanter.

Looking next at FIG. 5, the hip socket is made up of three constituent bones: the ilium, the ischium and the pubis. These three bones cooperate with one another (they typically ossify into a single "hip bone" structure by the age of 25 or so) in order to collectively form the acetabular cup. The acetabular cup receives the head of the femur.

Both the head of the femur and the acetabular cup are covered with a layer of articular cartilage which protects the underlying bone and facilitates motion. See FIG. 6.

Various ligaments and soft tissue serve to hold the ball of the femur in place within the acetabular cup. More particularly, and looking now at FIGS. 7 and 8, the ligamentum teres extends between the ball of the femur and the base of the acetabular cup. As seen in FIGS. 8 and 9, a labrum is disposed about the perimeter of the acetabular cup. The labrum serves to increase the depth of the acetabular cup and effectively establishes a suction seal between the ball of the femur and the rim of the acetabular cup, thereby helping to hold the head of the femur in the acetabular cup. In addition to the foregoing, and looking now at FIG. 10, a fibrous capsule extends between the neck of the femur and the rim of the acetabular cup, effectively sealing off the ball-and-socket members of the hip joint from the remainder of the body. The foregoing structures (i.e., the ligamentum teres, the labrum and the fibrous capsule) are encompassed and reinforced by a set of three main ligaments (i.e., the iliofemoral ligament, the ischiofemoral ligament and the pubofemoral ligament) which extend between the femur and the perimeter of the hip socket. See, for example, FIGS. 11 and 12, which show the iliofemoral ligament, with FIG. 11 being an anterior view and FIG. 12 being a posterior view.

Pathologies of the Hip Joint

As noted above, the hip joint is susceptible to a number of different pathologies. These pathologies can have both congenital and injury-related origins.

By way of example but not limitation, one important type of congenital pathology of the hip joint involves impingement between the neck of the femur and the rim of the acetabular cup. In some cases, and looking now at FIG. 13, this impingement can occur due to irregularities in the geometry of the femur. This type of impingement is sometimes referred to as cam-type femoroacetabular impingement (i.e., cam-type FAI). In other cases, and looking now at FIG. 14, the impingement can occur due to irregularities in the geometry of the acetabular cup. This latter type of impingement is sometimes referred to as pincer-type femoroacetabular impingement (i.e., pincer-type FAI). Impingement can result in a reduced range of motion, substantial pain and, in some cases, significant deterioration of the hip joint.

By way of further example but not limitation, another important type of congenital pathology of the hip joint involves defects in the articular surface of the ball and/or the articular surface of the acetabular cup. Defects of this type sometimes start out fairly small but often increase in size over time, generally due to the dynamic nature of the hip joint and also due to the weight-bearing nature of the hip joint. Articular defects can result in substantial pain, induce and/or exacerbate arthritic conditions and, in some cases, cause significant deterioration of the hip joint.

By way of further example but not limitation, one important type of injury-related pathology of the hip joint involves trauma to the labrum. More particularly, in many cases, an accident or sports-related injury can result in the labrum being torn away from the rim of the acetabular cup, typically with a tear running through the body of the labrum. See FIG. 15. These types of labral injuries can be very painful for the patient and, if left untreated, can lead to substantial deterioration of the hip joint.

The General Trend Toward Treating Joint Pathologies Using Minimally-Invasive, and Earlier, Interventions The current trend in orthopedic surgery is to treat joint pathologies using minimally-invasive techniques. Such minimally-invasive, "keyhole" surgeries generally offer numerous advantages over traditional, "open" surgeries, including reduced trauma to tissue, less pain for the patient, faster recuperation times, etc.

By way of example but not limitation, it is common to re-attach ligaments in the shoulder joint using minimally-invasive, "keyhole" techniques which do not require large incisions into the interior of the shoulder joint. By way of further example but not limitation, it is common to repair torn meniscal cartilage in the knee joint, and/or to replace ruptured ACL ligaments in the knee joint, using minimally-invasive techniques.

While such minimally-invasive approaches can require additional training on the part of the surgeon, such procedures generally offer substantial advantages for the patient and have now become the standard of care for many shoulder joint and knee joint pathologies.

In addition to the foregoing, in view of the inherent advantages and widespread availability of minimally-invasive approaches for treating pathologies of the shoulder joint and knee joint, the current trend is to provide such treatment much earlier in the lifecycle of the pathology, so as to address patient pain as soon as possible and so as to minimize any exacerbation of the pathology itself. This is in marked contrast to traditional surgical practices, which have generally dictated postponing surgical procedures as long as possible so as to spare the patient from the substantial trauma generally associated with invasive surgery.

Treatment for Pathologies of the Hip Joint

Unfortunately, minimally-invasive treatments for pathologies of the hip joint have lagged far behind minimally-invasive treatments for pathologies of the shoulder joint and the knee joint. This is generally due to (i) the constrained geometry of the hip joint itself, and (ii) the nature and location of the pathologies which must typically be addressed in the hip joint.

More particularly, the hip joint is generally considered to be a "tight" joint, in the sense that there is relatively little room to maneuver within the confines of the joint itself. This is in marked contrast to the shoulder joint and the knee joint, which are generally considered to be relatively "spacious" joints (at least when compared to the hip joint). As a result, it is relatively difficult for surgeons to perform minimally-invasive procedures on the hip joint.

Furthermore, the pathways for entering the interior of the hip joint (i.e., the natural pathways which exist between adjacent bones and/or delicate neurovascular structures) are generally much more constraining for the hip joint than for the shoulder joint or the knee joint. This limited access further complicates effectively performing minimally-invasive procedures on the hip joint.

In addition to the foregoing, the nature and location of the pathologies of the hip joint also complicate performing minimally-invasive procedures on the hip joint. By way of example but not limitation, consider a typical detachment of the labrum in the hip joint. In this situation, instruments must generally be introduced into the joint space using an angle of approach which is offset from the angle at which the instrument addresses the tissue. This makes drilling into bone, for example, significantly more complicated than where the angle of approach is effectively aligned with the angle at which the instrument addresses the tissue, such as is frequently the case in the shoulder joint. Furthermore, the working space within the hip joint is typically extremely limited, further complicating repairs where the angle of approach is not aligned with the angle at which the instrument addresses the tissue.

As a result of the foregoing, minimally-invasive hip joint procedures are still relatively difficult to perform and hence less common in practice. Consequently, many patients are forced to manage their hip pain for as long as possible, until a resurfacing procedure or a partial or total hip replacement procedure can no longer be avoided. These procedures are generally then performed as a highly-invasive, open procedure, with all of the disadvantages associated with highly-invasive, open procedures.

As a result, there is, in general, a pressing need for improved methods and apparatus for treating pathologies of the hip joint.

Re-Attaching the Labrum of the Hip Joint

As noted above, hip arthroscopy is becoming increasingly more common in the diagnosis and treatment of various hip pathologies. However, due to the anatomy of the hip joint and the pathologies associated with the same, hip arthroscopy is currently practical for only selected pathologies and, even then, hip arthroscopy has generally met with limited success.

One procedure which is sometimes attempted arthroscopically relates to the repair of a torn and/or detached labrum. This procedure may be attempted when the labrum has been damaged but is still sufficiently healthy and capable of repair. The repair can occur with a labrum which is still attached to the acetabulum or after the labrum has been deliberately detached from the acetabulum (e.g., so as to allow for acetabular rim trimming to treat a pathology such as a pincer-type FAI) and needs to be subsequently re-attached. See, for example, FIG. 16, which shows a normal labrum which has its base securely attached to the acetabulum, and FIG. 17, which shows a portion of the labrum (in this case the tip) detached from the acetabulum. In this respect it should also be appreciated that repairing the labrum rather than removing the labrum is generally desirable, inasmuch as studies have shown that patients whose labrum has been repaired tend to have better long-term outcomes than patients whose labrum has been removed.

Unfortunately, current methods and apparatus for arthroscopically repairing (e.g., re-attaching) the labrum are somewhat problematic. The present invention is intended to improve upon the current approaches for labrum repair.

More particularly, current approaches for arthroscopically repairing the labrum typically use apparatus originally designed for use in re-attaching ligaments to bone. For example, one such approach utilizes a screw-type anchor, with two lengths of suture extending therefrom, and involves deploying the anchor in the acetabulum above the labrum
re-attachment site. After the anchor has been deployed, one length of suture is passed either through the detached labrum or, alternatively, around the detached labrum. Then that length of suture is tied to the other length of suture so as to secure the labrum against the acetabular rim. See FIG. 18.

Unfortunately, suture anchors of the sort described above are traditionally used for re-attaching ligaments to bone and, as a result, tend to be relatively large, since they must carry the substantial pull-out forces normally associated with ligament reconstruction. However, this large anchor size is generally unnecessary for labrum re-attachment, since the labrum is not subjected to substantial forces, and the large anchor size typically causes unnecessary trauma to the patient.

Furthermore, the large size of traditional suture anchors can be problematic when the anchors are used for labrum re-attachment, since the suture anchors generally require a substantial bone mass for secure anchoring, and such a large bone mass is generally available only a substantial distance up the acetabular shelf. In addition, the large size of the suture anchors generally makes it necessary to set the suture anchor a substantial distance up the acetabular shelf, in order to ensure that the distal tip of the suture anchor does not inadvertently break through the acetabular shelf and contact the articulating surfaces of the joint. However, labral re-attachment utilizing a suture anchor set high up into the acetabular shelf creates a suture path, and hence a labral draw force, which is not directly aligned with the portion of the acetabular rim where the labrum is to be re-attached. As a result, an "indirect" draw force (also known as "eversion") is typically applied to the labrum, i.e., the labrum is drawn around the rim of the acetabulum rather than directly into the acetabulum. See FIG. 18. This can sometimes result in a problematic labral re-attachment and, ultimately, can lead to a loss of the suction seal between the labrum and femoral head, which is a desired outcome of the labral re-attachment procedure. Using suture anchors of a smaller size allows the suture anchor to be set closer to the rim of the acetabulum, which can help reduce this effect. See FIG. 18A.

In addition to the foregoing, suture anchors of the sort described above require that a knot be tied at the surgical site in order to secure the labrum to the acetabulum. This can be time-consuming and inconvenient to effect. More particularly, and as noted above, the suture anchor typically has a suture connected thereto so that two lengths of suture extend from the suture anchor and are available to secure the labrum to the acetabulum (which receives the suture anchor). One or both of the two lengths of suture are passed through or around the labrum and then knotted to one another so as to secure the labrum to the acetabulum. However, it can be time-consuming and inconvenient to form the knot at the surgical site, given the limited access to the surgical site and the restricted work space at the surgical site.

Accordingly, a new approach is needed for arthroscopically re-attaching the labrum to the acetabulum.

SUMMARY OF THE INVENTION

The present invention provides a novel method and apparatus for re-attaching the labrum to the acetabulum.

Among other things, the present invention provides a novel knotless suture anchor system which may be used to re-attach the labrum to the acetabulum, and/or to attach other tissue to bone.

In one preferred form of the present invention, there is provided a knotless suture anchor wherein a loop of suture is passed through the labrum (or other tissue) and its two free ends are slidably connected (e.g., slidably threaded through) the knotless suture anchor. After the knotless suture anchor is advanced into the acetabulum (or other bone) and the loop of suture is tensioned so as to hold the labrum (or other tissue) in place against the acetabulum (or other bone), the knotless suture anchor is reconfigured so as to lock the loop of suture to the knotless suture anchor and hence secure the labrum (or other tissue) to the acetabulum (or other bone).

In one form of the present invention, there is provided apparatus for securing a first object to a second object, the apparatus comprising:

an elongated body having a distal end, a proximal end, and a lumen extending between the distal end and the proximal end, the lumen comprising a distal section and a proximal section, the distal section of the lumen having a wider diameter than the proximal section of the lumen;

a window extending through the side wall of the elongated body and communicating with the lumen, the window being disposed in the vicinity of the intersection between the distal section of the lumen and the proximal section of the lumen and being sized to receive a first object therein;

an elongated element extending through the lumen of the elongated body, the elongated element comprising a proximal end and a distal end; and a locking element mounted to the distal end of the elongated element and disposed in the distal section of the lumen;

whereby, when the elongated body is disposed in a second object, and a first object extends through the window, and the locking element is thereafter moved proximally, proximal movement of the locking element causes the elongated body to capture the first object to the elongated body, whereby to secure the first object to the second object.

In another form of the present invention, there is provided apparatus for securing a first object to a second object, the apparatus comprising:

an elongated body having a distal end, a proximal end, and a lumen extending between the distal end and the proximal end;

a window extending through the side wall of the elongated body and communicating with the lumen, the window being sized to receive a first object therein;

a locking element disposed in the lumen, the locking element having a larger proximal end and a smaller distal end;

whereby, when the elongated body is disposed in a second object, and a first object extends through the window, and the locking element is thereafter moved distally, distal movement of the locking element captures the first object to the elongated body, whereby to secure the first object to the second object.

In another form of the present invention, there is provided a method for securing a first object to a second object, the method comprising:

providing apparatus comprising:

an elongated body having a distal end, a proximal end, and a lumen extending between the distal end and the proximal end, the lumen comprising a distal section and a proximal section, the distal section of the lumen having a wider diameter than the proximal section of the lumen;

a window extending through the side wall of the elongated body and communicating with the lumen, the window being disposed in the vicinity of the intersection between the distal section of the lumen and the proximal section of the lumen and being sized to receive a first object therein;

an elongated element extending through the lumen of the elongated body, the elongated element comprising a proximal end and a distal end; and a locking element mounted to the distal end of the elongated element and disposed in the distal section of the lumen;

extending the first object through the window;

positioning the elongated body in the second object; and moving the locking element proximally, such that proximal movement of the locking element causes the elongated body to capture the first object to the elongated body, whereby to secure the first object to the second object.

In another form of the present invention, there is provided a method for securing a first object to a second object, the method comprising:

providing apparatus comprising:

an elongated body having a distal end, a proximal end, and a lumen extending between the distal end and the proximal end;

a window extending through the side wall of the elongated body and communicating with the lumen, the window being sized to receive a first object therein;

a locking element mounted to the distal end of the elongated element and disposed in the lumen, the locking element having a larger proximal end and a smaller distal end;

extending the first object extends through the window;

positioning the elongated body in the second object; and moving the locking element distally, such that distal movement of the locking element captures the first object to the elongated body, whereby to secure the first object to the second object.

In another form of the present invention, there is provided apparatus for securing an object to bone, said apparatus comprising:
an anchor, said anchor comprising:
a body comprising an opening for receiving a filament therein; and
a locking element movably mounted to said body for selectively locking said filament to said body; and
an inserter for deploying said anchor in bone, said inserter comprising:
a handle;
an overtube extending distally from said handle;
a shaft movably mounted within said overtube and releasably connected to said body of said anchor, said shaft being hollow; and
a rod movably mounted within said shaft and connected to said locking element;
wherein at least a portion of said shaft is flexible.

In another form of the present invention, there is provided apparatus for securing an object to bone, said apparatus comprising:
an anchor, said anchor comprising:
a body comprising an opening for receiving a filament therein; and
a locking element movably mounted to said body for selectively locking said filament to said body; and
an inserter for deploying said anchor in bone, said inserter comprising:
a handle;
an overtube extending distally from said handle;
a carriage movably mounted to said handle;
a shaft movably mounted within said overtube and connected to said carriage and releasably connected to said body of said anchor, said shaft being hollow; and
a rod movably mounted within said shaft and connected to said locking element.

In another form of the present invention, there is provided apparatus for securing an object to bone, said apparatus comprising:
an anchor, said anchor comprising:
a body comprising an opening for receiving a filament therein; and
an inserter for deploying said anchor in bone, said inserter comprising:
a handle;
an overtube extending distally from said handle, wherein the distal end of said overtube is curved;
a carriage movably mounted to said handle; and
a shaft movably mounted within said overtube and connected to said carriage and releasably connected to said body of said anchor, said shaft being hollow and at least a portion of said shaft being flexible.

In another form of the present invention, there is provided a method for securing an object to bone, said method comprising:
providing apparatus comprising:
an anchor, said anchor comprising:
a body comprising an opening for receiving a filament therein; and
a locking element movably mounted to said body for selectively locking said filament to said body; and
an inserter for deploying said anchor in bone, said inserter comprising:
a handle;
an overtube extending distally from said handle;
a shaft movably mounted within said overtube and releasably connected to said body of said anchor, said shaft being hollow; and
a rod movably mounted within said shaft and connected to said locking element;
wherein at least a portion of said shaft is flexible;
forming a hole in the bone; and
using the inserter to insert the anchor into the hole formed in the bone.

In another form of the present invention, there is provided a method for securing an object to bone, said method comprising:
providing apparatus comprising:
an anchor, said anchor comprising:
a body comprising an opening for receiving a filament therein; and
a locking element movably mounted to said body for selectively locking said filament to said body; and
an inserter for deploying said anchor in bone, said inserter comprising:
a handle;
an overtube extending distally from said handle;
a carriage movably mounted to said handle;
a shaft movably mounted within said overtube and connected to said carriage and releasably connected to said body of said anchor, said shaft being hollow; and
a rod movably mounted within said shaft and connected to said locking element;
forming a hole in the bone; and
using the inserter to insert the anchor into the hole formed in the bone.

In another form of the present invention, there is provided a method for securing an object to bone, said method comprising:
providing apparatus comprising:
an anchor, said anchor comprising:
a body comprising an opening for receiving a filament therein; and
an inserter for deploying said anchor in bone, said inserter comprising:
a handle;
an overtube extending distally from said handle, wherein the distal end of said overtube is curved;
a carriage movably mounted to said handle; and
a shaft movably mounted within said overtube and connected to said carriage and releasably connected to said body of said anchor, said shaft being hollow and at least a portion of said shaft being flexible;
forming a hole in the bone; and
using the inserter to insert the anchor into the hole formed in the bone.

In another form of the present invention, there is provided apparatus for securing an object to bone, said apparatus comprising:
an anchor, said anchor comprising:
a body comprising an opening for receiving a filament therein; and
a locking element movably mounted to said body for selectively locking said filament to said body; and
an inserter for deploying said anchor in bone, said inserter comprising:
a handle having a distal end and a proximal end;

an overtube having a distal end and a proximal end, said proximal end of said overtube being mounted to said distal end of said handle;

a slidable carriage movably mounted to said handle for movement between a proximal position and a distal position;

a hollow shaft movably mounted within said overtube, said hollow shaft having a distal end and a proximal end, said proximal end of said hollow shaft being mounted to said slidable carriage and said distal end of said hollow shaft being releasably connected to said body of said anchor;

said slidable carriage comprising a drive head extending out of said proximal end of said handle, such that applying a distal force to said drive head moves said slidable carriage from said proximal position toward said distal position;

a transmission element movably mounted within said hollow shaft, said transmission element having a distal end and a proximal end, said proximal end of said transmission element being mounted to said slidable carriage and said distal end of said transmission element being connected to said locking element of said anchor; and an actuator mounted to said slidable carriage, said proximal end of said transmission element being mounted to said actuator such that said actuator may selectively move said transmission element whereby to move said locking element.

In another form of the present invention, there is provided a method for securing an object to bone, said method comprising:

providing apparatus comprising:
an anchor, said anchor comprising:
a body comprising an opening for receiving a filament therein; and
a locking element movably mounted to said body for selectively locking said filament to said body; and
an inserter for deploying said anchor in bone, said inserter comprising:
a handle having a distal end and a proximal end;
an overtube having a distal end and a proximal end, said proximal end of said overtube being mounted to said distal end of said handle;
a slidable carriage movably mounted to said handle for movement between a proximal position and a distal position;
a hollow shaft movably mounted within said overtube, said hollow shaft having a distal end and a proximal end, said proximal end of said hollow shaft being mounted to said slidable carriage and said distal end of said hollow shaft being releasably connected to said body of said anchor;
said slidable carriage comprising a drive head extending out of said proximal end of said handle, such that applying a distal force to said drive head moves said slidable carriage from said proximal position toward said distal position;
a transmission element movably mounted within said hollow shaft, said transmission element having a distal end and a proximal end, said proximal end of said transmission element being mounted to said slidable carriage and said distal end of said transmission element being connected to said locking element of said anchor; and
an actuator mounted to said slidable carriage, said proximal end of said transmission element being mounted to said actuator such that said actuator may selectively move said transmission element whereby to move said locking element;

forming a hole in the bone; and
using said inserter to insert said anchor into the hole formed in the bone.

In another form of the present invention, there is provided apparatus for securing an object to bone, said apparatus comprising:

an anchor, said anchor comprising:
a body comprising an opening for receiving a filament therein; and
a locking element movably mounted to said body for selectively locking said filament to said body; and
an inserter for deploying said anchor in bone, said inserter comprising:
a handle having a distal end and a proximal end;
an overtube having a distal end and a proximal end, said proximal end of said overtube being mounted to said distal end of said handle;
a slidable carriage movably mounted to said handle for movement between a proximal position and a distal position;
a hollow shaft movably mounted within said overtube, said hollow shaft having a distal end and a proximal end, said proximal end of said hollow shaft being mounted to said slidable carriage and said distal end of said hollow shaft being releasably connected to said body of said anchor;
a transmission element movably mounted within said hollow shaft, said transmission element having a distal end and a proximal end, said proximal end of said transmission element being mounted to said slidable carriage and said distal end of said transmission element being connected to said locking element of said anchor; and
an actuator mounted to said slidable carriage, said proximal end of said transmission element being mounted to said actuator such that said actuator may selectively move said transmission element whereby to move said locking element.

In another form of the present invention, there is provided a method for securing an object to bone, said method comprising:

providing apparatus comprising:
an anchor, said anchor comprising:
a body comprising an opening for receiving a filament therein; and
a locking element movably mounted to said body for selectively locking said filament to said body; and
an inserter for deploying said anchor in bone, said inserter comprising:
a handle having a distal end and a proximal end;
an overtube having a distal end and a proximal end, said proximal end of said overtube being mounted to said distal end of said handle;
a slidable carriage movably mounted to said handle for movement between a proximal position and a distal position;
a hollow shaft movably mounted within said overtube, said hollow shaft having a distal end and a proximal end, said proximal end of said hollow shaft being mounted to said slidable carriage and said distal end of said hollow shaft being releasably connected to said body of said anchor;
a transmission element movably mounted within said hollow shaft, said transmission element having a distal end and a proximal end, said proximal end of said transmission element being mounted to said slidable carriage and said distal end of said transmission element being connected to said locking element of said anchor; and an actuator mounted to said slidable carriage, said proximal end of said transmission element being mounted to said actuator such that said actuator may selectively move said transmission element whereby to move said locking element;

forming a hole in the bone; and using said inserter to insert said anchor into the hole formed in the bone.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 13 is a schematic view showing cam-type femoroacetabular impingement (i.e., cam-type FAI);

FIG. 14 is a schematic view showing pincer-type femoroacetabular impingement (i.e., pincer-type FAI);

FIG. 18A is a schematic view showing another suture anchor being used to re-attach the labrum to the acetabulum;

FIGS. 19 and 20 are schematic views showing a novel knotless suture anchor system formed in accordance with the present invention;

FIGS. 21-25 are schematic views showing the knotless suture anchor of the knotless suture anchor system shown in FIGS. 19 and 20, and the distal end of the inserter of the knotless suture anchor system shown in FIGS. 19 and 20;

FIGS. 26 and 27 are schematic views showing the handle of the inserter of the knotless suture anchor system shown in FIGS. 19 and 20;

FIG. 28 shows portions of the knotless suture anchor system (i.e., the suture anchor, inserter and suture threader) shown in FIGS. 19 and 20;

FIGS. 28A, 29 and 30 show a suture loaded into the knotless suture anchor system shown in FIGS. 19 and 20, wherein FIG. 30 is a cutaway view of FIG. 29;

FIGS. 31-36 are schematic views showing the knotless suture anchor of the knotless suture anchor system shown in FIGS. 19 and 20 securing a suture to bone, wherein FIG. 36 is a cutaway view of FIG. 35;

FIGS. 37-48 are schematic views showing an alternative form of knotless suture anchor system formed in accordance with the present invention, wherein FIGS. 37, 38, 41, 42, 43, 44, 47 and 48 comprise side views, and FIGS. 39, 40, 45 and 46 comprise top views;

FIGS. 49-52 are schematic views showing the knotless suture anchor system of FIGS. 37-48 securing a suture to bone (whereby to secure a labrum to bone);

FIGS. 53-56 are schematic views showing the knotless suture anchor system of FIGS. 37-48, wherein the shaft carrying the knotless suture anchor is formed with a flexible construction (note that suture S is omitted from FIGS. 53-55 for the sake of clarity);

FIGS. 57-71 are schematic views showing another form of knotless suture anchor system formed in accordance with the present invention, wherein the shaft is carried by a slidable inner carriage (note that in FIGS. 66, 68 and 70, the outer shell of the inserter handle is removed in order to expose internal elements of the inserter handle); and FIGS. 72-75 are schematic views showing the knotless suture anchor system of FIGS. 57-71 deploying a knotless suture anchor in bone.

DETAILED DESCRIPTION OF THE PREFERRED EMBODIMENTS

Knotless Suture Anchor System

Figure 1A:
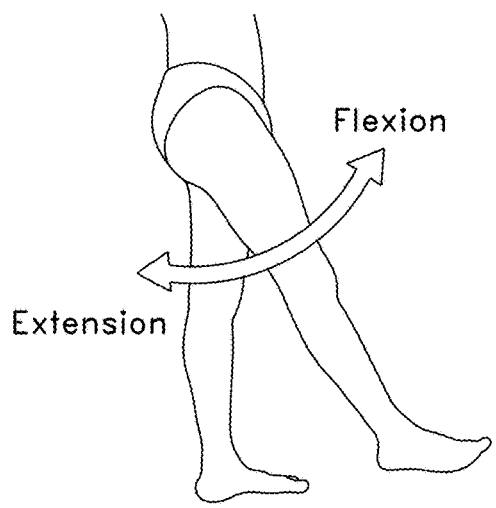
FIGS. 1A-1D are schematic views showing various aspects of hip motion.
Figure 1B:
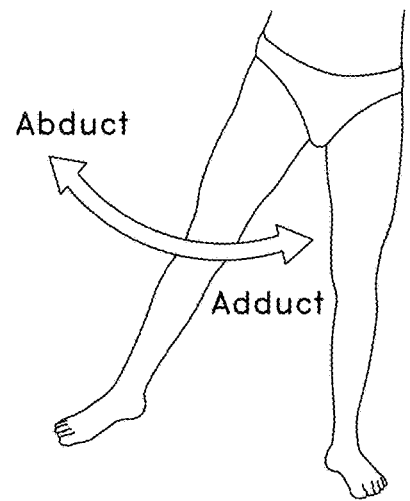
Figure 1C:
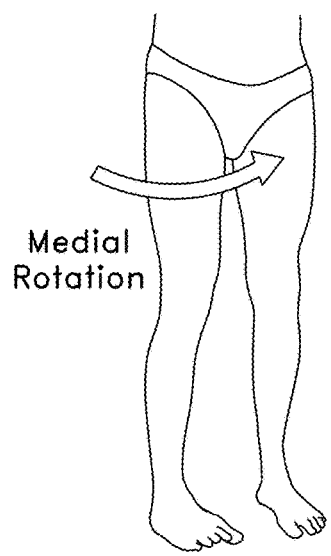
Figure 1D:
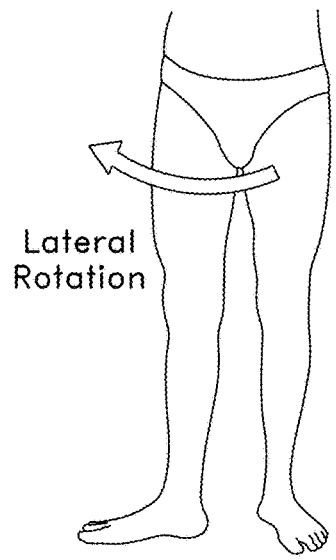
Figure 2:
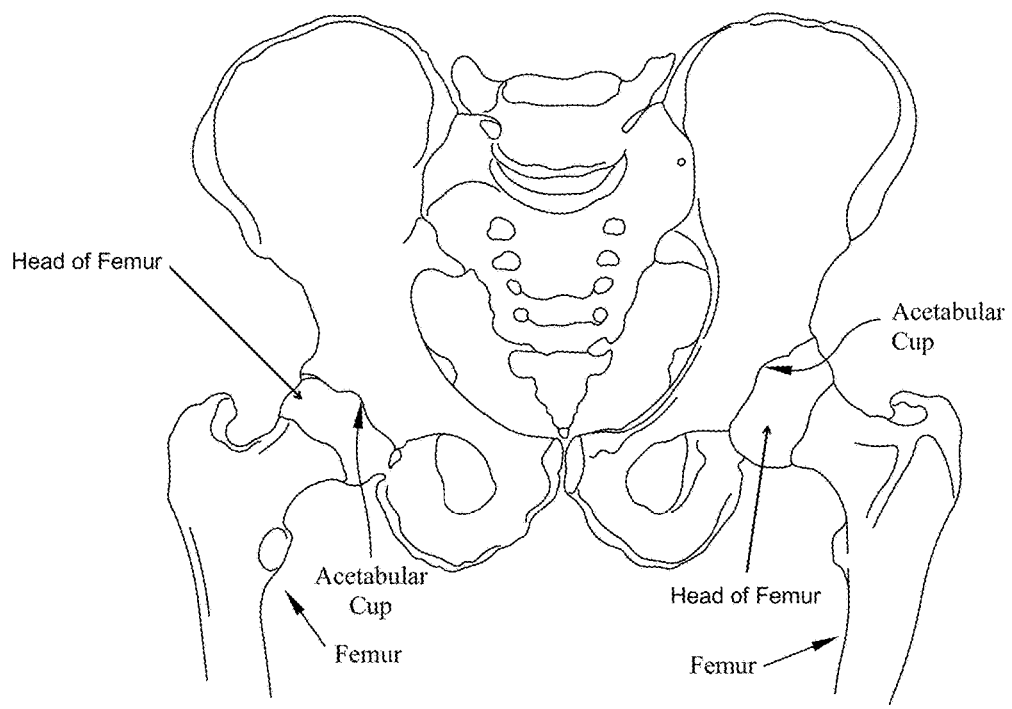
FIG. 2 is a schematic view showing bone structures in the region of the hip joint.
Figure 3:
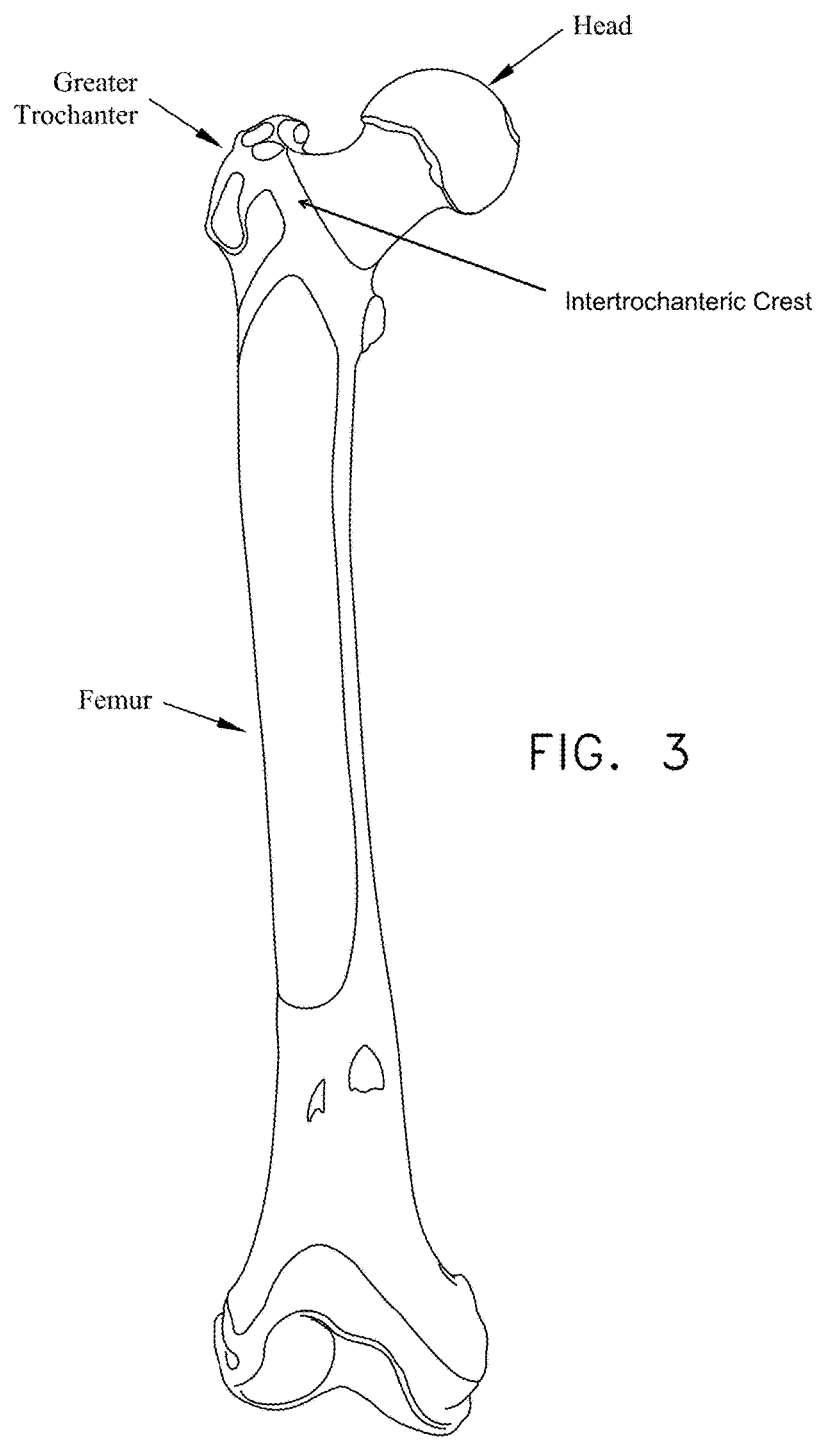
FIG. 3 is a schematic anterior view of the femur.
Figure 4:
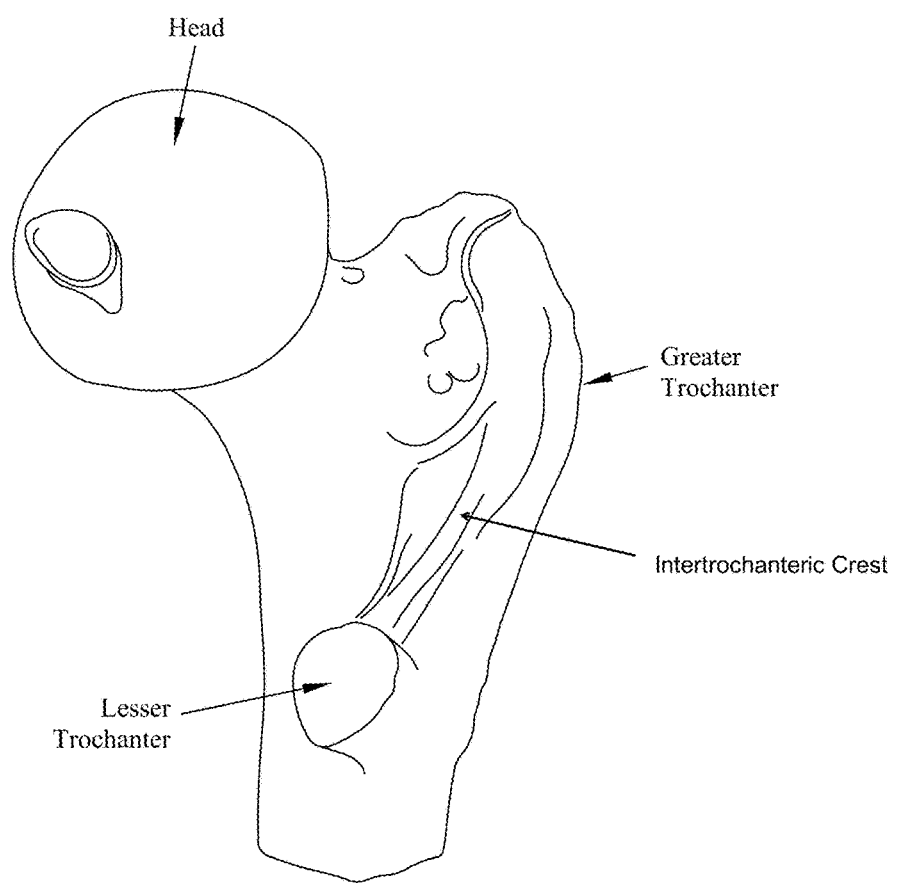
FIG. 4 is a schematic posterior view of the top end of the femur.
Figure 5:
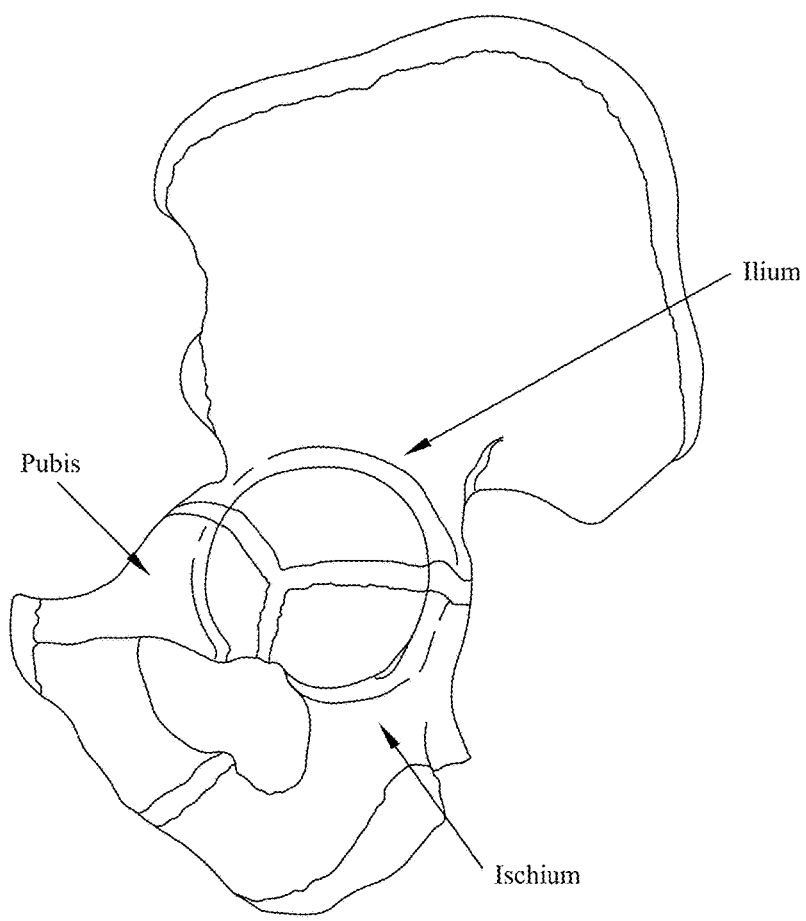
FIG. 5 is a schematic view of the pelvis.
Figure 6:
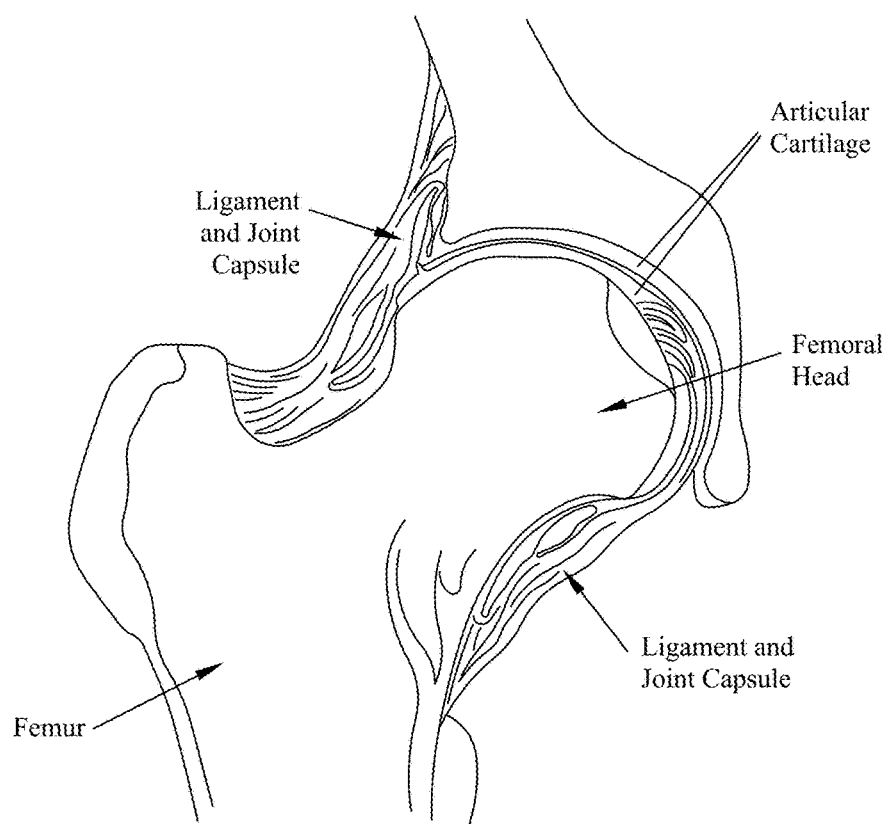
FIGS. 6-12 are schematic views showing bone and soft tissue structures in the region of the hip joint.
Figure 7:
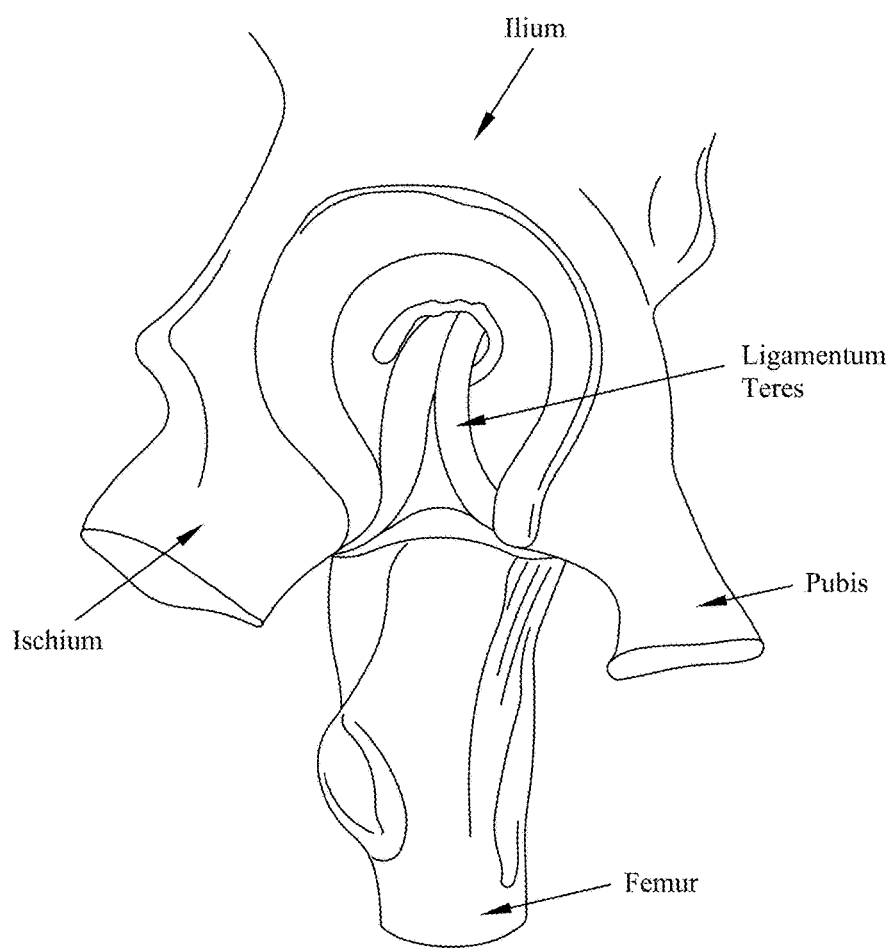
Figure 8:
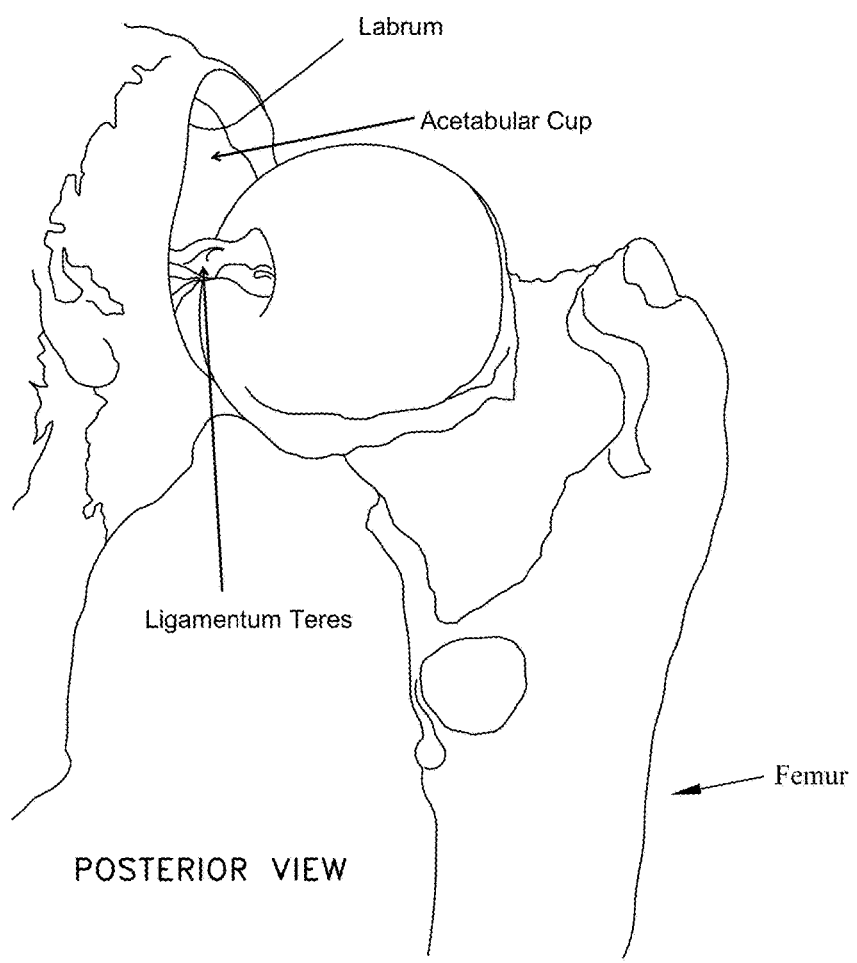
Figure 9:
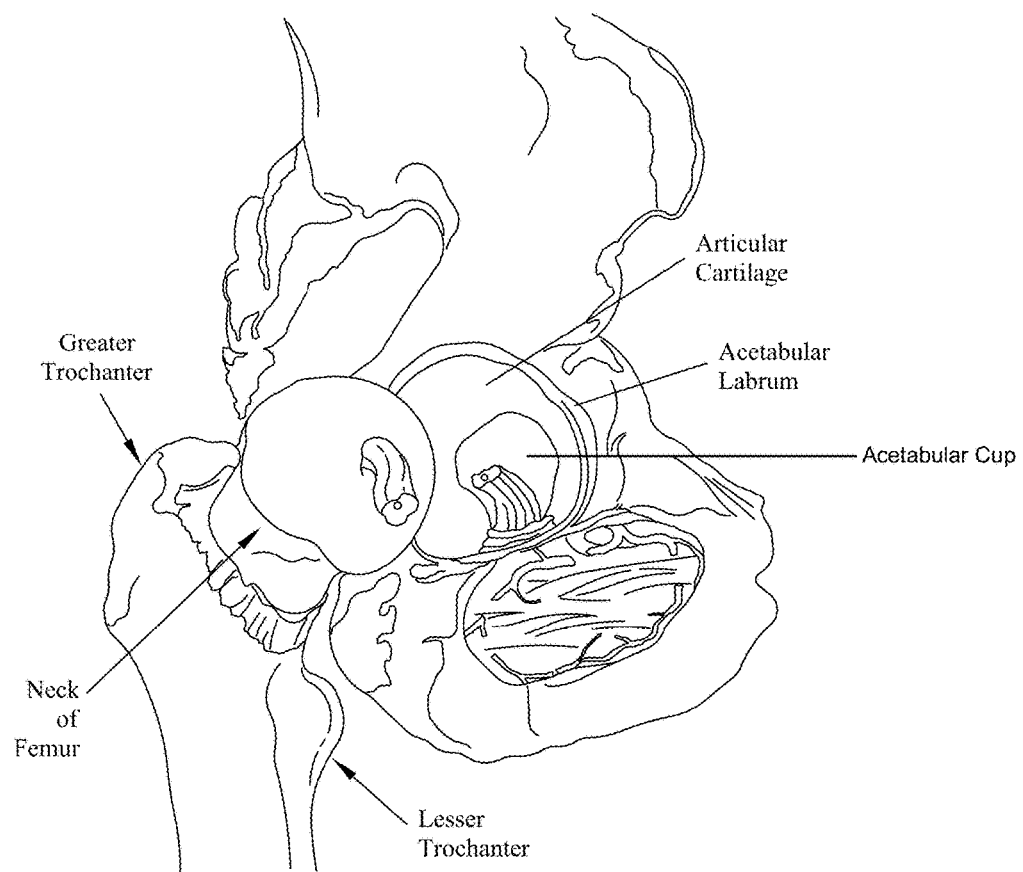
Figure 10:
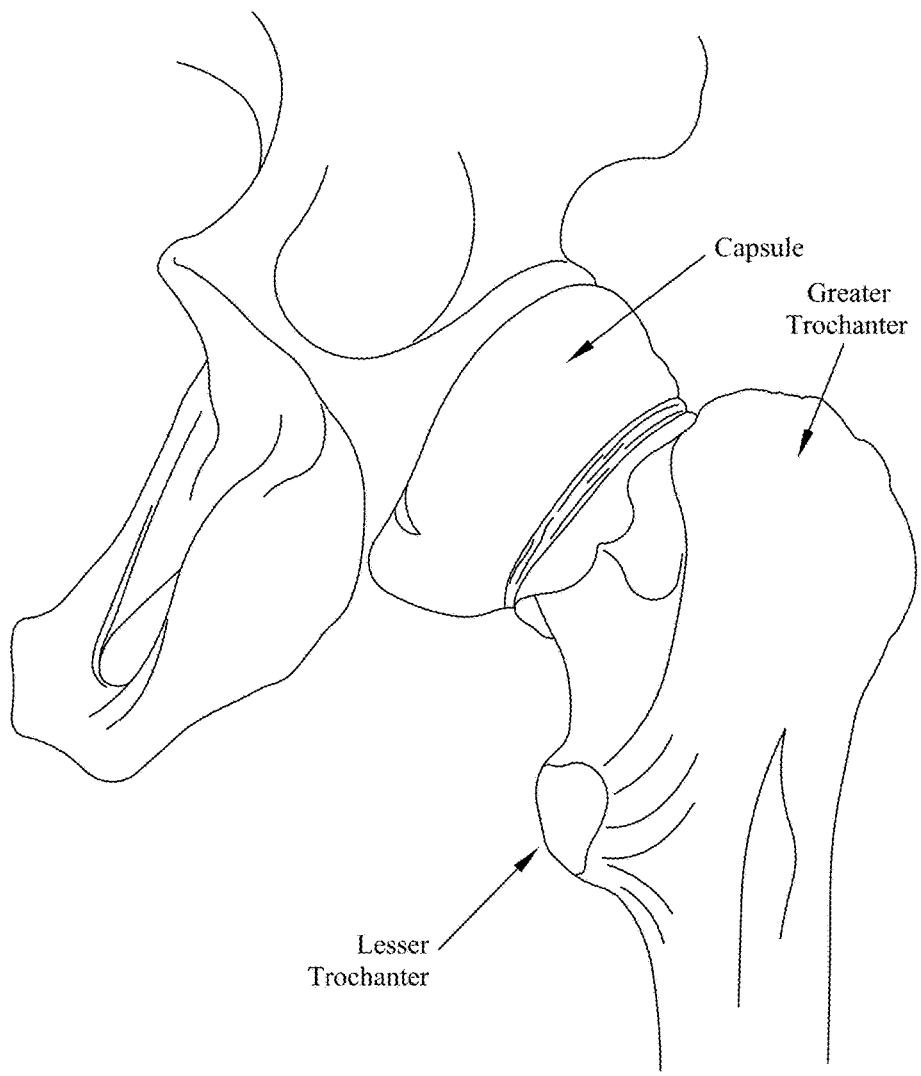
Figure 11:
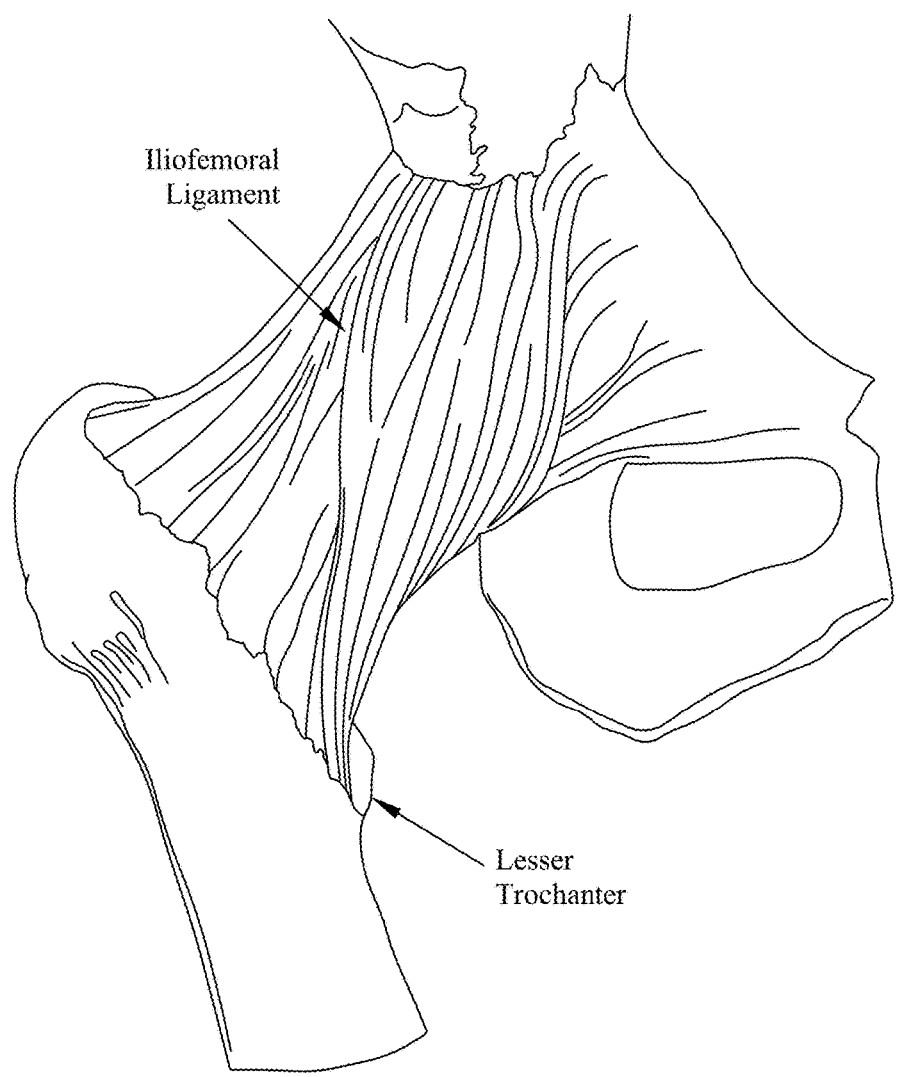
Figure 12:
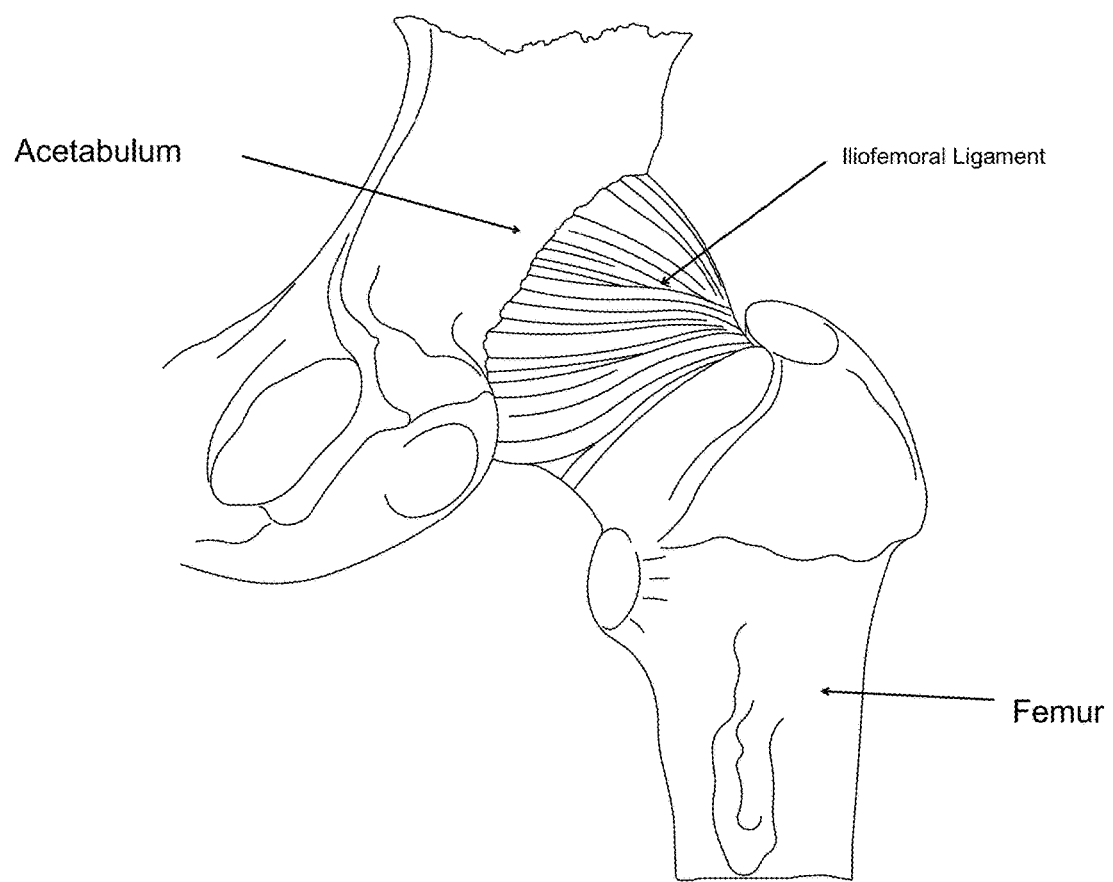
Figure 15:
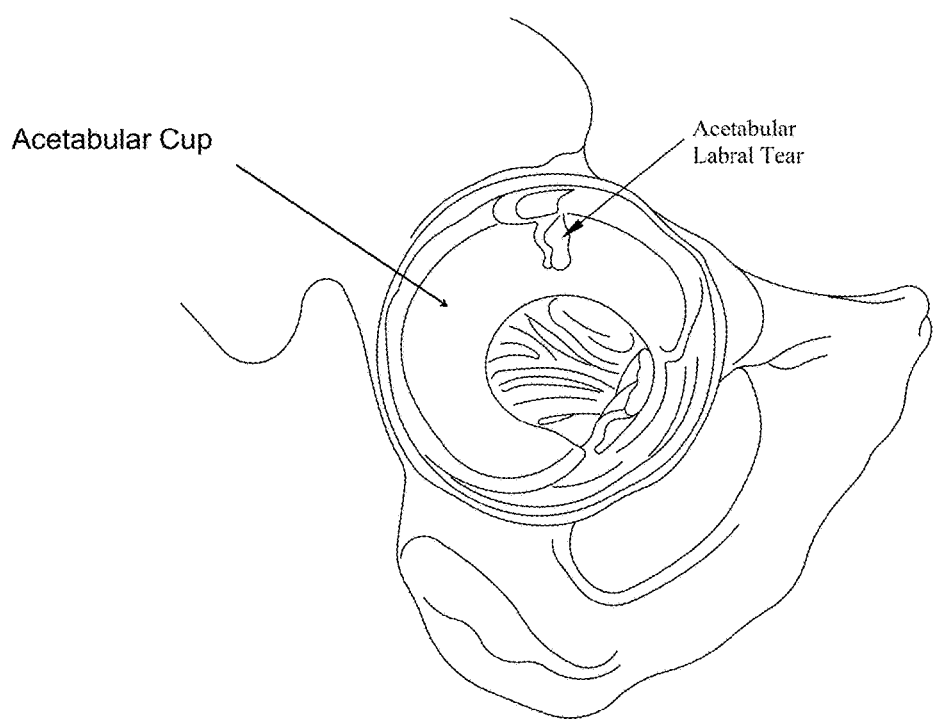
FIG. 15 is a schematic view showing a labral tear.
Figure 16:
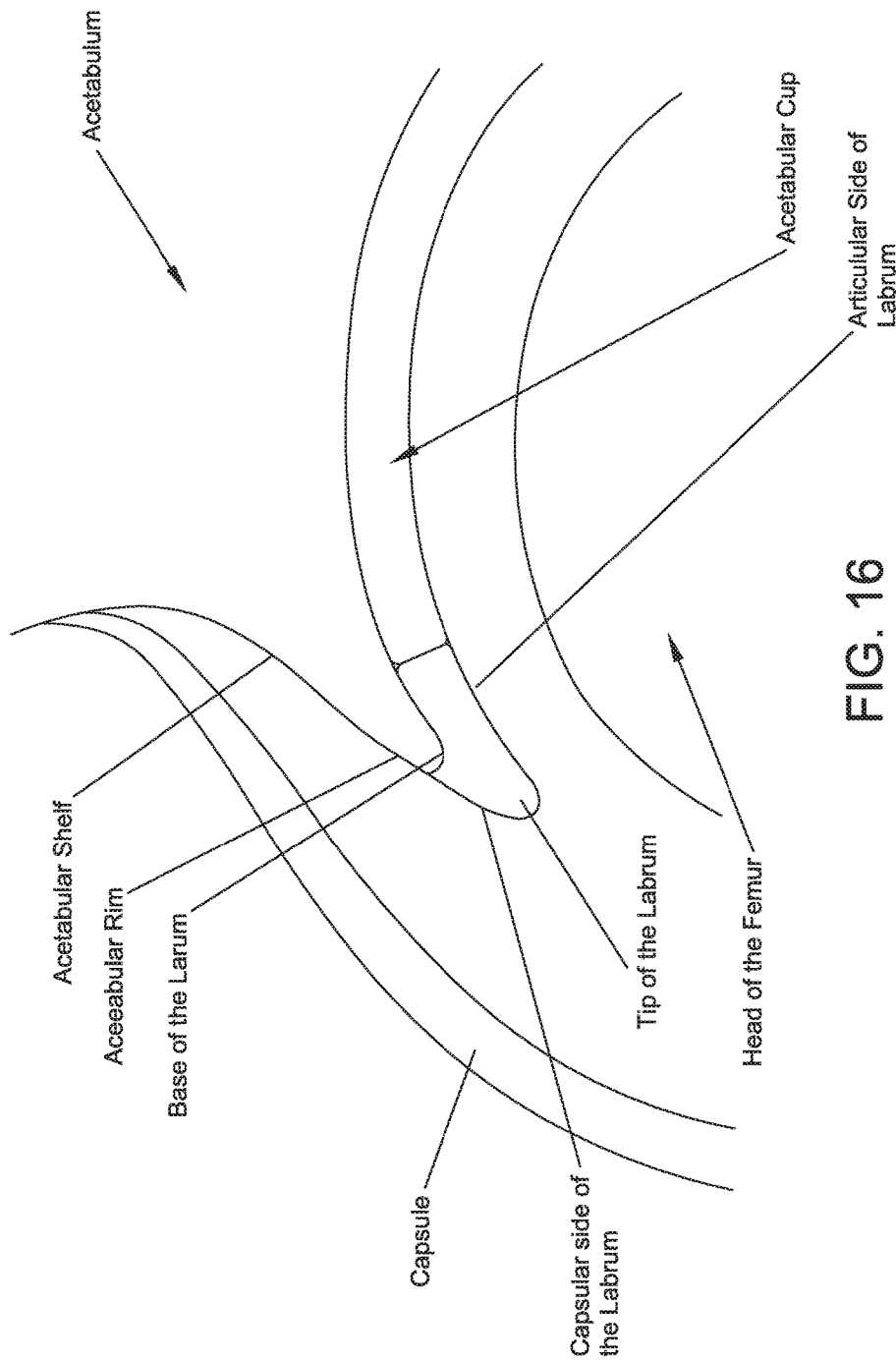
FIG. 16 is a schematic view showing a normal labrum which has its base securely attached to the acetabulum.
Figure 17:
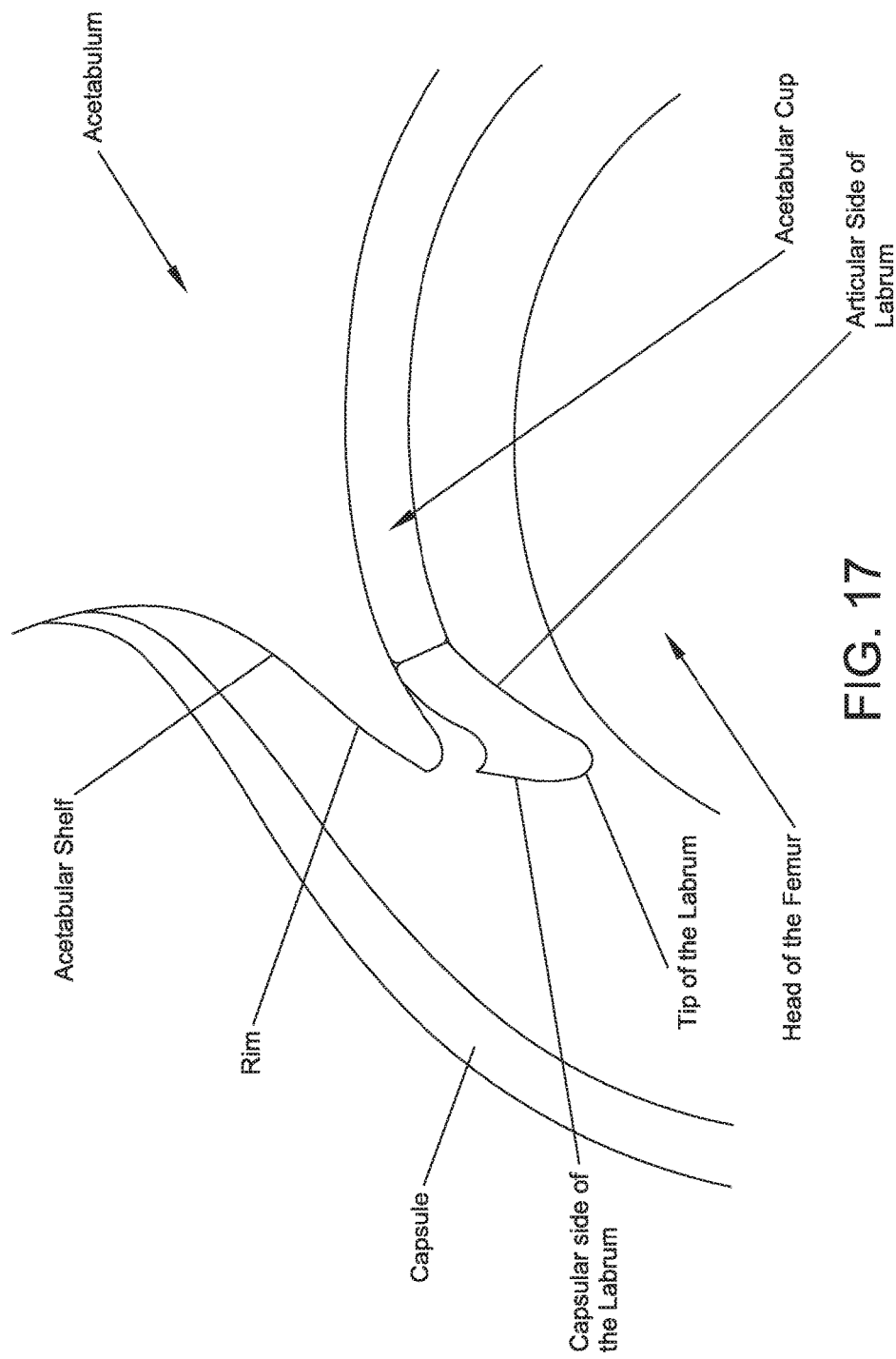
FIG. 17 is a schematic view showing a portion of the labrum detached from the acetabulum.
Figure 18:
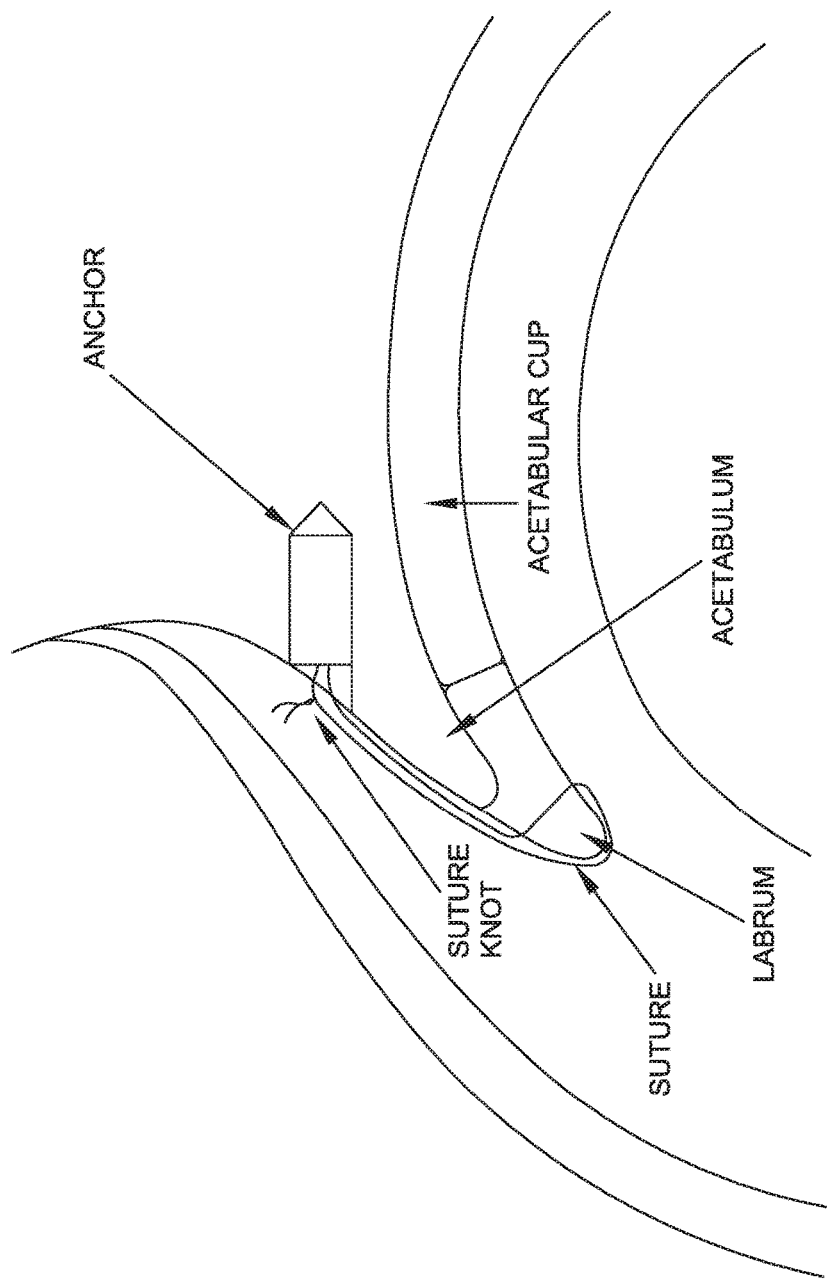
FIG. 18 is a schematic view showing a suture anchor being used to re-attach the labrum to the acetabulum.

Looking first at FIGS. 19 and 20, there is shown a novel knotless suture anchor system 5 formed in accordance with the present invention. Knotless suture anchor system 5 generally comprises a knotless suture anchor 10, an inserter 15 for inserting knotless suture anchor 10 in bone, and a suture threader 20 for threading a suture through knotless suture anchor 10 (and inserter 15) before the knotless suture anchor is deployed in bone.

Looking next at FIGS. 21-25, knotless suture anchor 10 generally comprises a body 25, a locking element 30 for radially expanding the body and securing a suture (not shown in FIGS. 21-25) to the body, and a pull rod 35 for moving locking element 30 proximally relative to body 25, whereby to simultaneously (i) radially expand the body so as to secure knotless suture anchor 10 to bone, and (ii) secure a suture to the body so as to secure that suture to knotless suture anchor 10 (and hence to the bone within which the knotless suture anchor is secured).

More particularly, and still looking now at FIGS. 21-25, body 25 comprises a distal end 40 terminating in a distal end surface 45, a proximal end 50 terminating in a proximal end surface 55, and a stepped bore 60 extending from distal end surface 45 to proximal end surface 55. Stepped bore 60 comprises a distal section 65 having a wider diameter, and a proximal section 70 having a narrower diameter. Distal section 65 preferably has a relatively smooth interior wall, and proximal section 70 preferably has a textured interior wall, e.g., threads 72. A shoulder 75 is formed at the intersection of distal section 65 and proximal section 70.

Body 25 of knotless suture anchor 10 has a generally cylindrical outer surface 80 which may include ribs (or other bone-engaging elements) 85. Ribs (or other bone-engaging elements) 85 may have various configurations, either identical to or varied from one another, and/or may be regularly or irregularly spaced, as will hereinafter be discussed. Body 25 also includes a side opening 90 which extends radially through the side wall of body 25 so as to connect stepped bore 60 with the region outside of the body 25 of knotless suture anchor 10. Side opening 90 is preferably located in the vicinity of shoulder 75. In one preferred form of the invention, side opening 90 extends from a region distal to shoulder 75 to a region approximately even with, or proximal to, shoulder 75. A portion of generally cylindrical outer surface 80 is recessed as shown at 95 (i.e., to accommodate a suture extending alongside the outer surface of the body), and the proximal end 50 of body 25 is reduced in diameter as shown at 100 so as to form an annular shoulder 105. Note that the axis of stepped bore 60 is off-center from the axis of outer surface 80 (FIG. 25) so as to strengthen the side wall of body 25 at 95 while still minimizing anchor diameter.

Still looking now at FIGS. 21-25, locking element 30 comprises an elongated body 110 having an enlarged distal end 115 which includes a thin flange 120 and terminates in a distal end surface 125, a proximal end 130 which terminates in a proximal end surface 135, and a stepped bore 140 which extends from distal end surface 125 to proximal end surface 135. Note that thing flange 120 has a larger diameter than enlarged distal end 115, and enlarged distal end 115 has a larger diameter than the portion of locking element 30 which is proximal to enlarged distal end 115. Proximal end 130 of locking element 30 is preferably tapered, e.g., in the manner shown in FIGS. 22 and 24, whereby to facilitate advancement of locking element 30 into proximal section 70 of stepped bore 60 of body 25, as will hereinafter be discussed. In one form of the present invention, proximal end 130 of locking element 30 includes a weakened section 132, preferably formed by a circumferential groove 133, whereby to allow the proximalmost portion of locking element 30 to separate from the remainder of locking element 30, as will hereinafter be discussed. Stepped bore 140 comprises a distal section 145 and a proximal section 150, with distal section 145 having a larger diameter than the diameter of proximal section 150, and with proximal section 150 having a smaller diameter than the diameter of distal section 145. A shoulder 155 is formed at the intersection of distal section 145 and proximal section 150. Locking element 30 has a generally cylindrical outer surface 160 which may include ribs (or other surface profile elements) 165. Ribs (or other surface profile elements) 165 may have various configurations, either identical to or varied from one another, and/or may be regularly or irregularly spaced, as will hereinafter be discussed.

Locking element 30 is sized so that (i) the diameter of its generally cylindrical outer surface 160 is less than the diameter of distal section 65 of stepped bore 60 of body 25, and (ii) the diameter of its flange 120 at the distal end of the locking element is larger than the diameter of distal section 65 of stepped bore 60 of body 25, such that cylindrical outer surface 160 of locking element 30 can be received in distal section 65 of stepped bore 60 of body 25, but flange 120 at the distal end of locking element 30 cannot normally be received in distal section 65 of stepped bore 60 of body 25. Furthermore, locking element 30 is sized so that when its flange 120 is seated against end surface 45 of body 25, proximal end surface 135 of locking element 30 is disposed distal to at least the proximalmost portion of side opening 90 in body 25 and, preferably, distal to the entire side opening 90 in body 25. In one preferred form of the invention, the diameter of generally cylindrical outer surface 160 of locking element 30 is approximately equal to, or somewhat larger than, the diameter of proximal section 70 of stepped bore 60 of body 25. As a result, when one or more sutures are disposed within distal section 65 of stepped bore 60 (i.e., when one or more sutures extend through proximal section 70 of stepped bore 60, through distal section 65 of stepped bore 60 and out of side opening 90, as will hereinafter be discussed), proximal movement of locking element 30 into proximal section 70 of stepped bore 60 of body 25 simultaneously causes (i) the creation of an interference fit between the generally cylindrical outer surface 160 of locking element 30, the one or more sutures extending through proximal section 70 of stepped bore 60 and the inner wall of proximal section 70 of stepped bore 60, and (ii) radial expansion of body 25. Thus it will be seen that proximal movement of locking element 30 into proximal section 70 of stepped bore 60 of body 25 causes radial expansion of the body so as to secure knotless suture anchor 10 to a surrounding bone, and captures the suture within the proximal section 70 of stepped bore 60, whereby to secure the suture to the knotless suture anchor 10 (and hence to the bone within which the knotless suture anchor 10 is secured). Furthermore, distal end 115 of locking element 30 has a diameter which is smaller than distal section 65 of stepped bore 60, but distal end 115 of locking element 30 has a diameter which is larger than proximal section 70 of stepped bore 60. As a result, distal end 115 of locking element 30 will stop proximal movement of locking element 30 when distal end 115 abuts shoulder 75 of body 25.

It will be appreciated that, when locking element 30 is moved proximally into proximal section 70 of stepped bore 60 of body 25, thin flange 120 (located at the distal end of locking element 30) will engage distal end surface 45 of body 25 and thereafter collapse (or bend) so that thin flange 120 is able to enter distal section 65 of stepped bore 60. By remaining engaged against distal end surface 45 of body 25 until a sufficient proximal force is applied to pull rod 35, thin flange 120 helps to prevent the unintentional actuation of knotless suture anchor 10 by requiring the application of a force to pull rod 35 above a pre-determined threshold force (i.e., the pre-determined force at which thin flange 120 collapses, or bends) in order to permit movement of locking element 30 proximally (whereby to actuate knotless suture anchor 10). Note that thin flange 120 also helps secure knotless suture anchor 10 on inserter 15 during delivery of the knotless suture anchor to the surgical site. This is of significance since, unlike knotted suture anchors which are typically delivered through a guide which provides mechanical support to the knotted suture anchor during delivery, knotless suture anchors are typically delivered without the benefit of such mechanical support and hence are subjected to more forces which can dislodge the knotless suture anchor from the inserter during delivery to the bone site and into the bone hole.

Looking now at FIGS. 21-27, pull rod 35 comprises an elongated body 170 having a distal end 175 terminating in an enlarged head 180, and a proximal end 185 terminating within the handle 190 of inserter 15, as will hereinafter be discussed in further detail. Elongated body 170 of pull rod 35 is sized to pass through proximal section 150 of bore 140 of locking element 30, and enlarged head 180 of pull rod 35 is sized to seat in distal portion 145 of bore 140 of locking element 30, such that pulling proximally on elongated body 170 of pull rod 35 will cause locking element 30 to move proximally.

It should also be appreciated that enlarged head 180 of pull rod 35 comprises a proximal surface 191 which extends circumferentially around the distal end of pull rod 35 at the junction of (or transition between) elongated body 170 and enlarged head 180. Proximal surface 191 of enlarged head 180 may comprise a fillet or chamfer, such that when a sufficient proximal force (i.e., a proximal force above a set threshold force) is applied to pull rod 35, enlarged head 180 can move proximally into bore 140 of locking element 30, as will hereinafter be discussed.

Looking now at FIGS. 19-27, inserter 15 generally comprises a shaft 195 having a distal end 200 terminating in distal end surface 205, a proximal end 210 terminating in a proximal end surface 215, and a bore 220 extending therebetween. Distal end 200 of shaft 195 comprises a counterbore 225 which is sized so as to receive the proximal end 50 of body 25 of knotless suture anchor 10, in a male/female connection, with distal end surface 205 of shaft 195 being seated against annular shoulder 105 of body 25. Note that the proximal end 50 of body 25 of knotless suture anchor 10 is not round (FIG. 25), and the cross-section of counterbore 225 is also not round, so as to resist twisting motions of suture anchor 10 vis-à-vis inserter 15. A side opening 227 extends radially through the side wall of shaft 195 so as to connect bore 220 with the region outside the shaft. Preferably side opening 227 in shaft 195 is aligned with side opening 90 in knotless suture anchor 10.

The proximal end 210 of shaft 195 is secured to handle 190. Handle 190 comprises a lever 230 which is rotatably mounted to handle 190 via a pivot pin 235. The proximal end 185 of pull rod 35 is secured to lever 230 such that when lever 230 is activated (i.e. squeezed towards handle 190), pull rod 35 is moved proximally, whereby to move locking element 30 proximally, as will hereinafter be discussed. A finger-to-finger engagement is provided at 232, 233 so as to prevent accidental activation of lever 230. Preferably pull rod 35 is set with a small amount of tension (that is below the threshold force that is required to retract locking element 30) so as to help hold suture anchor 10 on the distal end of inserter 15.

Looking next at FIGS. 19, 20 and 28, suture threader 20 is provided for threading a suture through knotless suture anchor 10 (and inserter 15) before the knotless suture anchor is deployed in bone. In one preferred form of the invention, suture threader 20 is pre-mounted to shaft 195 of inserter 15, with the suture threader having a portion threaded through inserter 15 and knotless suture anchor 10 so as to facilitate threading a suture (or multiple sutures) through the knotless suture anchor 10 and through inserter 15; see FIGS. 19 and 28. More particularly, suture threader 20 preferably comprises a body 240 having clamping arms 245 extending therefrom. Clamping arms 245 are configured to releasably secure body 240 of suture threader 20 to shaft 195 of inserter 15. A wire shaft 250 extends distally from body 240, and a collapsible, diamond-shaped capture element 255 is secured to the distal end of wire shaft 250. In a preferred embodiment, the wire shaft 250 and diamond-shaped capture element 255 are formed out of a single, thin Nitinol wire having its two terminal ends secured to body 240. Prior to use, suture threader 20 has its diamond-shaped capture element 255 collapsed radially inwardly, and it is passed through side opening 227 of shaft 195, along bore 220 of shaft 195 of inserter 15, along proximal portion 70 of stepped bore 60 of body 25 of knotless suture anchor 10, and out side opening 90 of body 25 of knotless suture anchor 10, whereupon diamond-shaped capture element 255 re-expands to its erected shape, e.g., in the manner shown in FIGS. 19 and 28.

Using the Knotless Suture Anchor System to Secure Suture to Bone

Figure 30:
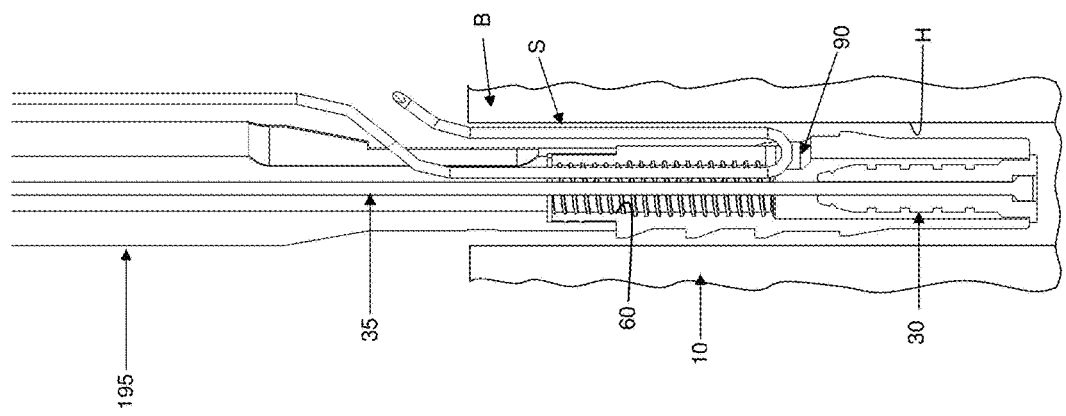
Figure 29:
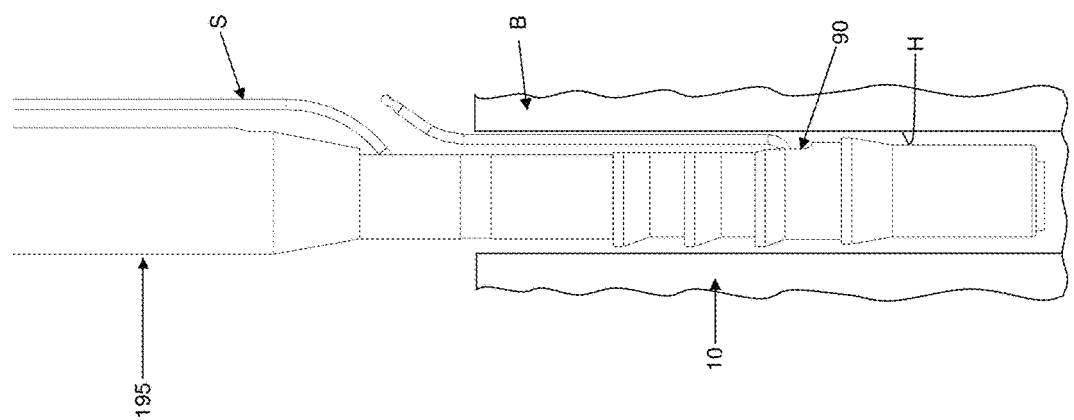
Figure 36:
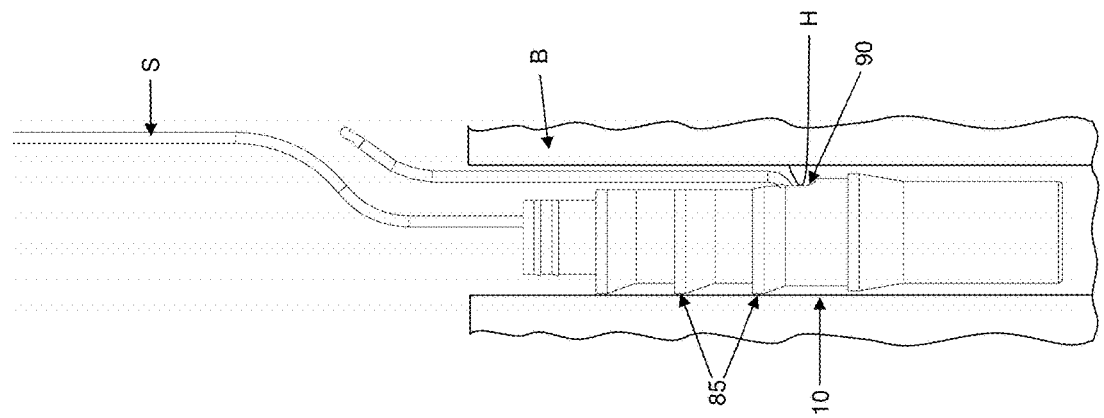
Figure 35:
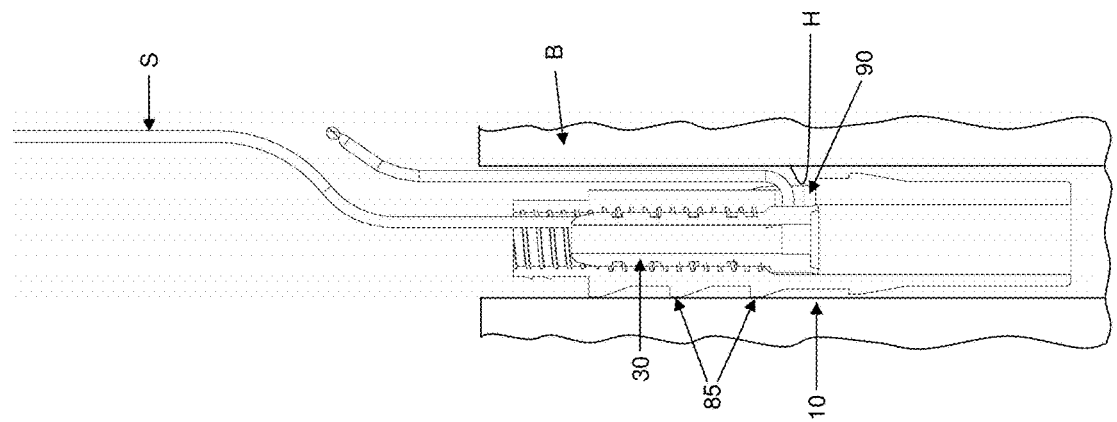
Figure 41:
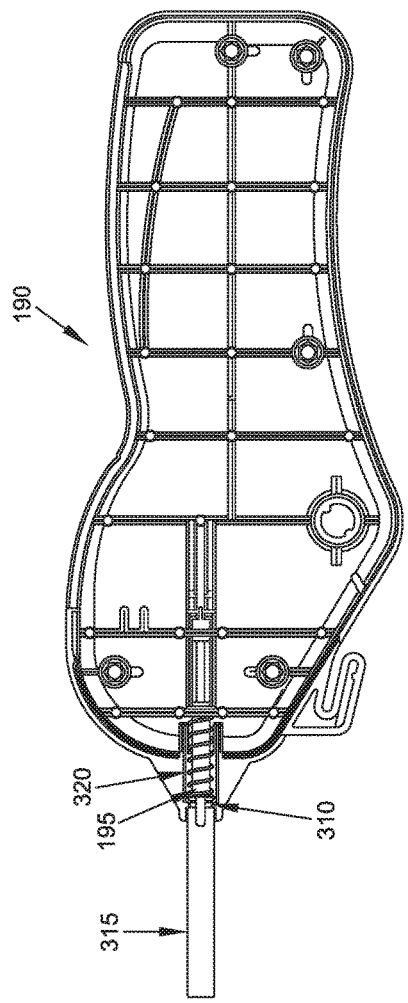
Figure 42:
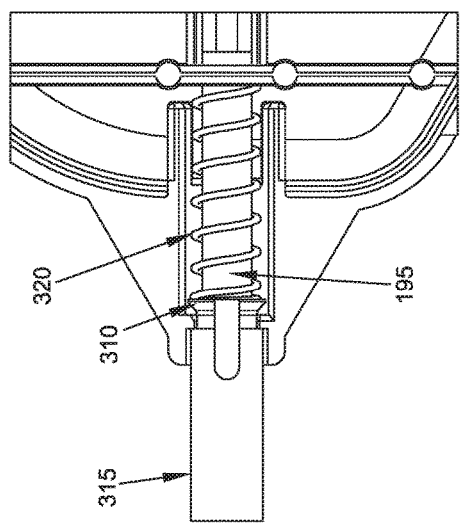
Figure 57:
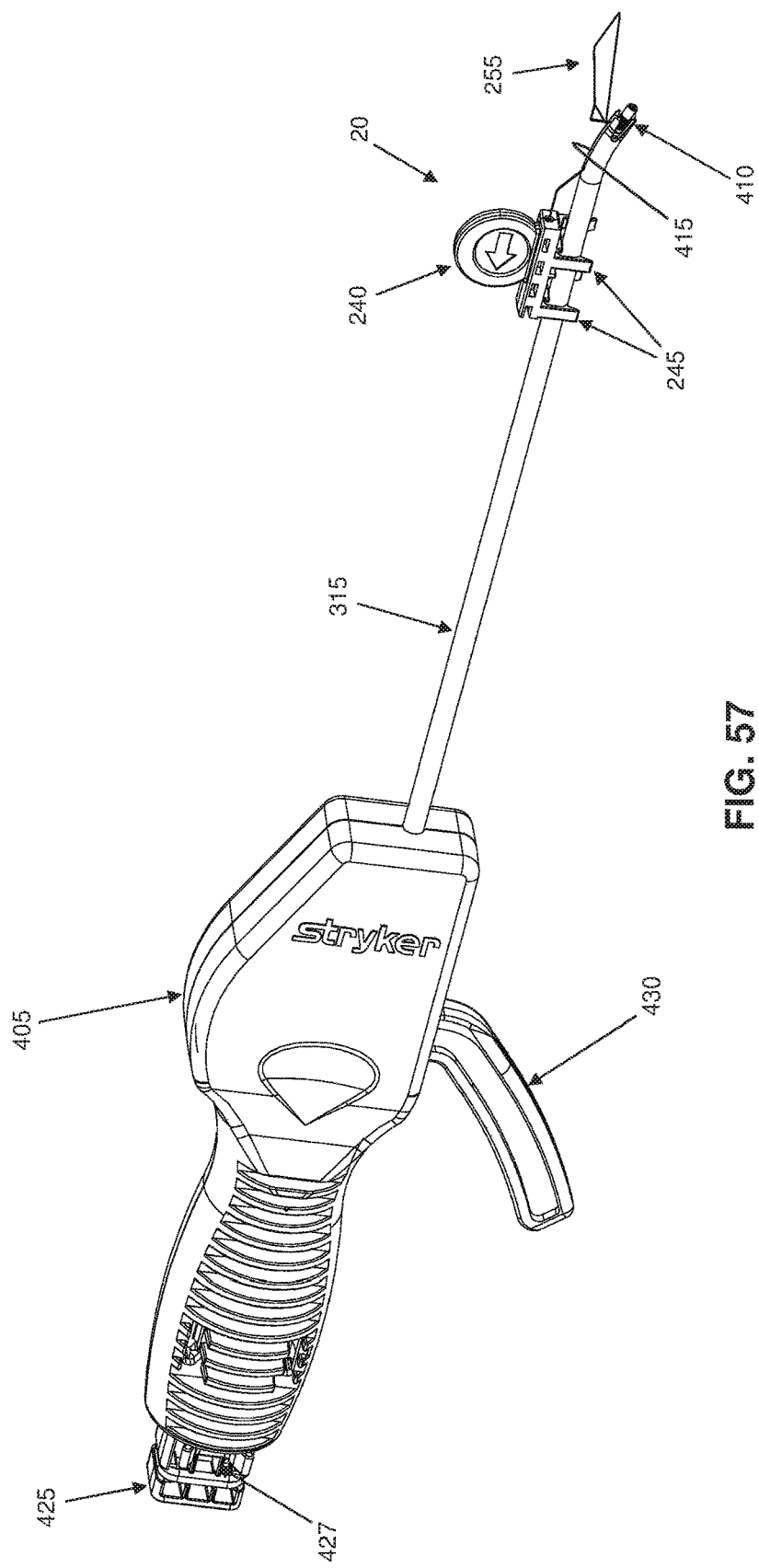
Figure 60:
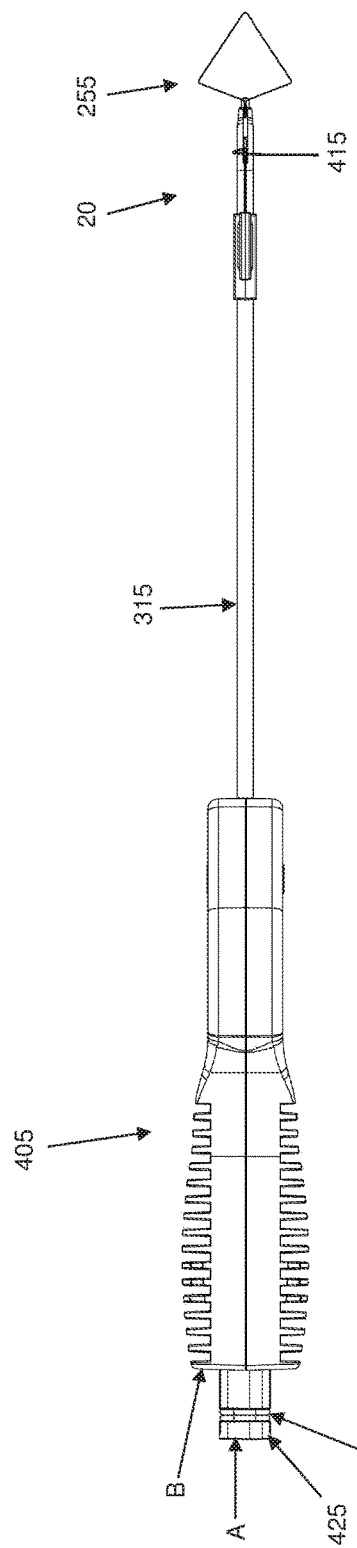
Figure 61:
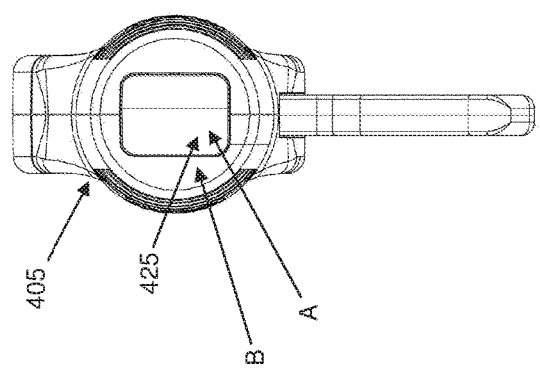

In use, the suture which is to be secured to a bone by means of knotless suture anchor 10 is first passed through the tissue which is to be secured to the bone, next the suture is passed through diamond-shaped capture element 255 of suture threader 20, and then suture threader 20 is pulled rearwardly on shaft 195 of inserter 15, towing the suture with it, until the suture has been pulled through side opening 90 of knotless suture anchor 10, along proximal portion 70 of stepped bore 60 of body 25 of knotless suture anchor 10, along bore 220 of shaft 195 of inserter 15, and out side opening 227 in shaft 195 of inserter 15. See FIGS. 29 and 30, which show an exemplary suture S threaded through body 25 of knotless suture anchor 10 and shaft 195 of inserter 15. It should be appreciated that, although a single suture strand is depicted in the figures, in a preferred embodiment, two strands of suture are threaded through body 25 of knotless suture anchor 5 and shaft 195 of inserter 15.

Thereafter, and looking now at FIGS. 29-36, in order to secure the suture S to a bone, inserter 15 is used to advance knotless suture anchor 10 and suture S into a hole H (FIGS. 29 and 30) formed in a bone B. Suture S may then be tensioned so as to adjust the position of the tissue relative to the bone. This can be accomplished by pulling on the free ends of the suture S, either independently or together. Sufficient tension will overcome any friction in the suture path and reduce the distance from the tissue to the knotless suture anchor 10 (and hence to the bone). Then the lever 230 is moved toward handle 190, whereby to force pull rod 35 proximally. This action causes locking element 30 to move proximally (FIGS. 31 and 32) so as to simultaneously (i) expand body 25 of knotless suture anchor 10 within the hole formed in the bone, whereby to secure knotless suture anchor 10 to the bone, and (ii) capture suture S between locking element 30 and the side wall of proximal portion 70 of stepped bore 60 of body 25 of knotless suture anchor 10, whereby to secure suture S to body 25 of knotless suture anchor 10. Further proximal movement of pull rod 35 (by way of moving lever 230 further towards handle 190) causes the enlarged head 180 of pull rod 35 to force its way through proximal portion 150 of stepped bore 140 of locking element 30 (FIG. 33). It should be appreciated that, in order to impart a sufficient proximal force to locking element 30 so as to move locking element 30 proximally, while still permitting enlarged head 180 to force its way through bore 140 of locking element 30 when a sufficient proximal force is applied to pull rod 35, enlarged head 180 needs to be larger in diameter than the diameter of proximal section 150 of bore 140 but not so large that it cannot be pulled through the bore 140 when sufficient proximal force is applied. It has been found that, with a bore 140 having a diameter of approximately 0.0135 inches, an enlarged head 180 having a diameter of approximately 0.0250 inches will provide adequate "interference" between enlarged head 180 and shoulder 155 so as to provide sufficient resistance to entering bore 140 when a proximal force less than the maximum proximal force (i.e., partial activation force) is applied (FIG. 32). At the same time, such a configuration permits the enlarged head 180 to enter bore 140 (FIG. 33) when a sufficient proximal force (i.e., full activation force) is applied to pull rod 35 (and hence to enlarged head 180).

In other words, with the present invention, the force required to pull locking element 30 proximally so as to lock suture S to the suture anchor, and so as to expand the body of the suture anchor, is less than the force required to draw pull rod 35 through locking element 30 so as to disengage pull rod 35 from locking element 30—this ensures that pull rod 35 is not disengaged from locking element 30 until locking element 30 has locked suture S to the suture anchor and expanded the body of the suture anchor. Furthermore, the force required to draw pull rod 35 through locking element 30 so as to disengage pull rod 35 from locking element 30 is less than the force required to pull locking element 30 through the proximal end of body 25 of the knotless suture anchor 10 (due to the fact that distal end 115 of locking element 30 is sufficiently larger than proximal section 150 of bore 140)—this ensures that pull rod 35 disengages from locking element 30 and locking element 30 is never pulled through the proximal end of body 25 of the knotless suture anchor 10. In other words, the force required to pull locking element 30 through proximal end of body 25 is greater than the force required to draw pull rod 35 through locking element so as to disengage pull rod 35 from locking element 30 (i.e., the full activation force).

In addition, the shape of proximal surface 191 of enlarged head 180 of pull rod 35 also influences the proximal force at which enlarged head 180 will enter into, and begin moving through, bore 140 in locking element 30. In a preferred form of the invention, proximal surface 146 of enlarged head 180 comprises a fillet of approximately 0.005 inches (or a chamfer of approximately 45 degrees).

Further proximal movement of pull rod 35 (i.e., by way of moving lever 230 even further towards handle 190) causes pull rod 35 to completely pull enlarged head 180 through bore 140 and out of the proximal end of locking element 30 (FIG. 34).

As noted above, locking element 30 comprises a weakened section 132 located at the proximal end of locking element 30. As enlarged head 180 encounters weakened section 132, the weakened section will separate from locking element 30, allowing a proximal portion of locking element 30 to detach from the locking element and be removed from the anchor by pull rod 35 (FIG. 34). At this point, inserter 15 can be removed from the hole H in bone B (see FIGS. 35 and 36), leaving the knotless suture anchor 10 secured in the hole H in the bone B, and with the suture S secured to the knotless suture anchor and emanating from the bone hole H, whereby to secure the suture (and hence the tissue which the suture S has been passed through) to the bone B.

Additional Constructions

In some cases the suture anchor may be subjected to transverse forces as it is advanced towards, and/or inserted into, the bone hole. This is particularly true where the suture anchor must be advanced through a tight corridor (e.g., such as in arthroscopic surgery), or along a tortuous path (e.g., such as when being advanced to a labral repair site within the hip), since in these situations the suture anchor may accidentally bump into intervening structures and/or the suture anchor may need to turn along a curved sheath during insertion. When this occurs, the suture anchor may be damaged and/or moved out of alignment with its inserter, etc., which can result in ineffective anchor placement in the bone.

Accordingly, in another embodiment of the present invention, and looking now at FIGS. 37-48, means are provided to shield and mechanically support knotless suture anchor 10 as it is advanced towards, and/or inserted into, the bone hole. More particularly, in this form of the invention, inserter 15 comprises a retractable sheath 310 which is co-axial with, and external to, the aforementioned inserter shaft 195. Inserter 15 also comprises an overtube 315. In this form of the invention, shaft 195 is secured to handle 190 (FIG. 42), retractable sheath 310 is coaxially mounted about shaft 195 and spring-biased in a distal direction by a compression spring 320, and overtube 315 is coaxially mounted about retractable sheath 310 and secured to handle 190. Preferably, when retractable sheath 310 is under the influence of compression spring 320, the distal end surface 325 of retractable sheath 310 is disposed proximal to the distal end of knotless suture anchor 10, but distal to the proximal end of knotless suture anchor 10 (see FIGS. 38 and 40). More preferably, the distal end of retractable sheath 310 is located between the midpoint of knotless suture anchor 10 and the distal end of knotless suture anchor 10. In this way, retractable sheath 310 can cover, and hence protect, the major length of knotless suture anchor 10 as the knotless suture anchor is advanced to the surgical site, but still expose the distal end of knotless suture anchor 10 so as to facilitate insertion of the knotless suture anchor into a bone hole. See FIGS. 37-42. However, when retractable sheath 310 is forced proximally, against the power of compression spring 320, knotless suture anchor 10 is completely exposed. See FIGS. 43-48. Preferably retractable sheath 310 and overtube 315 have distal markings 326 and 327, respectively, which provide indication of anchor depth. For example, when markings 326 and 327 align, the anchor is at the preferred depth. Additionally, retractable sheath 310 preferably has a slot 311 extending from its distal end (see FIGS. 40 and 46) to allow suture to pass from within retractable sheath 310 (i.e., from knotless suture anchor 10 and/or shaft 195) to outside retractable sheath 310. Slot 311 is preferably rotationally aligned with side opening 90 in knotless suture anchor 10 and opening 227 in the side wall of shaft 195.

In use, and looking now at FIGS. 49-52, retractable sheath 310 is initially disposed in its distal position, i.e., compression spring 320 actively pushes the proximal end of retractable sheath 310 away from handle 190, so that retractable sheath 310 covers the majority of the length of knotless suture anchor 10, but leaves the distal tip of the knotless suture anchor 10 exposed for easy locating into a bone hole H. Thereafter, when knotless suture anchor 10 is to be deployed into the bone hole H, the knotless suture anchor 10 is advanced (e.g., through an arthroscopic cannula) to the surgical site, with retractable sheath 310 covering, and protecting, the knotless suture anchor 10 during such advancement. Overtube 315 prevents retractable sheath 310 from prematurely retracting while the knotless suture anchor 10 is being delivered to the bone site. For example, the knotless suture anchor 10 may be passed through a cannula with an elastomeric septum; the septum, being grip-like in nature, will tend to grip the retractable sheath 310 and, consequently, retract the retractable sheath, thus removing some or all of the protection it was providing to the knotless suture anchor 10. Overtube 315 provides protection against this occurrence as the septum will bear against the overtube 315 (it being the outermost surface) instead of retractable sheath 310. Then the exposed distal tip of knotless suture anchor 10 is placed into bone hole H (FIGS. 49 and 50), with the distal end of retractable sheath 310 contacting the outer surface of the bone B. In this position, retractable sheath 310 contacts the outer surface of the bone B about the perimeter of the bone hole H and provides additional mechanical support against any transverse forces that may be applied to the knotless suture anchor 10 from the inserter 15, for example, if there is a misalignment between the arthroscopic portal and the axis of the bone hole H. The knotless suture anchor 10 is then advanced into the bone hole H. This is done by moving inserter 15 distally. As inserter 15 moves distally, shaft 195 advances the knotless suture anchor 10 into the bone hole H while the engagement of retractable sheath 310 with the outer surface of the bone B causes the retractable sheath 310 to remain stationary relative to the bone B. See FIGS. 51 and 52. Under this action, the power of compression spring 320 is overcome and the advancing handle 190 moves shaft 195 distally within retractable sheath 310. In other words, pushing handle 190 distally moves shaft 195 distally, while compression spring 320 allows retractable sheath 310 to remain seated on the outer surface of the bone B and retract into the advancing handle 190. During advancement of knotless suture anchor 10 into the bone hole H, retractable sheath 310 continues to provide mechanical support to the knotless suture anchor 10 as the knotless suture anchor 10 is pressed further into the bone hole. In this manner, retractable sheath 310 protects and supports knotless suture anchor 10 during delivery into the bone hole H.

In a preferred embodiment, retractable sheath 310 and overtube 315 are formed out of biocompatible materials such as stainless steel. In an alternative embodiment, retractable sheath 310 is formed out of a transparent polymer. In this embodiment, a distal marking 328 (FIG. 44) on the shaft 195 can be visualized through the transparent retractable sheath 310 to provide visual indication of anchor depth.

In another embodiment, the spring 320 may be sufficiently strong so as to overcome inadvertent retraction of retractable sheath 310 during delivery; hence, in this form of the invention, overtube 315 may be omitted.

Forming Shaft 195 with a Flexible Construction

In some situations it can be advantageous to form shaft 195 with a flexible construction. By way of example but not limitation, inserter 15 may sometimes approach the bone hole at an angle to the longitudinal axis of the bone hole. Where this occurs, and where shaft 195 is rigid, the rigid nature of shaft 195 can cause knotless suture anchor 10 to resist tracking the orientation of the bone hole during insertion of the knotless suture anchor into the bone hole. This can put additional stress on knotless suture anchor 10, and/or on the connection between knotless suture anchor 10 and shaft 195, and/or on other components of knotless suture anchor system 5 (e.g., it can put additional stress on pull rod 35).

To this end, and looking now at FIGS. 53-56, shaft 195 may be formed so as to be flexible, so that if inserter 15 approaches bone hole H at an angle to the longitudinal axis of the bone hole (FIG. 53), shaft 195 can flex so as to allow knotless suture anchor 10 to track the orientation of the bone hole during insertion of the knotless suture anchor into the bone hole (FIGS. 54 and 55). Various approaches may be used to form shaft 195 so that it is flexible, e.g., shaft 195 may be formed out of a flexible material (e.g., a superelastic material such as Nitinol) and/or shaft 195 may be provided with a series of laser cuts 400 (FIG. 55) so as to render the shaft flexible.

It will be appreciated that, in this form of the invention, pull rod 35 is also formed so as to be flexible.

In another form of the present invention, knotless suture anchor 10 may be formed with a flexible construction, such that where inserter 15 approaches the bone hole at an angle to the longitudinal axis of the bone hole, the knotless suture anchor can still track to the orientation of the bone hole during insertion of the knotless suture anchor into the bone hole. In one form of the present invention, knotless suture anchor 10 is flexible along its longitudinal axis (i.e., in bending). In this form of the invention, shaft 195 of inserter 15 is preferably also formed flexible so as to enhance tracking of the bone hole by shaft 195 of inserter 15 during insertion of the knotless suture anchor into the bone hole (although shaft 195 of inserter 15 may also be formed rigid if desired). And in this form of the invention, pull rod 35 is preferably also formed flexible so that pull rod 35 can follow a curved path where inserter 15 approaches the bone hole at an angle relative to the longitudinal axis of the bone hole. To this end, it should be appreciated that pull rod 35 may comprise a flexible shaft (e.g., Nitinol) or pull rod 35 may comprise a flexible cable, suture, etc.

Inserter Having Shaft 195 Carried by a Slidable Inner Carriage

As noted above, in some cases the knotless suture anchor (e.g., knotless suture anchor 10) may be subjected to transverse forces as the knotless suture anchor is advanced towards, and/or inserted into, bone hole H. This is particularly true where knotless suture anchor 10 must be advanced through a tight corridor (e.g., such as during arthroscopic surgery), and/or along a tortuous path (e.g., such as when the knotless suture anchor is being advanced to a labral repair site within the hip joint), since in these situations (as well as in others) knotless suture anchor 10 may accidentally bump into intervening structures, and/or knotless suture anchor 10 may need to pass through a curved sheath during advancement to the insertion site. When this occurs, knotless suture anchor 10 may be damaged, and/or moved out of alignment with its inserter, etc., either of which can result in ineffective anchor placement in the bone. This is particularly true where the size of knotless suture anchor 10 and its associated inserter are quite small (e.g., where knotless suture anchor 10 is approximately 2.8 mm in diameter).

Accordingly, with the construction shown in FIGS. 37-48, inserter 15 includes the aforementioned retractable sheath 310 which is coaxial with, and external to, the inserter shaft 195. This retractable sheath 310 is coaxially mounted about shaft 195 and is spring-biased in a distal direction by the compression spring 320. As a result of this construction, retractable sheath 310 covers at least a portion of knotless suture anchor 10 as the knotless suture anchor is advanced to the insertion site, however, when handle 190 is thereafter used to push the knotless suture anchor into the bone, engagement of retractable sheath 310 with the outer surface of the bone causes the retractable sheath 310 to retract into handle 190. In this way, retractable sheath 310 protects and supports the knotless suture anchor 10 during delivery to the bone hole, but does not interfere with insertion of the knotless suture anchor 10 into the bone hole.

In addition, with the construction shown in FIGS. 37-48, it has been found desirable to provide the aforementioned overtube 315, where overtube 315 is coaxially mounted about retractable sheath 310 and inserter shaft 195. Overtube 315 prevents retractable sheath 310 from prematurely retracting while the knotless suture anchor 10 is being delivered to the insertion site. By way of example but not limitation, the knotless suture anchor 10 may be passed through a cannula having an elastomeric septum; if the retractable sheath 310 were not protected by overtube 315, the septum, being grip-like in nature, could tend to grip retractable sheath 310 and, consequently, prematurely retract the retractable sheath 310, thus removing some or all of the protection the retractable sheath 310 provides to the knotless suture anchor 10 during advancement to the insertion site. Overtube 315 provides protection against this occurrence as the septum will bear against overtube 315 (since it provides the outermost surface of the assembly) instead of bearing against retractable sheath 310.

It will be appreciated that the construction shown in FIGS. 37-48 essentially provides an inserter comprising the handle 190, the inserter shaft 195 fixed to handle 190, the spring-biased retractable sheath 310 slidably mounted to handle 190, and the overtube 315 fixedly mounted to handle 190.

FIGS. 57-71 show an alternative construction for supporting and protecting knotless suture anchor 10 during approach and insertion into bone. More particularly, with the construction shown in FIGS. 57-71, there is provided an inserter handle 405 having an overtube 315 fixedly mounted thereto and extending distally therefrom. Overtube 315 is preferably curved (as shown in FIGS. 57 and 62-71) so as to enable curved (angled) delivery of knotless suture anchor 10. This can be beneficial when the desired angle of the bone hole differs from the access angle through the intervening tissue to the bone site. For example, in repairing the hip labrum, it is desirable to create a bone hole (and subsequently deliver an anchor) at an angle which tilts away from the acetabular cup. This angulation of the bone hole reduces the chance that the bone hole (and the subsequent anchor delivery) will penetrate into the acetabular cup surface.

Overtube 315 preferably comprises at least one tooth 410 at its distal end for engaging bone. Whereas the retractable sheath 310 discussed above supports anchor delivery to the bone hole, retractable sheath 310 does not engage the bone in such a way as to withstand transverse loads that may be imparted to knotless suture anchor 10 and/or to inserter shaft 195 during delivery of the knotless suture anchor into the bone hole, i.e., retractable sheath 310 is spring biased and, as such, cannot be, for example, pressed into the bone to securely engage the bone. Because the retractable sheath 310 cannot withstand transverse forces, knotless suture anchor 310 and/or inserter shaft 195 can be subjected to transverse forces during anchor insertion when the angle of the bone hole differs from the access angle through the intervening tissue to the site of the bone hole; this may result in ineffective anchor delivery and/or damage to the anchor and/or inserter shaft. The overtube 315, with at least one tooth 410 at its distal end for securely engaging bone, can withstand transverse forces that may be imparted during anchor delivery. This may occur when the angle of the bone hole differs from the access angle through the intervening tissue to the site of the bone hole (as previously discussed). This may also occur when overtube 315 is curved; in this construction (and as shown in FIGS. 62-75), an impact force applied to driver head 425 of inserter 15 for delivery of anchor 10 into the bone hole causes flexible inserter shaft 195 to contact the inside surface of overtube 315 and impart distal- and transverse-directed forces to overtube 315. As a result, the overtube 315 may impart distal- and transverse-forces against the bone surface; the at least one tooth 410 at the distal end of overtube 315 acts to securely engage overtube 315, and hence inserter 15, with the bone such that the forces imparted by overtube 315 against the bone surface will not cause the distal end of overtube 315 to shift on the bone surface, which could lead to ineffective placement of knotless suture anchor 10 and/or damage to knotless suture anchor 10 and/or inserter shaft 195. In addition, with the construction in FIGS. 62-75, since the axis of impact differs from the bone hole location, transverse forces can act on overtube 315 as it contacts the bone. Overtube 315 also comprises a distal slot 415 (FIG. 58) so as to enable passage of suture S from knotless suture anchor 10 through overtube 315. Distal slot 415 extends to the distal end of overtube 315 so as to enable suture S to freely slide out of overtube 315 when the knotless suture anchor 10 is disengaged from inserter shaft 195.

Inserter shaft 195 is slidably disposed within overtube 315. Inserter shaft 195 is preferably flexible at its distal end (i.e., along the length extending along the curve of overtube 315). This can be accomplished by forming inserter shaft 195 out of a flexible material (e.g., a superelastic metal such as Nitinol) or by forming a series of laser cuts 400 in inserter shaft 195 (as can be seen in FIG. 69) so as to render inserter shaft 195 flexible. The distal end of inserter shaft 195 releasably carries knotless suture anchor 10 in the manner previously described.

The proximal end of inserter shaft 195 is fixedly attached to a slidable inner carriage 420 (FIGS. 66, 68 and 70) which is movably mounted within inserter handle 405. Slidable inner carriage 420 is moved relative to inserter handle 405 by applying force to a driver head 425 which is exposed at the proximal end of inserter handle 405. Thus, by moving driver head 425 distally (e.g., by striking driver head 425 with a mallet), slidable inner carriage 420 is moved distally, whereby to move inserter shaft 195 (and hence knotless suture anchor 10) distally.

In one preferred form of the invention, a removable stop 427 is releasably secured to driver head 425. Removable stop 427 prevents driver head 425 from being inadvertently driven distally, and hence prevents slidable inner carriage 420, inserter shaft 195 and knotless suture anchor 10 from being inadvertently driven distally. However, when removable stop 427 is removed from driver head 425, the driver head (and hence slidable driver carriage 420, inserter shaft 195 and suture anchor 10) may be moved distally (e.g., by striking driver head 425 with a mallet).

And in one preferred form of the invention, slidable inner carriage 420 comprises one or more projections 428, and inserter handle 405 comprises one or more resilient fingers 429, whereby to permit slidable inner carriage 420 to move distally within inserter handle 405 but prevent slidable inner carriage 420 from moving proximally within inserter handle 405. More particularly, in this form of the invention, projections 428 and resilient fingers 429 form a ratchet-type mechanism for ensuring substantially one-way movement of slidable inner carriage 420 relative to inserter handle 405. As a result, when driver head 425 is moved distally (and hence slidable inner carriage 420 is moved distally), projections 428 and resilient fingers 429 cooperate to prevent slidable inner carriage 420 from thereafter returning substantially proximally. As the one or more projections 428 encounter the one or more fingers 429, there is resistance against slidable inner carriage 420 moving distally within inserter handle 405. In other words, when one or more resilient fingers 429 encounter one or more projections 428, a threshold force is required to flex resilient finger(s) 429 sufficiently for projection(s) 428 to pass under resilient finger(s) 429 and thus allow slidable inner carriage 420 to move distally within inserter handle 405. In one embodiment, when slidable inner carriage 420 is in its proximal position (FIG. 66), a resilient finger 429 is adjacent to a projection 428 so as to create a force which must be overcome before slidable inner carriage 420 advances distally. This feature can be advantageous, for example, so that as the inserter 15 is advanced to the bone site, any inadvertent distal pressure or force on the driver head 425 and/or actuation lever 430 will not advance the slidable inner carriage 420 (and hence advance knotless suture anchor 10 further out of the overtube 315).

Slidable inner carriage 420 includes an actuation lever 430 which is pivotally connected to slidable inner carriage 420. More particularly, actuation lever 430 is pivotally mounted to slidable inner carriage 420 and moves distally when slidable inner carriage 420 moves distally. Actuation lever 430 is connected to the proximal end of pull rod 35 for actuating knotless suture anchor 10 (i.e., by moving pull rod 35 proximally) once the knotless suture anchor is inside bone hole H, whereby to bind suture S to knotless suture anchor 10 and secure the knotless suture anchor to the bone. It will be appreciated that pull rod 35 extends through inserter shaft 195 for connection to actuation lever 430. Note that, if desired, lever 430 may be replaced by a different form of actuator, e.g., a rotatable knob, etc., for selectively moving pull rod 35 proximally.

The construction shown in FIGS. 57-71 may be used in the following manner. First, a bone hole (e.g., a bone hole H) is created in the bone. Bone hole H is preferably created by passing a drill bit or punch through a curved guide and into the bone. The drill bit or punch and the curved guide are then removed from the surgical site. Next suture S is passed through the tissue that is to be secured to the bone. Then suture S is threaded through knotless suture anchor 10. More particularly, the inserter and knotless suture anchor are initially in the position shown in FIGS. 57-59, i.e., with slidable inner carriage 420 positioned proximally within inserter handle 405 so that knotless suture anchor 10 is substantially shielded, yet slightly exposed, at the distal end of overtube 315, and so that driver head 425 is spaced from the proximal end of inserter handle 405. Removable stop 427 is removed from driver head 425 (FIGS. 60 and 61) and suture S is threaded through knotless suture anchor 10 using suture threader 20 in the manner previously described (FIGS. 62-67). Then inserter handle 405 is used to advance knotless suture anchor 10 (still substantially shielded within overtube 315) to the insertion site (i.e., bone hole H). Distal end of anchor 10 may be used to help locate bone hole H. Inserter 15 is then rotated to the desired direction of curved delivery; for example, for hip labral repair, the curvature of inserter 15 would typically be directed away from the acetabular cup. The exposed distal end of the anchor 10 is placed into bone hole H by manual manipulation of inserter handle 405. Anchor 10 is inserted into bone hole H until the distal end of overtube 315 contacts bone. Tooth 410 on the distal end of overtube 315 is then engaged with bone. See FIG. 72. With overtube 315 sufficiently engaged with bone, driver head 425 is moved distally (e.g., by striking the driver head 425 with a mallet), whereby to move slidable inner carriage 420 distally, whereby to move flexible inserter shaft 195 distally, whereby to advance knotless suture anchor 10 out of overtube 315 and into bone hole H (FIGS. 68, 69 and 73). Suture S is then tensioned to adjust the position and/or tension of the tissue relative to knotless suture anchor 10 (and hence the bone). Then lever 430 is activated, whereby to move pull rod 35 proximally and hence to move locking element 30 proximally within knotless suture anchor 10, whereby to bind suture S to knotless suture anchor 10 and secure the tissue to the bone (FIGS. 70, 71 and 74). Then inserter 15 is withdrawn from the insertion site by withdrawing inserter handle 405 proximally, leaving knotless suture anchor 10 deployed in bone hole H. See FIG. 75.

Thus it will be seen that with the construction shown in FIGS. 57-71, overtube 315 is fixed to inserter handle 405, and the driver head 425 is used to move slidable inner carriage 420 distally, whereby to advance flexible inserter shaft 195 distally out of overtube 315, whereby to insert knotless suture anchor 10 into bone hole H. Thus, overtube 315 protects and supports knotless suture anchor 10 during advancement to the insertion site and, by engaging the bone surface, resists transverse forces that otherwise would be subjected onto the knotless suture anchor 10 and/or inserter shaft 195.

With respect to the construction shown in FIGS. 57-75 (in which driver head 425 is moved distally relative to inserter handle 405, e.g., by striking driver head 425 with a mallet, so as to move slidable inner carriage 420 distally relative to inserter handle 405, whereby to move flexible inserter shaft 195 distally relative to overtube 315, whereby to advance knotless suture anchor 10 out of overtube 315 and into bone hole H), it will be appreciated that it is important that inserter handle 405 be kept stationary while driver head 425 is moved distally during insertion of knotless suture anchor 10 in bone hole H. This is important because if inserter handle 405 is inadvertently driven distally (e.g., by inadvertently striking inserter handle 405 with the mallet which is used to strike driver head 425), the distal tip of overtube 315 could be driven into the bone, which could interfere with proper anchor placement and/or cause undesirable trauma to the bone. Additionally, if the mallet were to inadvertently strike inserter handle 405 instead of driver head 425, the distal tip of overtube 315 could skip along the bone due to the fact that the distal end of the overtube 315 curves away from the longitudinal axis of overtube 315, which could cause knotless suture anchor 10 to move out of bone hole H and/or cause damage to knotless suture anchor 10 and/or damage to the bone. Thus, it is important that only driver head 425, and not inserter handle 405, be driven distally during insertion of knotless suture anchor 10 in bone hole H, so that slidable inner carriage 420 and flexible inserter shaft 195 can move knotless suture anchor 10 distally while overtube 315 remains aligned with bone hole H.

To this end, and still looking now at FIGS. 57-75, in one preferred form of the invention, driver head 425 and inserter handle 405 are configured so that driver head 425 stands proud of inserter handle 405 at both the start and finish of the anchor-insertion process, so as to minimize the possibility that the mallet might inadvertently strike inserter handle 405 (rather than driver head 425) during insertion of knotless suture anchor 10 in bone hole H.

Figure 62:
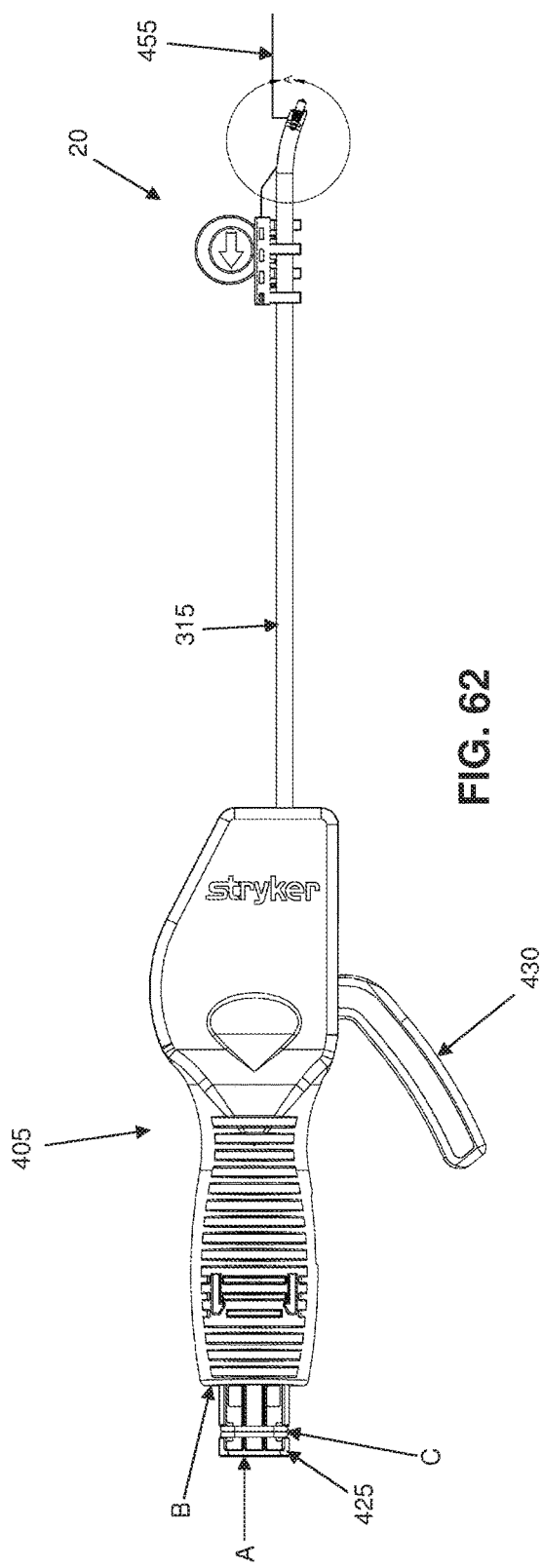
Figure 63:
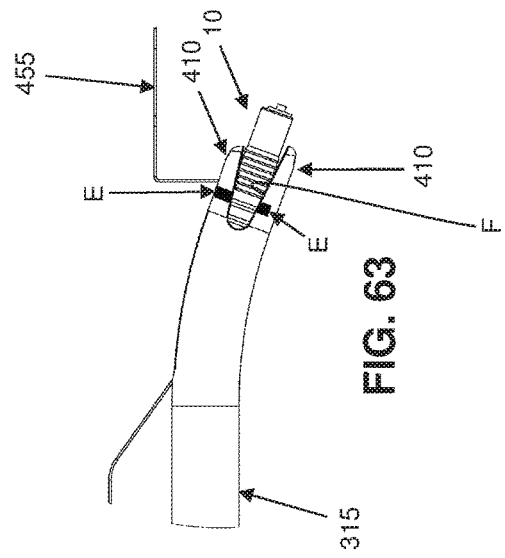

More particularly, as seen in FIGS. 57, 58, 60, 62, 64 and 66, when driver head 425 is in its "proximal" position (i.e., so that knotless suture anchor 10 is largely sheathed within overtube 315, as seen in the corresponding FIGS. 62, 65 and 67), the proximal surface A of driver head 425 is displaced proximally from the proximal surface B of inserter handle 405; and as seen in FIGS. 68 and 70, when driver head 425 is in its "distal" position (i.e., so that knotless suture anchor 10 is extended out of overtube 315 for insertion into bone hole H, as seen in the corresponding FIGS. 69 and 71), proximal surface A of driver head 425 is still displaced proximally from proximal surface B of inserter handle 405, albeit by a shorter distance (i.e., by the distance that flexible inserter shaft 195 is to advance knotless suture anchor 10 distally into bone hole H). By configuring driver head 425 and inserter handle 405 so that driver head 425 stands proud of inserter handle 405 at both the start and finish of the anchor-insertion process, the possibility that the mallet might inadvertently strike inserter handle 405 (rather than driver head 425) is minimized.

In order to assist the user in knowing when driver head 425 has been advanced an appropriate distance relative to inserter handle 405 for proper anchor insertion, driver head 425 is preferably provided with a visual marker C, with driver head 425 being advanced an appropriate distance relative to inserter handle 405 when visual marker C is aligned with proximal surface B of inserter handle 405 (see FIGS. 68 and 70). By way of example but not limitation, visual marker C may comprise a circumferential groove, which may or may not be visually enhanced with coloration, or an O-ring disposed in the circumferential groove, where the O-ring may itself be visually enhanced with coloration, etc. Note that when visual marker C has been advanced into alignment with proximal surface B of inserter handle 425, proximal surface A of driver head 425 will still stand well proud of proximal surface B of inserter handle 425, whereby to minimize the possibility that a mallet might inadvertently strike proximal surface B of inserter handle 425, which could adversely affect anchor insertion into bone hole H (e.g., due to overtube 315 being driving into the bone, or due to overtube 315 skipping along the surface of the bone). Thus, visual marker C helps the user know when driver head 425 has been driven far enough to properly insert knotless suture anchor 10 into bone hole H while still keeping proximal surface A of driver head 425 sufficiently proud above proximal surface B of inserter handle 405 to minimize the risk of a mallet blow inadvertently striking inserter handle 405.

It should be appreciated that providing visual marker C on driver head 425 provides the user with an additional advantage beyond ensuring adequate anchor insertion while minimizing the risk of a mallet blow inadvertently striking inserter handle 425. More particularly, by providing visual marker C to guide the extent to which driver head 425 moves distally relative to inserter handle 425, the user is also provided with a visual guide to prevent over-inserting knotless suture anchor 10 into bone hole H. In this respect it should be appreciated that if knotless suture anchor 10 were to be advanced too far into bone hole H, knotless suture anchor 10 could "bottom out" in bone hole H. This is undesirable, since attempting to drive knotless suture anchor 10 further distally after the knotless suture anchor has bottomed out in bone hole H could cause damage to knotless suture anchor 10 and/or flexible inserter shaft 195 and/or other parts of the inserter. Any of these could undermine effective deployment of knotless suture anchor 10 and/or release of knotless suture anchor 10 from flexible inserter shaft 195. Thus, providing visual marker C on driver head 425 helps the user avoid over-inserting knotless suture anchor 10 into bone hole H. Additionally, bone hole H is drilled sufficiently deep so as to allow a clearance between the distal end of the knotless suture anchor 10 and the bottom of bone hole H when visual marker C on driver head 425 is aligned with proximal surface B of inserter handle 405 (i.e., knotless suture anchor 10 does not bottom out in bone hole H when visual marker C on driver head 425 is aligned with proximal surface B of inserter handle 405).

In order to further assist the user in knowing when flexible inserter shaft 195 has been advanced an appropriate distance relative to overtube 315 (whereby to ensure adequate seating of knotless suture anchor 10 in bone hole H without over-inserting knotless suture anchor 10 into bone hole H), a visual marker D (e.g., a line) may be provided on the distal end of flexible inserter shaft 195 and visual marker E (e.g., a line) may be provided on one or both sides of a window F provided on the distal end of overtube 315 (see FIGS. 63, 65, 67, 69, 71 and 72-75), so that the surgeon can monitor proper advancement of flexible inserter shaft 195 relative to overtube 315 while viewing the surgical site (e.g., through an endoscope); when visual marker D on flexible inserter shaft 195 is aligned with visual marker(s) E on overtube 315, knotless suture anchor 10 will have been advanced an appropriate distance into bone hole H. In one preferred form of the invention, window F opens on the distal end surface of overtube 315, e.g., as seen in FIGS. 62-74. In another preferred form of the invention, window F is spaced proximally from the distal end surface of overtube 315.

Note that by providing visual marker C at the proximal end of the device, and by providing visual markers D and E at the distal end of the device, the user will always be guided as to the appropriate distance driver head 425 and flexible inserter shaft 195 are to be advanced, regardless of whether the user is looking at the proximal end of the device (e.g., inserter handle 405 and driver head 425, by direct visualization) or the distal end of the device (e.g., overtube 315 and knotless suture anchor 10, by endoscopic visualization).

In an alternative embodiment, overtube 315 is formed in a straight configuration. In this embodiment, inserter shaft 195 may be flexible or may be substantially rigid (i.e., it can omit features such as laser cuts 400 that provide flexibility to inserter shaft 195).

It will be appreciated that, in one preferred form of the invention, a transmission element (e.g., pull rod 35) is pulled proximally to pull a locking element (e.g., locking element 30) proximally so as to make an interference fit (e.g., a pinch fit) with a filament (e.g., suture S), whereby to bind the filament to a knotless suture anchor (e.g., knotless suture anchor 10). It will also be appreciated that, in one preferred form of the invention, the knotless suture anchor is mounted to a flexible inserter shaft (e.g., flexible inserter shaft 195), and the flexible inserter shaft is mounted to a slidable carriage (e.g., slidable inner carriage 420) which is mounted to a handle, such that movement of the slidable carriage will result in movement of the knotless suture anchor relative to the handle.

In accordance with the present invention, it should also be appreciated that a transmission element (e.g., a shaft, cable, etc.) can be rotated to rotate a locking element so as to make an interference fit (e.g., a pinch fit) with a filament (e.g., a suture), whereby to bind the filament to a knotless suture anchor.

And, in accordance with the present invention, it should also be appreciated that a transmission element (e.g., a shaft, cable, etc.) can be moved distally so as to move a locking element distally so as to make an interference fit (e.g., a pinch fit) with a filament (e.g., a suture), whereby to bind the filament to a knotless suture anchor.

In all of these cases, a transmission element (e.g., a rod, shaft, cable, etc.) is being moved (e.g., proximally, rotationally, distally) so as to make a locking element move (e.g., proximally, rotationally, distally) so as to make an interference fit (e.g., a pinch fit) with a filament (e.g., a suture), whereby to bind the filament to a knotless suture anchor. And in all of these cases, the knotless suture anchor may be mounted to a flexible inserter shaft (e.g., flexible inserter shaft 195), and the flexible inserter shaft may be mounted to a slidable carriage (e.g., slidable inner carriage 420) which is mounted to a handle, such that movement of the slidable carriage will result in movement of the knotless suture anchor relative to the handle.

Thus, in another form of the present invention, the locking element is rotated in order to secure the suture to the body of the knotless suture anchor. In this form of the invention, a rotation rod (i.e., the transmission element) is rotated so as to rotate the locking element and thereby bind the suture to the body of the knotless suture anchor. This rotation rod which rotates the transmission element is constructed so as to be flexible, so that it can curve with the shaft (i.e., flexible inserter shaft 195) which carries the knotless suture anchor in the angled outer tube (i.e., overtube 315). Furthermore, the slidable carriage preferably comprises an actuator which is coupled to rotation rod. This actuator can take the form of a rotatable knob which the user can rotate.

In yet another form of the invention, the locking element is pushed in order to secure the suture to the body of the knotless suture anchor. In this form of the invention, a push rod (i.e., the transmission element) is advanced distally to push the locking element distally and thereby bind the suture to the body of the knotless suture anchor. This push rod which pushes the transmission element is constructed so as to be flexible so that it can curve with shaft in the angled outer tube (i.e., overtube 315). Furthermore, the slidable carriage comprises an actuator coupled to the push rod. This actuator can take the form of a lever, cam, screw mechanism, etc. which the user actuates to advance the push rod, and hence the locking element, distally so as to secure the suture to the body of the knotless suture anchor.

In yet another alternative embodiment, knotless suture anchor 10 does not require actuation to lock suture S to the knotless suture anchor. For example, suture S may be locked by being squeezed or pressed between the body 25 of knotless suture anchor 10 and the side of bone hole H. Thus, the act of pressing knotless suture anchor 10 into bone hole H locks suture S to body 25 of knotless suture anchor 10. In this form of the invention, there is no need for actuation lever 430 or pull rod 35.

Use of the Novel Knotless Suture Anchor System for Other Tissue Re-Attachment

It should be appreciated that knotless suture anchor system 5 may also be used for re-attaching other soft tissue of the hip joint, or for re-attaching tissue of other joints, or for re-attaching tissue elsewhere in the body. In this respect it should be appreciated that knotless suture anchor system 5 may be used to attach soft tissue to bone or soft tissue to other soft tissue, or for attaching objects (e.g., prostheses) to bone or other tissue.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. Apparatus for securing an object to bone, said apparatus comprising:
   a handle having a distal end and a proximal end;
   a tube extending distally from said handle, the tube comprising a proximal end and a distal end, wherein the proximal end is fixedly mounted to the handle;
   a shaft extending distally from said handle, the shaft comprising a proximal end and a distal end, wherein the proximal end is movably mounted to the handle, and further wherein at least a portion of the shaft is disposed within the tube;
   an elongated member movably mounted to the handle and independently movable relative to the shaft; and
   an anchor comprising a first portion and a second portion, the first portion and the second portion being movable relative to one another, wherein at least a portion of the anchor is received in the tube, wherein one of the first portion and the second portion is releasably mechanically connected to the shaft and the other of the first portion and the second portion is releasably connected to the elongated member, wherein one of the first portion and the second portion carries a filament, and further wherein the first portion and the second portion are configured so that relative movement between the portion of the anchor carrying the filament and the portion of the anchor not carrying the filament binds the filament between the first portion and the second portion so as to bind the filament to the anchor.

2. Apparatus according to claim 1 further comprising:
   a slidable carriage movably mounted to said handle for movement between a proximal position and a distal position;
   wherein said proximal end of said shaft is mounted to said slidable carriage and said distal end of said shaft is releasably connected to said anchor;
   wherein said slidable carriage comprises a drive head extending out of said proximal end of said handle, such that applying a distal force to said drive head moves said slidable carriage from said proximal position toward said distal position;
   wherein the elongated member is movably mounted within said shaft, said elongated member having a distal end and a proximal end, said proximal end of said elongated member being mounted to said slidable carriage and said distal end of said elongated member being connected to said anchor.

3. Apparatus according to claim 2 wherein said elongated member moves one of the first portion of the anchor and the second portion of the anchor proximally.

4. Apparatus according to claim 2 wherein said elongated member rotates one of the first portion of the anchor and the second portion of the anchor.

5. Apparatus according to claim 2 wherein said elongated member moves one of the first portion of the anchor and the second portion of the anchor distally.

6. Apparatus according to claim 2 wherein said handle, said slidable carriage and said drive head are configured such that said drive head extends out of said proximal end of said handle regardless of whether said slidable carriage is in said proximal position or said distal position.

7. Apparatus according to claim 2 further comprising a visual marker disposed on said drive head for advising the user when said anchor has been properly inserted in bone.

8. Apparatus according to claim 7 wherein said visual marker is aligned with a selected portion of said handle when said anchor has been properly inserted into bone.

9. Apparatus according to claim 8 wherein said selected portion of said handle comprises said proximal end of said handle.

10. Apparatus according to claim 2 further comprising an actuator mounted to said slidable carriage, said proximal end of said elongated member being mounted to said actuator such that said actuator is configured to selectively move said elongated member whereby to move one of the first portion of the anchor and the second portion of the anchor relative to the other of the first portion of the anchor and the second portion of the anchor to bind the filament to the anchor.

11. Apparatus according to claim 1 wherein said tube is curved, and further wherein said shaft is flexible.

12. A method for securing an object to bone, said method comprising:
   providing an apparatus comprising:
      a handle having a distal end and a proximal end;
      a tube extending distally from said handle, the tube comprising a proximal end and a distal end, wherein the proximal end is fixedly mounted to the handle;
      a shaft extending distally from said handle, the shaft comprising a proximal end and a distal end, wherein the proximal end is movably mounted to the handle, and further wherein at least a portion of the shaft is disposed within the tube;
      an elongated member movably mounted to the handle and independently movable relative to the shaft; and an anchor comprising a first portion and a second portion, the first portion and the second portion being movable relative to one another, wherein at least a portion of the anchor is received in the tube, wherein one of the first portion and the second portion is releasably mechanically connected to the shaft and the other of the first portion and the second portion is releasably connected to the elongated member, wherein one of the first portion and the second portion carries a filament, and further wherein the first portion and the second portion are configured so that relative movement between the portion of the anchor carrying the filament and the portion of the anchor not carrying the filament binds the filament between the first portion and the second portion so as to bind the filament to the anchor;

forming a hole in the bone; and using an inserter to insert said anchor into the hole formed in the bone.

13. A method according to claim 12 wherein the apparatus further comprises:

a slidable carriage movably mounted to said handle for movement between a proximal position and a distal position;

wherein said proximal end of said shaft is mounted to said slidable carriage and said distal end of said shaft is releasably connected to said anchor;

wherein said slidable carriage comprises a drive head extending out of said proximal end of said handle, such that applying a distal force to said drive head moves said slidable carriage from said proximal position toward said distal position;

wherein the elongated member is movably mounted within said shaft, said elongated member having a distal end and a proximal end, said proximal end of said elongated member being mounted to said slidable carriage and said distal end of said elongated member being connected to said anchor.

14. A method according to claim 13 wherein said elongated member moves one of the first portion of the anchor and the second portion of the anchor proximally.

15. A method according to claim 13 wherein said elongated member rotates one of the first portion of the anchor and the second portion of the anchor.

16. A method according to claim 13 wherein said elongated member moves one of the first portion of the anchor and the second portion of the anchor distally.

17. A method according to claim 13 wherein said tube is curved, and further wherein said shaft is flexible.

18. A method according to claim 13 wherein said handle, said slidable carriage and said drive head are configured such that said drive head extends out of said proximal end of said handle regardless of whether said slidable carriage is in said proximal position or said distal position.

19. A method according to claim 13 wherein using said inserter to insert said anchor into the hole formed in the bone comprises:

manipulating said handle so as to align said distal end of said tube with the hole formed in the bone; and driving said drive head distally so as to insert said anchor into the hole formed in the bone.

20. A method according to claim 13 wherein said apparatus further comprises a visual marker disposed on said drive head for advising the user when said anchor has been properly inserted in bone.

21. A method according to claim 20 wherein said drive head is driven distally until said visual marker is aligned with a selected portion of said handle.

22. A method according to claim 21 wherein said selected portion of said handle comprises said proximal end of said handle.

23. A method according to claim 13 further comprising an actuator mounted to said slidable carriage, said proximal end of said elongated member being mounted to said actuator such that said actuator is configured to selectively move said elongated member whereby to move one of the first portion of the anchor and the second portion of the anchor relative to the other of the first portion of the anchor and the second portion of the anchor to bind the filament to the anchor.

24. Apparatus for securing an object to bone, said apparatus comprising:

a handle having a distal end and a proximal end;

a tube extending distally from said handle, the tube comprising a proximal end and a distal end, wherein the proximal end is fixedly mounted to the handle;

a shaft extending distally from said handle, the shaft comprising a proximal end and a distal end, wherein the proximal end is movably mounted to the handle, and further wherein at least a portion of the shaft is disposed within the tube;

an elongated member movably mounted to the handle and independently movable relative to the shaft;

an anchor comprising a first portion and a second portion, the first portion and the second portion being movable relative to one another, wherein at least a portion of the anchor is received in the tube, wherein one of the first portion and the second portion is releasably mechanically connected to the shaft and the other of the first portion and the second portion is releasably connected to the elongated member, wherein one of the first portion and the second portion receives a filament, and further wherein the first portion and the second portion are configured so that movement of the portion of the anchor receiving the filament relative to the other portion of the anchor binds the filament to the anchor; and a slidable carriage movably mounted to said handle for movement between a proximal position and a distal position;

wherein said proximal end of said shaft is mounted to said slidable carriage and said distal end of said shaft is releasably connected to said anchor;

wherein said slidable carriage comprises a drive head extending out of said proximal end of said handle, such that applying a distal force to said drive head moves said slidable carriage from said proximal position toward said distal position;

wherein the elongated member is movably mounted within said shaft, said elongated member having a distal end and a proximal end, said proximal end of said elongated member being mounted to said slidable carriage and said distal end of said elongated member being connected to said anchor.

25. A method for securing an object to bone, said method comprising:

providing an apparatus comprising:

a handle having a distal end and a proximal end;

a tube extending distally from said handle, the tube comprising a proximal end and a distal end, wherein the proximal end is fixedly mounted to the handle;

a shaft extending distally from said handle, the shaft comprising a proximal end and a distal end, wherein the proximal end is movably mounted to the handle, and further wherein at least a portion of the shaft is disposed within the tube;

an elongated member movably mounted to the handle and independently movable relative to the shaft;

an anchor comprising a first portion and a second portion, the first portion and the second portion being movable relative to one another, wherein at least a portion of the anchor is received in the tube, wherein one of the first portion and the second portion is releasably mechanically connected to the shaft and the other of the first portion and the second portion is releasably connected to the elongated member, wherein one of the first portion and the second portion receives a filament, and further wherein the first portion and the second portion are configured so that movement of the portion of the anchor receiving the filament relative to the other portion of the anchor binds the filament to the anchor; and a slidable carriage movably mounted to said handle for movement between a proximal position and a distal position;

wherein said proximal end of said shaft is mounted to said slidable carriage and said distal end of said shaft is releasably connected to said anchor;

wherein said slidable carriage comprises a drive head extending out of said proximal end of said handle, such that applying a distal force to said drive head moves said slidable carriage from said proximal position toward said distal position;

wherein the elongated member is movably mounted within said shaft, said elongated member having a distal end and a proximal end, said proximal end of said elongated member being mounted to said slidable carriage and said distal end of said elongated member being connected to said anchor;

forming a hole in the bone; and using an inserter to insert said anchor into the hole formed in the bone.

\* \* \* \* \*